(12) United States Patent
Penney et al.

(10) Patent No.: US 7,683,061 B2
(45) Date of Patent: Mar. 23, 2010

(54) TRIAZINE DIMERS FOR THE TREATMENT OF AUTOIMMUNE DISEASES

(75) Inventors: Christopher Penney, Pierrefonds (CA); Boulos Zacharie, Laval (CA); Shaun D. Abbott, Pointe-Claire (CA); Jean-François Bienvenu, Laval (CA); Alan D. Cameron, Montreal (CA); Jean-Simon Duceppe, St.-Colomban (CA); Abdallah Ezzitouni, Laval (CA); Daniel Fortin, Rosemère (CA); Karine Houde, Montreal (CA); Nancie Moreau, Laval (CA); Nicole Wilb, Montreal (CA); Brigitte Grouix, Montreal (CA); Lyne Gagnon, Laval (CA)

(73) Assignee: ProMetic BioSciences Inc., Montreal, Quebec (CA)

( * ) Notice: Subject to any disclaimer, the term of this patent is extended or adjusted under 35 U.S.C. 154(b) by 212 days.

(21) Appl. No.: 10/580,237

(22) PCT Filed: Nov. 22, 2004

(86) PCT No.: PCT/CA2004/002003

§ 371 (c)(1),
(2), (4) Date: May 23, 2006

(87) PCT Pub. No.: WO2005/049607

PCT Pub. Date: Jun. 2, 2005

(65) Prior Publication Data

US 2007/0149528 A1   Jun. 28, 2007

Related U.S. Application Data

(60) Provisional application No. 60/524,021, filed on Nov. 24, 2003.

(51) Int. Cl.
| | |
|---|---|
| C07D 403/12 | (2006.01) |
| C07D 403/14 | (2006.01) |
| A61K 31/53 | (2006.01) |
| A61K 39/395 | (2006.01) |
| A61P 13/12 | (2006.01) |
| A61P 17/06 | (2006.01) |
| A61P 19/02 | (2006.01) |
| A61P 37/00 | (2006.01) |
| A61M 1/36 | (2006.01) |
| C07K 1/22 | (2006.01) |
| C07K 16/24 | (2006.01) |

(52) U.S. Cl. .................. 514/245; 544/198; 544/207
(58) Field of Classification Search ............. 544/198, 544/207; 514/245
See application file for complete search history.

(56) References Cited

U.S. PATENT DOCUMENTS

| 4,731,393 A | * | 3/1988 | Karrer et al. ............... 522/117 |
| 5,606,055 A | | 2/1997 | Matsumoto et al. |
| 5,629,382 A | | 5/1997 | Cipolli et al. |
| 6,482,255 B1 | * | 11/2002 | Lavery et al. ............ 106/31.48 |

FOREIGN PATENT DOCUMENTS

| EP | 0 310 139 | | 4/1989 |
| EP | 0 542 374 | * | 12/1992 |
| GB | 2 053 926 | * | 2/1981 |
| GB | 0 122 458 | * | 10/1984 |
| GB | 2 149 808 | * | 6/1985 |
| WO | WO 01/42228 | * | 6/2001 |

OTHER PUBLICATIONS

Haraoui, B., The Journal of Rheumatology, vol. 32, Supplement 74, 3-7, 2005.*
Bongartz., et al., JAMA, vol. 295(19), 2275-2285, 2006.*
Seko et al., Autoimmunity Reviews, 5, 299-305, 2006.*
Moller et al., Springer Semin. Immun., 27, 391-408, 2006.*
Tracey et al., Pharmacology & Therapeutics, 117, 244-274, 2008.*
Bradley, J.R., Journal of Pathology, 214(2): 149-160, 2008.*

* cited by examiner

*Primary Examiner*—Venkataraman Balasubramanian
(74) *Attorney, Agent, or Firm*—Clark & Elbing LLP

(57) ABSTRACT

Compounds containing two mono- or disubstituted triazine rings covalently linked by an organic linker, but not linked directly to each other, may be used to treat autoimmune diseases. Autoimmune diseases which are amenable to treatment with compounds of this invention include rheumatoid arthritis, systemic lupus erythematosus (SLE), idiopathic (immune) thrombocytopenia (ITP), glomerulonephritis and vasculitis. The present invention also relates to reducing drug toxicity which often accompanies traditional therapies for autoimmune diseases. The compounds may also be used to bind antibody in vitro or ex vivo.

24 Claims, 7 Drawing Sheets

*MTX is significantly different from control for the rest of the protocol.
**Compound 1 is significantly different from the control.

Inflammation significantly inferior to control
Compound 19a IV: Days 1, 2, 3, 4, 5, 6, 12, 13, 14, 15, 16, 18 and 19
MTX: Days 5, 15, 16, 17, 18, 19 and 21
Compound 19a PO: Days 1, 3, 5 and 6
Compound 1 PO: Days 4, 5 and 16
Compound 1 IV: Days 16 and 19

— ♦ — Control
— ■ — MTX
— ▲ — Compound 1-IV
— ■ — Compound 19a-IV
— ✱ — Compound 1-PO
— ○ — Compound 19a-PO Inflammation significantly inferior to control
Compound 19a IV: Days 13, 14, 15, 16, 18 and 20.
Methotrexate: Days 14, 15, 16, 18 and 20.
Compound 19a PO: Days 13, 14, 15, 16, 19, 20, 21 and 22.

→ Control
→ Methotrexate
→ Compound 19a-IV
→ Compound 19a-PO

TRIAZINE DIMERS FOR THE TREATMENT OF AUTOIMMUNE DISEASES

CROSS-REFERENCE TO RELATED APPLICATIONS

This application is a U.S. national stage of International Patent Application No. PCT/CA2004/002003, filed 22 Nov. 2004, which designated the U.S. and claims priority of U.S. Provisional Application No. 60/524,021, filed 24 Nov. 2003; the entire contents of each of which are hereby incorporated by reference.

FIELD OF THE INVENTION

The present invention relates to the treatment of autoimmune diseases with now organic compounds. These compounds contain two mono- or disubstituted triazine rings covalently linked by an organic linker, but not linked directly to each other.

BACKGROUND OF THE INVENTION

Autoimmune disease refers to any of a group of disorders or diseases in which tissue injury is associated with a humoral and/or cell-mediated immune response to body constituents or, in a broader sense, an immune response "to self". The pathological immune response may be systemic or organ specific. That is, for example, the immune response directed to self may affect joints, skin, the myelin sheath that protects neurons, kidney, liver, pancreas, thyroid, adrenals and ovaries. In fact, the list of autoimmune diseases is composed of more than eighty disorders. A few autoimmune diseases such as vitiligo, in which patches of skin lose pigmentation, are merely annoying. Most others are debilitating, often progressive with time and eventually fatal. Systemic lupus erythematosus (SLE), for example, is a chronic disease in which 10-15% of patients die within a decade of diagnosis. In all but a few autoimmune diseases, the sex ratio skews towards women. For example, in SLE the ratio of female to male patients is nine to one. In one particular case, Hashimoto's disease in which the immune system attacks the thyroid gland, the ratio is fifty to one.

It has long been known that immune complex formation plays a role in the etiology and progression of autoimmune disease. For example, in Goodman and Gilman's The Pharmacological Basis of Therapeutics, 16$^{th}$ Edition (1980), Macmillan Publishing Co., on page 683, inflammation in patients with arthritis is stated to probably involve phagocytosis by leukocytes of complexes of antigen, antibody and complement—immune complexes. But it is only now being recognized that inflammation caused by immune complexes in the joints (arthritis), the kidneys (glomerulonephritis) and blood vessels (vasculitis) is a major cause of morbidity in autoimmune diseases as noted by P. M. Hogarth et al., Annual Reports in Medicinal Chemistry, 37, 217-224 (2002). Increased immune complex formation correlates with the presence of antibodies directed to self or so-called autoantibodies, and the presence of the latter can also contribute to tissue inflammation either as part of an immune complex or unbound to antigen (free antibody). In some autoimmune diseases, the presence of free autoantibody contributes significantly to disease pathology. This has been clearly demonstrated for example, in SLE (anti-DNA antibodies), ITP (antibody response directed to platelets) and to a lesser extent rheumatoid arthritis (IgG reactive rheumatoid factor). The importance of the role of immune complexes and free autoantibodies is further demonstrated by the fact that successful treatment of certain autoimmune diseases has been achieved by the removal of immune complexes and free antibody by specific immunoadsorption procedures. For example, the use of an apheresis procedure in which immune complexes and antibodies are removed by passage of a patient's blood through an immunoaffinity (Prosorba®) column was approved by the U.S. FDA in 1987 ITP and in 1999 for rheumatoid arthritis. Currently, however, there is no approved method for the treatment of autoimmune diseases which facilitates the elimination of immune complexes and autoantibodies by administration of a drug.

Another aspect of the etiology and progression of autoimmune disease is the role of proinflammatory cytokines. Under normal circumstances, proinflammatory cytokines such as tumor necrosis factor α (TNFα) and interleukin-1 (IL-1) play a protective role in the response to infection and cellular stress. But the pathological consequences which result from chronic and/or excessive production of TNFα and IL-1 are believed to underlie the progression of many autoimmune diseases such as rheumatoid arthritis, Crohn's disease, inflammatory bowel disease and psoriasis. Other proinflammatory cytokines include interleukin-6, interleukin-8, interleukin-17 and granulocyte-macrophage colony stimulating factor. It appears, however, that TNFα is on the top of the proinflammatory cytokine cascade. That is, in terms of blocking one proinflammatory cytokine, blockage of TNFα would provide the maximum therapeutic effect. The ability of TNFα to downregulate other proinflammatory cytokines is reviewed by M. Feldmann in Perspectives, 2:364-371 (2002). Indeed, the impact of the antagonism of TNFα as a treatment option for arthritis, psoriatic arthritis, psoriasis and Crohn's disease has been illustrated by the U.S. FDA approval of Remicade (chimeric anti-TNFα monoclonal antibody), Enbrel (soluble TNFα p75 receptor fusion protein) and Humira (human anti-TNFα monoclonal antibody).

As may be inferred from the above discussion regarding the etiology and progression of autoimmune disease, its pathogenesis is complex and multifactorial. As such, there arm a multitude of therapies available. But the majority of autoimmune diseases are poorly controlled by current treatments. Conventional treatments are not uniformly effective and are often associated with moderate to severe toxicity. Nonetheless, the above discussion indicates that there is a need for simple, well-defined organic compounds which can help the body eliminate immune complexes or at least prevent the deposition of circulating immune complexes and/or (simultaneously) inhibit the activity of TNFα while still being generally nontoxic to the patient. In summary, there is a need for an efficacious yet nontoxic treatment of chronic autoimmune disease.

The present invention provides compounds that are useful for the treatment of chronic autoimmune disease. Although not initially life-threatening, most autoimmune diseases are chronic conditions which slowly progress to a debilitating state. While numerous therapies are available, conventional treatments are not routinely efficacious. More problematic is the accompanying toxicity which often prohibits the long-term use necessary with a chronic disease. Current treatments for autoimmune disease can be broadly classified into two groups: those drugs which dampen or suppress the immune response to self and those drugs which address the symptoms that arise from chronic inflammation. In greater detail, conventional treatments for autoimmune disease (e.g., primarily arthritis) are as follows:

1. Nonsteroidal Anti-Inflammatory Drugs (NSAIDs): These include aspirin, ibuprofen, naproxen, etodolac and ketoprofen. NSAIDs are not relatively potent drugs and so are most commonly used as anti-inflammatory drugs in the early stages of disease (e.g., to relieve the pain and swelling which accompanies arthritis). But NSAIDs are associated with gastrointestinal irritation and liver toxicity. In order to address the gastrointestinal ulceration associated with the use of many NSAIDs, more selective NSAID drugs have been recently developed which selectively inhibit (Vioxx, Celebrex) or preferentially inhibit Mobicox) cyclooxygenase-2 (COX-2 inhibitors). COX-2 inhibitors, however, display untoward side effects which include gastrointestinal irritation, especially with longer-term use.

2. Corticosteroids: These include prednisone and dexamethasone. Corticosteroids are the most widely used anti-inflammatory agents for the treatment of rheumatoid arthritis. But they significantly increase the risk of osteoporosis, gastrointestinal toxicity and infection arising from generalized immune suppression. Therefore, corticosteroids tend to be used for the treatment of disease flares (e.g., SLE) and not as a chronic treatment.

3. Disease-Modifying Anti-Rheumatic Drugs (DMARDs): These include cytotoxic drugs such as methotrexate, azathioprine and cyclophosphamide, potent immunosuppressants such as cyclosporin A (Sandimmune, Neoral) and FK506 (tacrolimus) and a variety of other drugs such as hydrocloroquine and organogold salts (e.g., aurothioglucose). DMARDs are potent drugs and so can display significant efficacy in reducing inflammation and slowing the rate of disease progression. As such, physicians have traditionally used DMARDs as a second line of therapy after NSAIDs. As potent drugs, however, DMARDs have significant toxicity associated with their use. Cytotoxic drugs, for example, interfere with DNA replication which manifests itself with a number of toxic effects. The latter include bone marrow depression and subsequent risk of infection and neoplasia. The use of cyclosporin A and FK506 is limited by serious side effects which include renal and liver toxicities. Toxic effects associated with the use of hydrochloroquine include blindness, neuromyopathy and gastrointestinal distress. The most common side effect arising from therapy with gold salts is dermatitis. But gold toxicity can also cause nephritis and bone marrow depression.

4. Biologicals: These include the recombinant proteins Remicade, Enbrel and Humira, all of which target TNFα, Kineret, which targets interleukin-1, Amevive, which targets T-cells (CD2 surface glycoprotein) and Raptiva which also targets T-cells (anti-CD11a antibody). But recombinant proteins and, in particular, recombinant antibodies are difficult to produce for widespread use and have toxic side effects associated with their use. Toxicities include potential immunological reactions, especially with the prolonged use that may be required for chronic conditions. In addition to the well-known HAMA (human anti-mouse antibody) response associated with chimeric or human antibodies, antibody mediated cytotoxicity mechanisms (ADCC and complement-mediated) may lead to side effects. More recently, it was discovered that antibodies, regardless of source or antigen specificity, can convert molecular oxygen into hydrogen peroxide and ozone as described by P. Wentworth et al. Science 293, 1806-1811 (2001) and 298, 2195-2199 (2002). This could lead to cellular and tissue damage which may exacerbate treatment of an autoimmune condition with prolonged use. For example, it was shown that the production of hydrogen peroxide and ozone by antibodies could be linked to an inflammatory response in rats: a so-called Arthus reaction. The potent anti-TNFα activity of the antibody Remicade has led to increased risk of opportunistic infections which include tuberculosis, histoplasmosis, listeriosis and pneumocytosis.

Therefore, it is an objective of the present invention to provide novel compounds for use in treating autoimmune disease.

SUMMARY OF THE INVENTION

The present invention relates to a novel method for the treatment of chronic autoimmune disease, in particular arthritis and SLE, by administration of a compound to a mammal, preferably a human. Therefore, in accordance with this invention, certain mono- or disubstituted triazine dimers (in which one triazine monomer is connected to the other by an organic linker) and their pharmaceutical compositions are provided which are able to facilitate the clearance of immune complexes or to limit their deposition within body organs such as kidney and/or to inhibit the proinflammatory actions of TNFα. In a preferred embodiment of this invention, these triazine compounds will affect both aspects of the inflammation process: immune complexes and TNFα. The therapeutic benefit resulting from this dual mechanism of action will manifest itself in terms of an improved toxicity profile. That is, the triazine compounds described in this invention are not potent inhibitors of TNFα nor will they completely eliminate immune complexes. TNFα does play a role in protection against infection while immune complexes play a role in feed-back mechanisms regulating immune responses (so-called idiopathic determinants). Therapeutic efficacy may result from the additive effect of the two mechanisms of action. Furthermore, toxicity due to chronic treatment and/or other drugs used in combination may be at least reduced or avoided.

In another embodiment of the present invention, the triazine compounds will affect only one aspect of the inflammation process. That is, these compounds will affect either immune complexes or TNFα. In the case where the triazine compounds influence the elimination of immune complexes or prevent their deposition, such compounds are expected to be particularly useful for the treatment of arthritis, systemic lupus erythematosus (SLE), idiopathic (immune) thrombocytopenia (ITP), glomerulonephritis and vasculitis. In the case where the triazine compounds inhibit TNFα, such compounds are expected to be particularly useful for the treatment of rheumatoid arthritis, psoriatic arthritis, psoriasis, Crohn's disease, inflammatory bowel disease, ankylosing spondylitis, Sjögren's syndrome, Still's disease (macrophage activation syndrome), uveitis, scleroderma, myositis, Reiter's syndrome and Wegener's syndrome. Of course, it is possible that some triazine compounds of this invention will affect the inflammation process by a biochemical mechanism which is in addition to and distinct from an effect on immune complexes and/or TNFα. But regardless of the mechanism(s) by which the triazine compounds affect the targeted autoimmune disease, it is an important aspect of this invention that said compounds do not potently affect any aspect of the inflammation process such that a deleterious toxicity will result.

Further aspects of the invention will be apparent to a person skilled in the art from the following description and claim, and generalizations thereto.

BRIEF DESCRIPTION OF THE DRAWINGS

FIGS. 2-3 illustrate the effect of compound 1 on NZBx-NZW mice: mortality (FIG. 2) or proteinuria (FIG. 3).

DETAILED DESCRIPTION OF THE INVENTION

Figure 1:
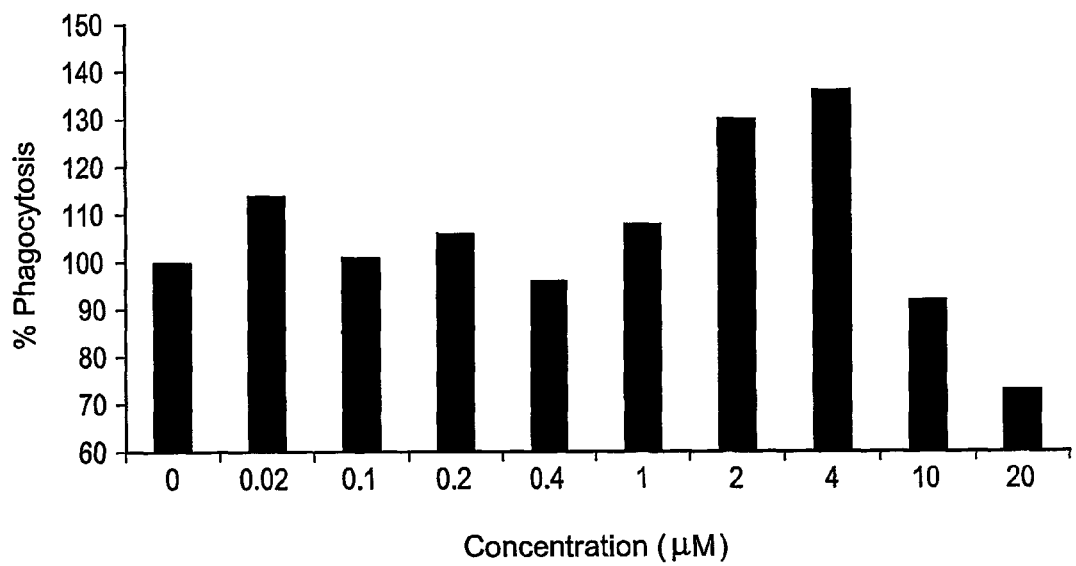
FIG. 1 illustrates a dose-response curve of compound 1 on the phagocytosis of immune complexes by RAW 264.7 macrophage-like cells.

The present invention includes compounds, or pharmaceutically acceptable derivatives thereof, of the following general formula:

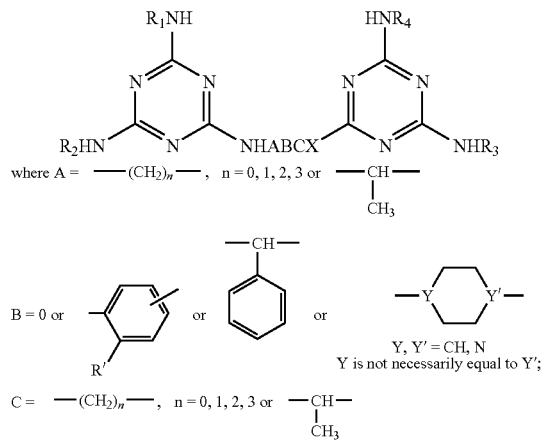

$X = NH, O, S$;
$R' =$ hydrogen or $C_{1-4}$ alkyl, $C_{1-4}$ N-methylaminoalkyl or N,N-dimethylaminoalkyl A is not necessarily equal to C;

and wherein $R_1$, $R_2$, $R_3$ and $R_4$ are independently selected from the group consisting of hydrogen, $C_{2-6}$ alkyl or alkenyl, $C_{2-6}$ hydroxyalkyl, $C_{2-6}$ aminoalkyl, trifluoromethyl, pentafluoroethyl, phenyl, naphthyl, benzyl, biphenyl, phenethyl, piperazinyl, N-methylpiperazinyl, N-ethylpiperazinyl, morpholinyl, piperidinyl, methylpiperidinyl, ethylpiperidinyl, indenyl, 2,3-dihydroindenyl, $C_4$-$C_7$ cycloalkyl or cycloalkenyl, indoyl, methylindoyl, ethylindoyl, or substituted five-membered aromatic heterocyclic rings of the following formulas:

$n = 0, 1, 2$

X is defined as above and Z=NH, $CH_2$ or substituted phenyl rings of the following formulas:

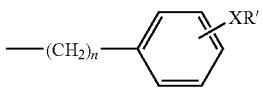

$n = 0, 1, 2$

X and R' are defined as above.

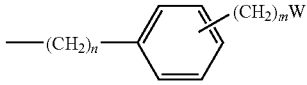

$n = 0, 1, 2$
$m = 0, 1, 2$
n is not necessarily equal to m

W=hydrogen, $CH_3$, $NH_2$, COOR', OR'.

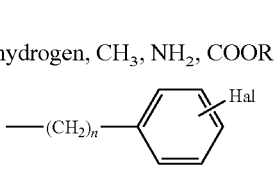

$n = 0, 1, 2$

Hal=Halogen (F, Cl, etc.).

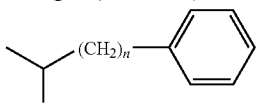

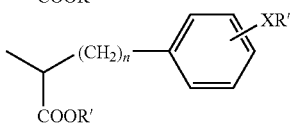

$n = 0, 1, 2$

X and R' are defined as above.

In one aspect of the present invention, there are provided disubstituted triazine dimers in which each triazine monomer is connected to the other by an organic linker wherein said linker contains a 1,3- or 1,4 substituted phenyl group. That is,

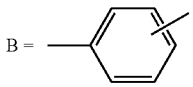

In such cases, it is possible for A=C=0 and the phenyl group becomes the linker which connects the two triazine monomers. In such a case, the general formula becomes:

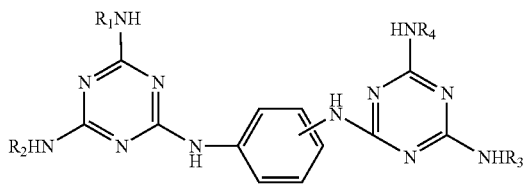

This represents one preferred aspect of his invention when A=C=0 but another preferred embodiment is provided when A=—(CH$_2$)$_n$—, where n=1 or 2 while C=0, or A=0 while C=—(CH$_2$)$_n$— where n=1 or 2, or A=C=—(CH$_2$)$_n$— where n=1 or 2. Thus, for example, a preferred aspect of this invention is A=—(CH$_2$)$_2$— and C=0, or A=0 and C=—(CH$_2$)$_2$—. In one preferred case, the general formula becomes:

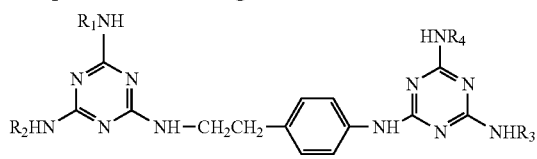

In an alternative embodiment of the invention, no phenyl group is present in the organic linker which connects the two disubstituted triazine rings, or B=0. That is, the triazine dimers are connected by an alkyl chain. Thus, for example, another preferred aspect of this invention is A=C=—CH$_2$— and B=0. Therefore, the organic linker contains a —CH$_2$CH$_2$— or ethylene group and the general formula becomes:

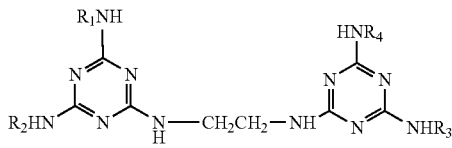

Regardless of the organic linker which connects the two triazine rings, it is a preferred embodiment of this invention that R$_1$, R$_2$, R$_3$ and R$_4$ are defined as follows:

R$_1$=hydroxyethyl, hydroxypropyl, hydroxybutyl
=aminoethyl, aminopropyl, aminobutyl
=phenyl, anilino, hydroxyphenyl
R$_2$=phenethyl, hydroxyphenethyl, aminophenethyl
= R$_3$
R$_4$=phenyl, anilino, hydroxyphenyl Particularly preferred are the following compounds:

Group 1 compounds where A=—CH$_2$—, B=0, C=—CH$_2$— (ethylene linker):

| Compound No. | Structure |
|---|---|
| 1 | ![structure 1] |
| 2 | ![structure 2] |

-continued
| Compound No. | Structure |
|---|---|
| 3 | 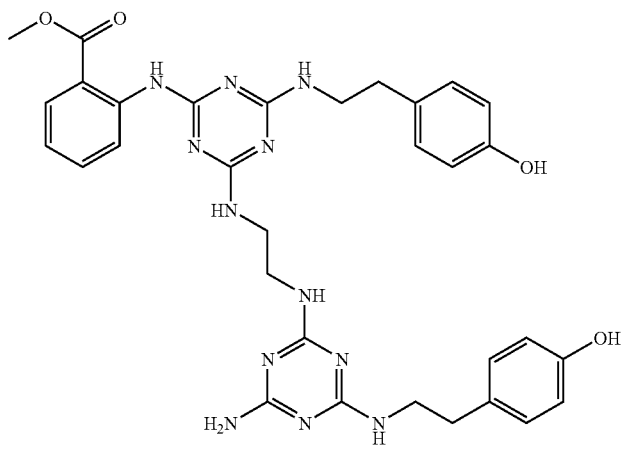 |
| 4 | 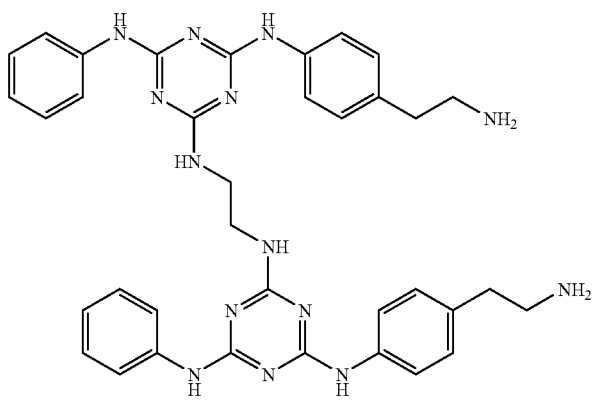 |
| 5 | 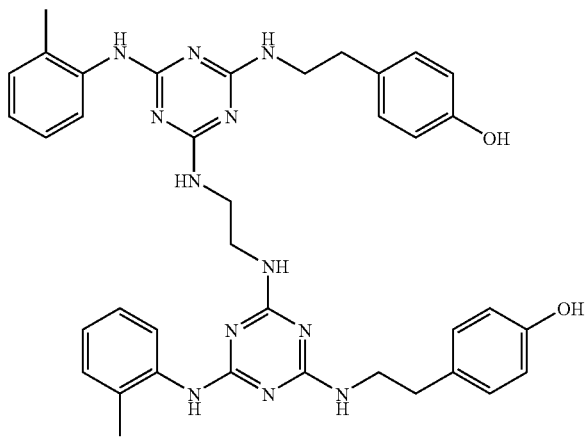 |

| Compound No. | Structure |
|---|---|
| 6 | 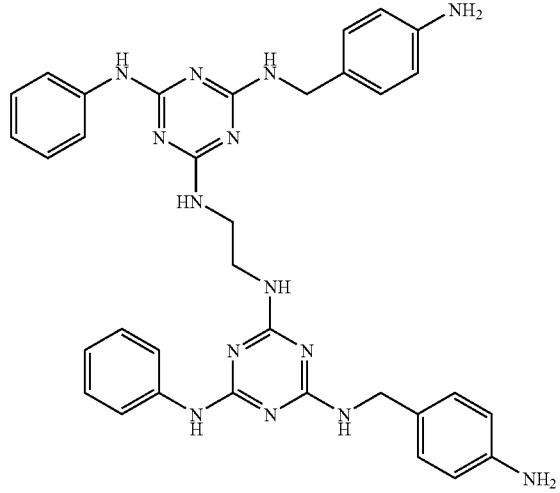 |
| 7 | 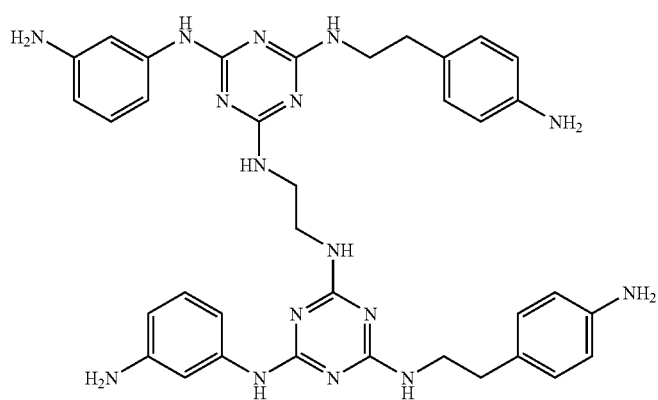 |
| 8 | 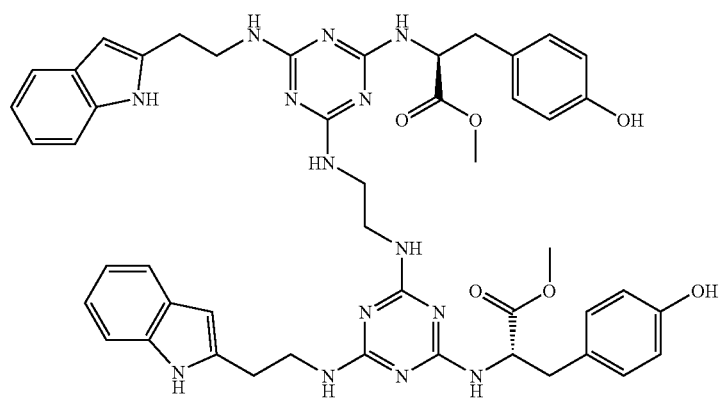 |

-continued
| Compound No. | Structure |
|---|---|
| 9 | 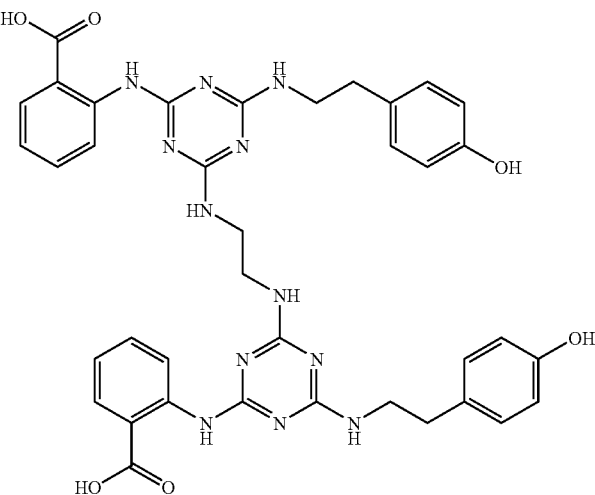 |
| 10 | 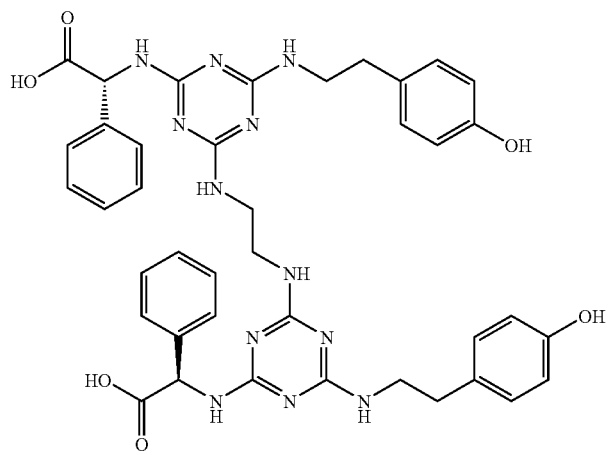 |
| 11a 11b | 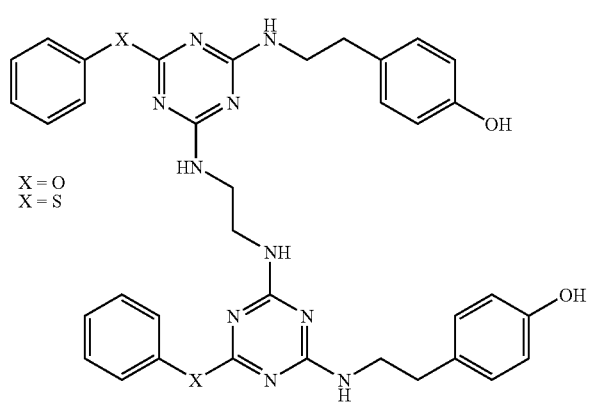  X = O  X = S |

| Compound No. | Structure |
|---|---|
| 12 | 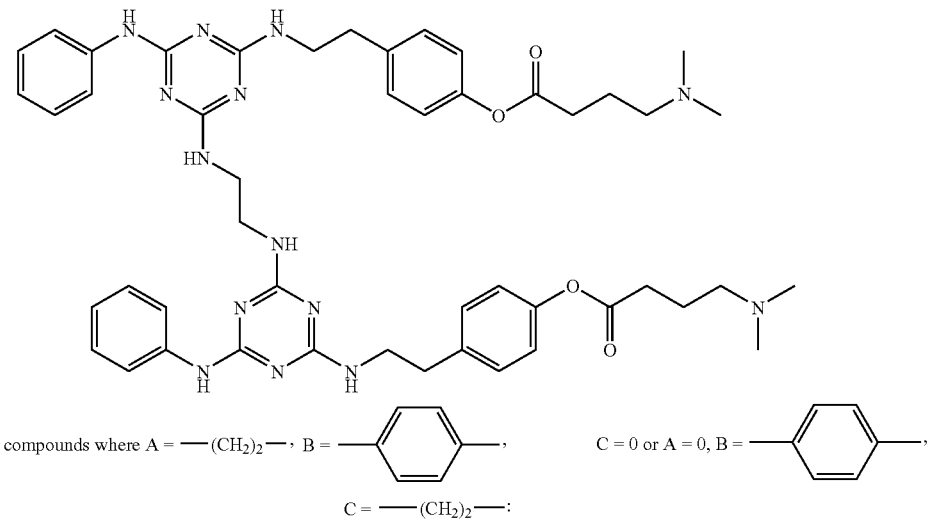 Group 2 compounds where A = —(CH₂)₂—, B = —⌬—, C = O or A = 0, B = —⌬—, C = —(CH₂)₂—: |
| 13 | 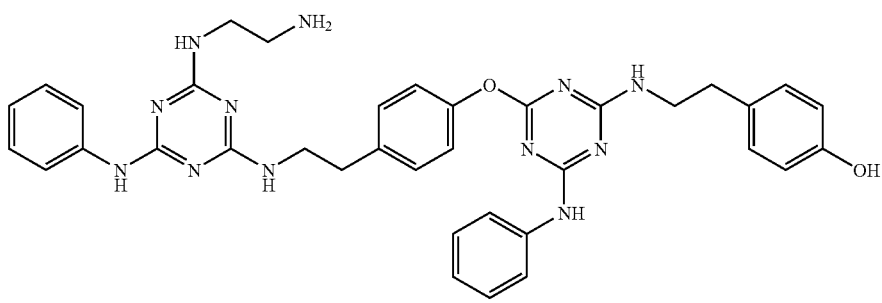 |
| 14 | 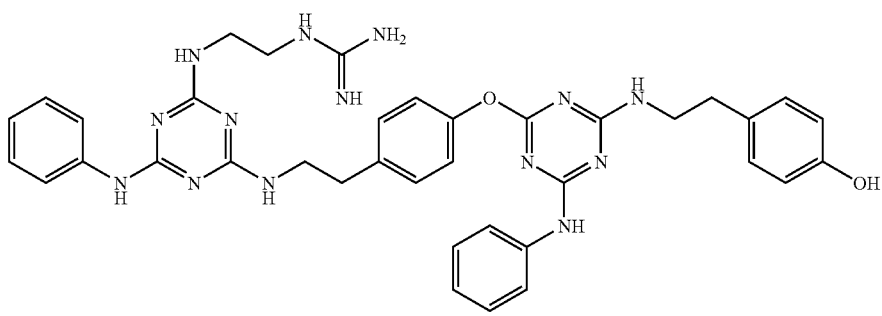 |
| 15 | 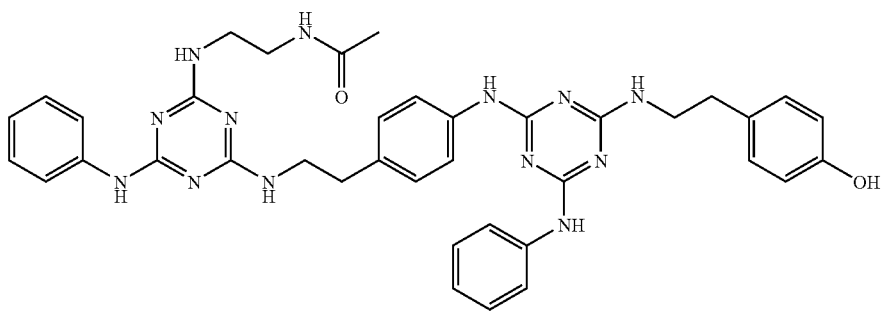 |

-continued
| Compound No. | Structure |
|---|---|
| 16 | 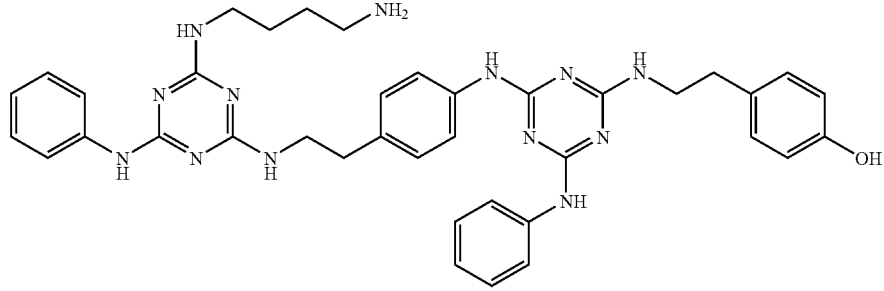 |
| 17 | 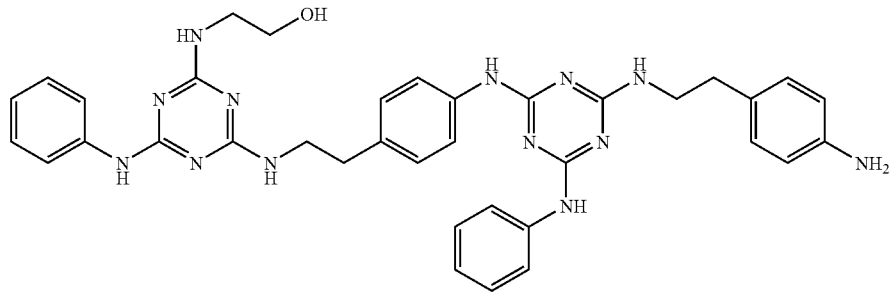 |
| 18 | 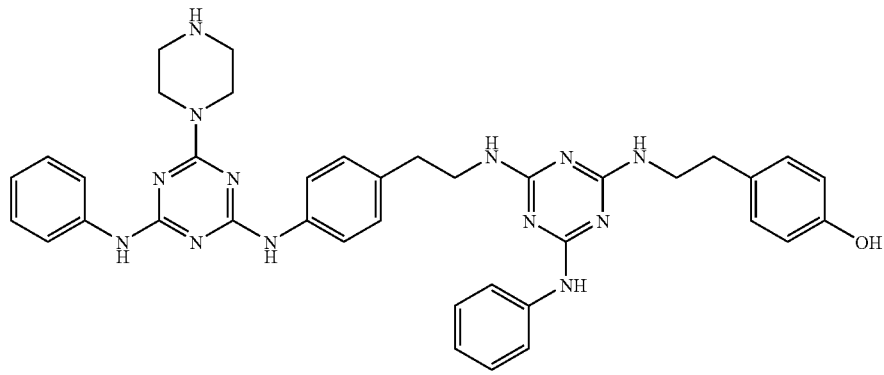 |
| 19a<br>X = OH<br>19b<br>X = NH$_2$ | 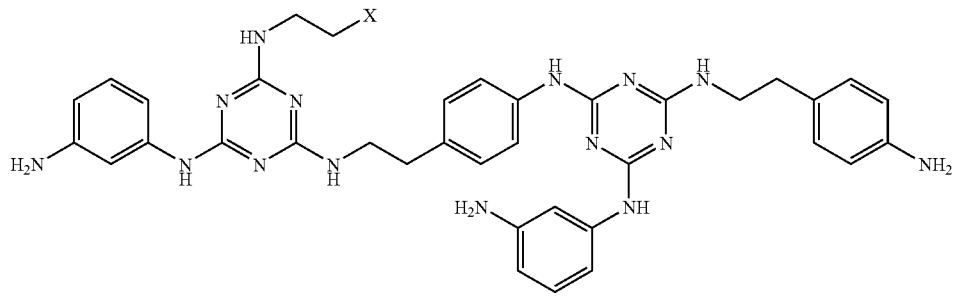 |
| 20 | 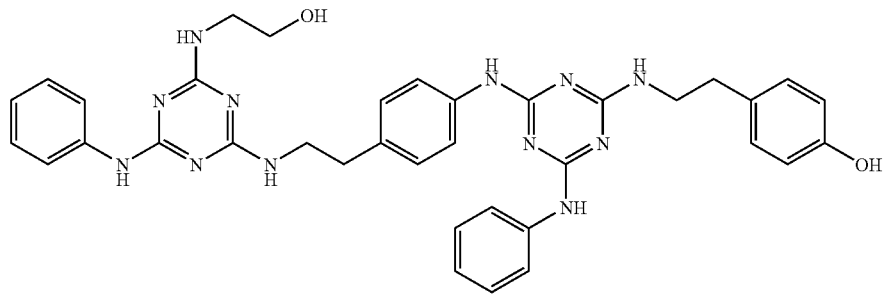 |

-continued
| Compound No. | Structure |
|---|---|
| 21 | 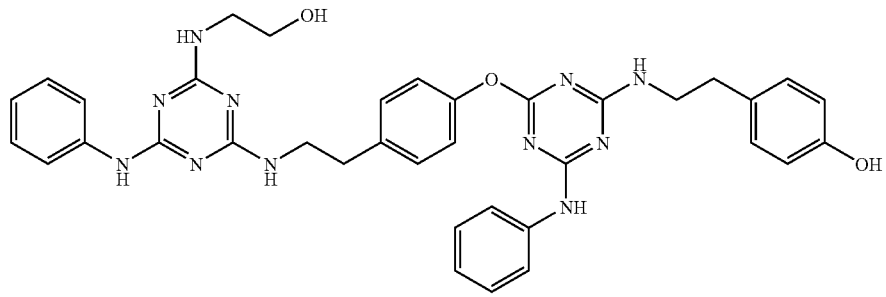 |
| 22 | 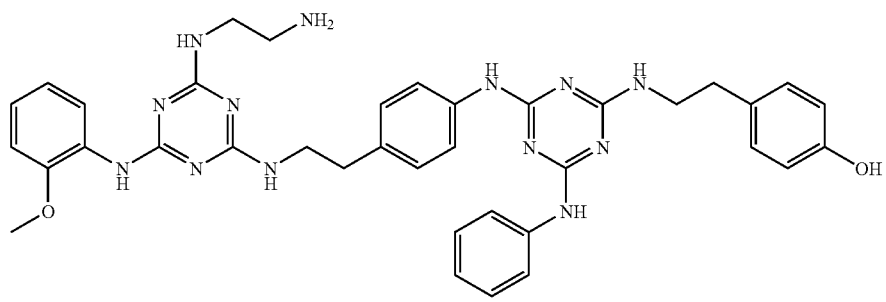 |
| 23 | 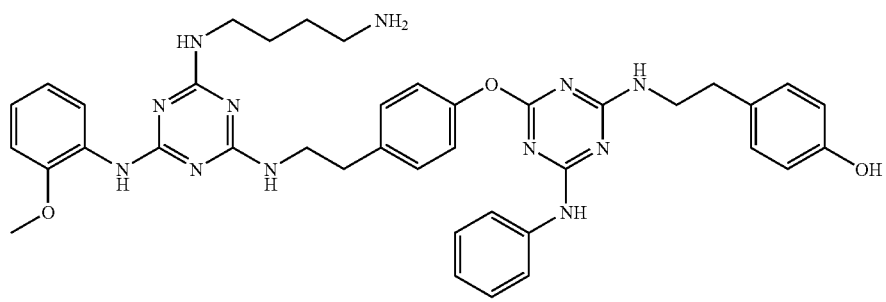 |
| 24 | 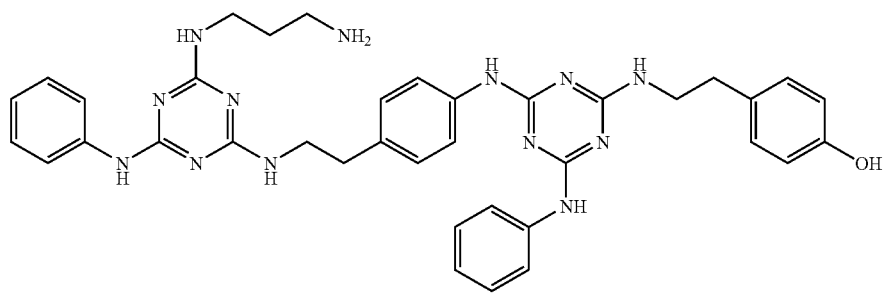 |
This invention is, however, not limited to the above two groups of compounds, and other particularly preferred compounds include the following:

| Compound No. | Structure |
|---|---|
| 25 | 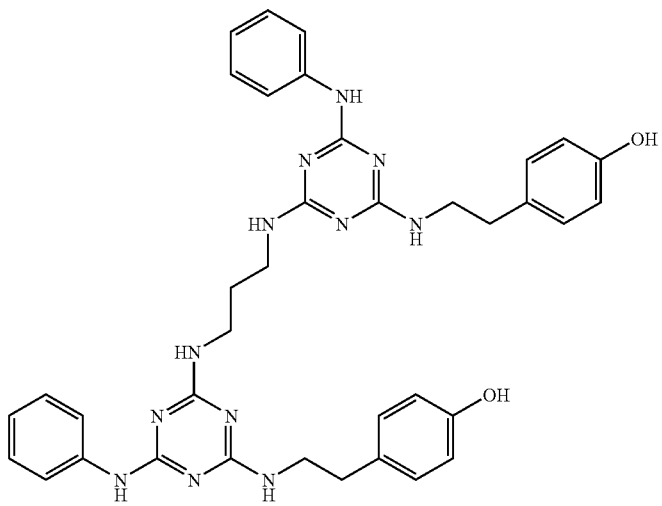 |
| 26 | 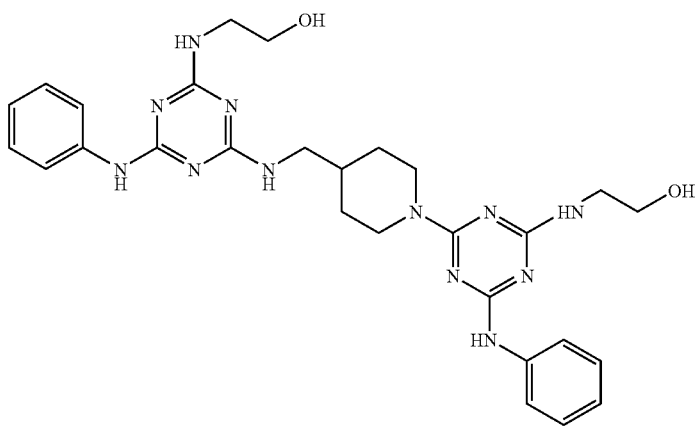 |
| 27 | 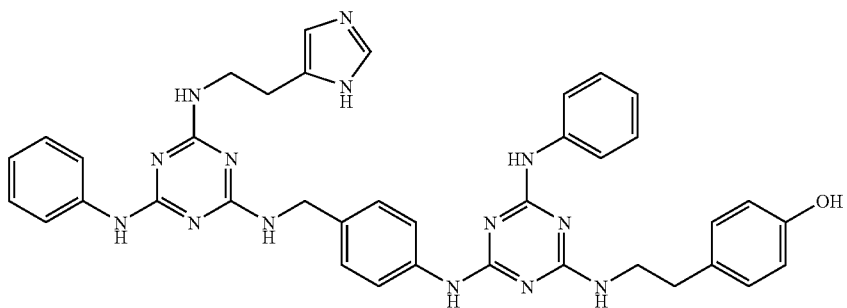 |

-continued
| Compound No. | Structure |
|---|---|
| 28 | 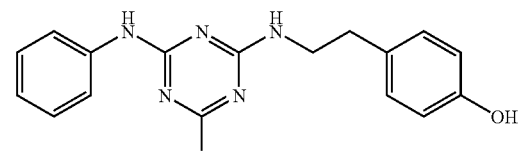 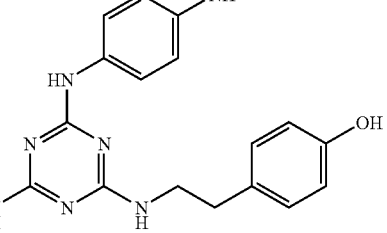 |
| 29 | 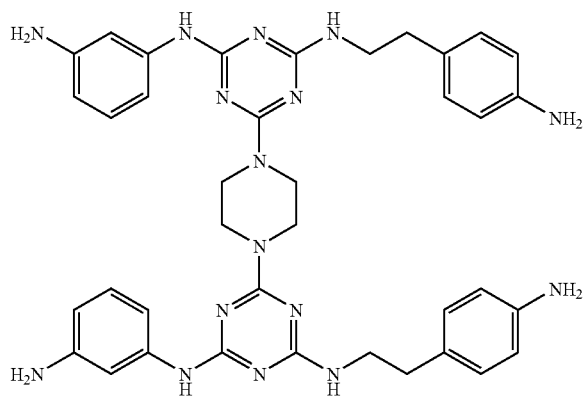 |
| 30 | 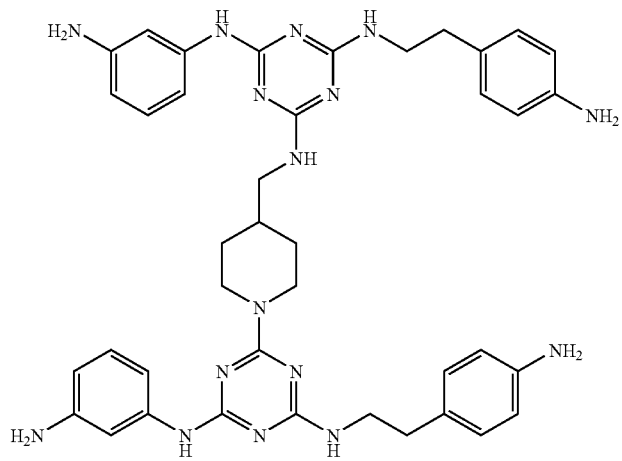 |
| 31 | 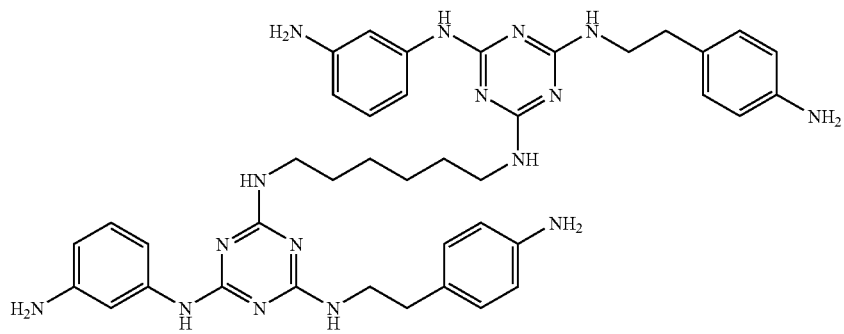 |

| Compound No. | Structure |
|---|---|
| 32 | 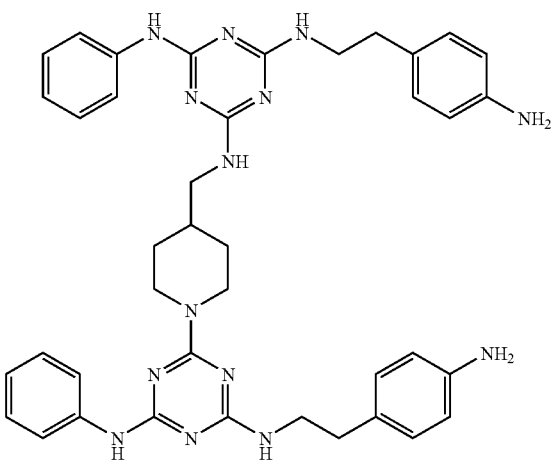 |
| 33 | 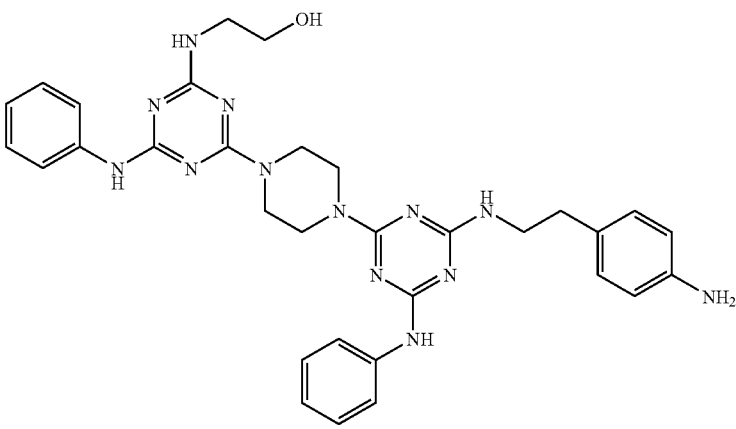 |
| 34 | 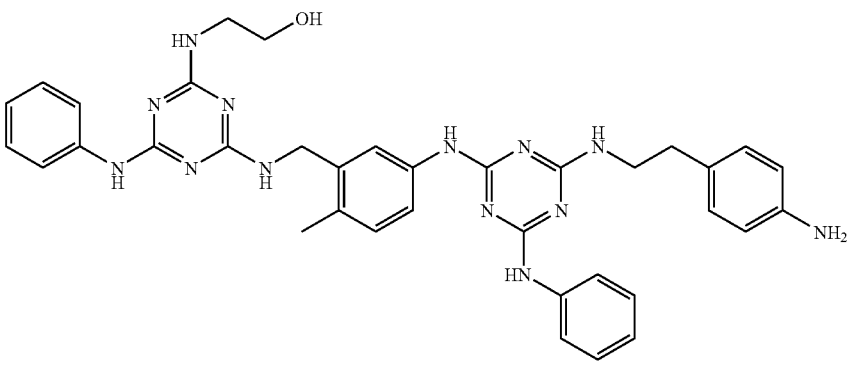 |

-continued
| Compound No. | Structure |
|---|---|
| 35 | 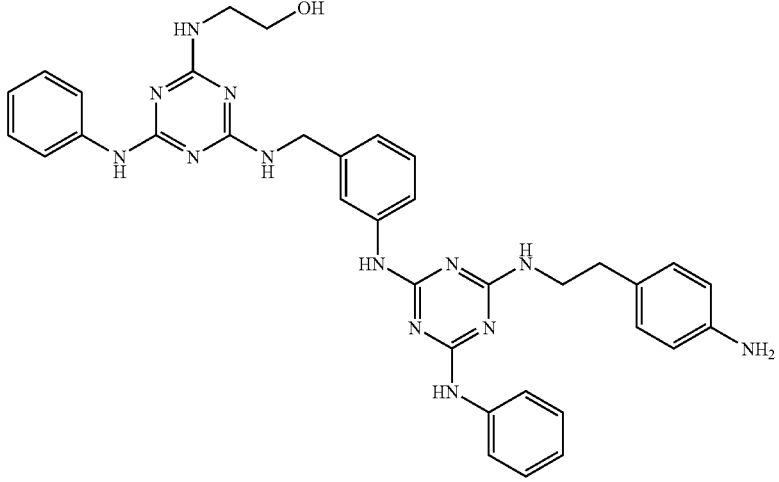 |
| 36 | 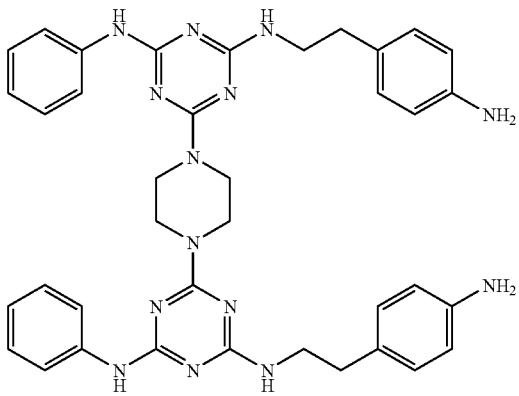 |
| 37 | 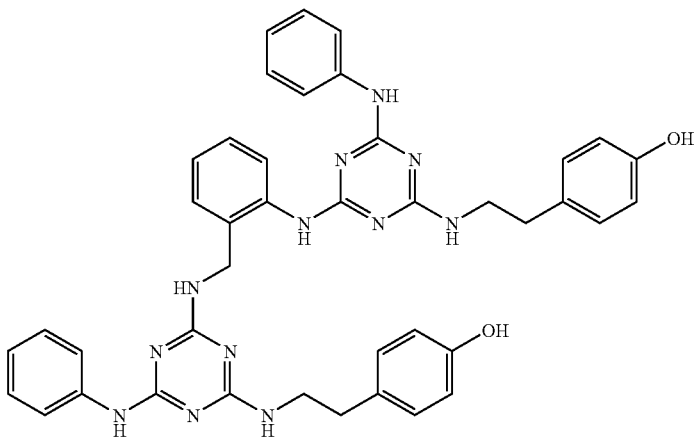 |

-continued
| Compound No. | Structure |
|---|---|
| 38 | 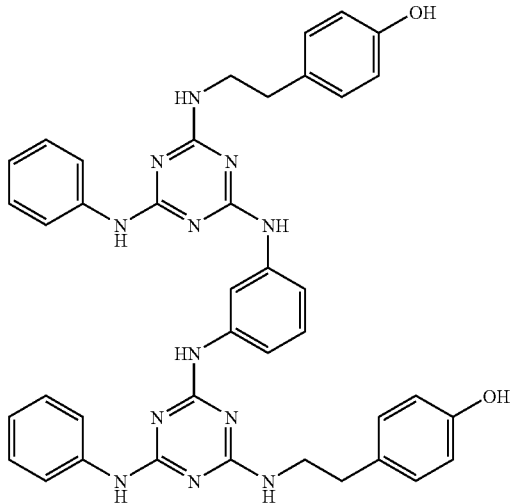 |
| 39 | 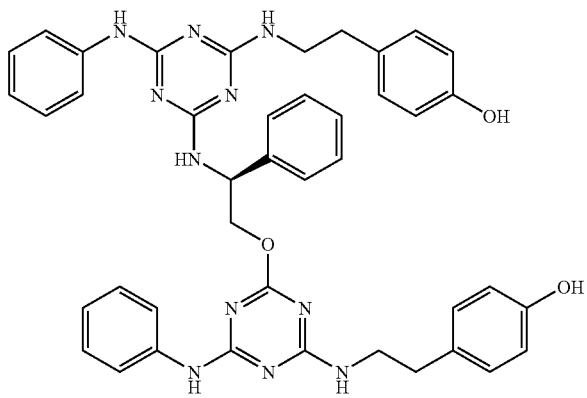 |
| 40 | 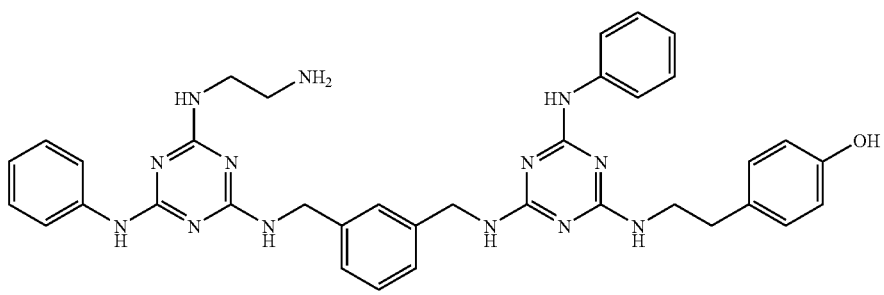 |
| 41 | 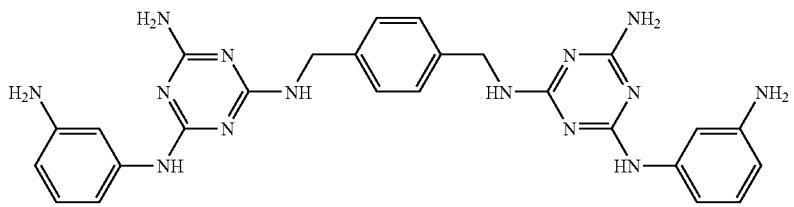 |

| Compound No. | Structure |
|---|---|
| 42 | 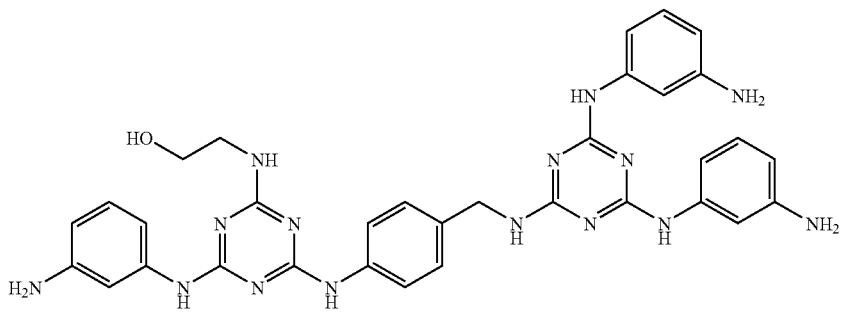 |
| 43 | 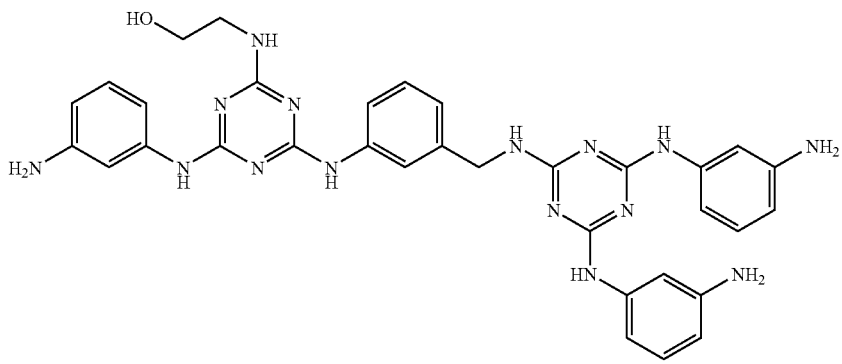 |
| 44 | 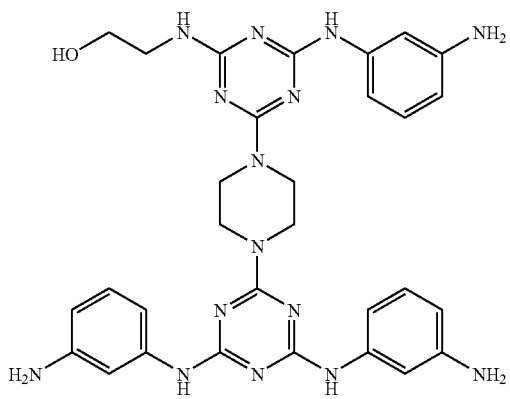 |
| 45 | 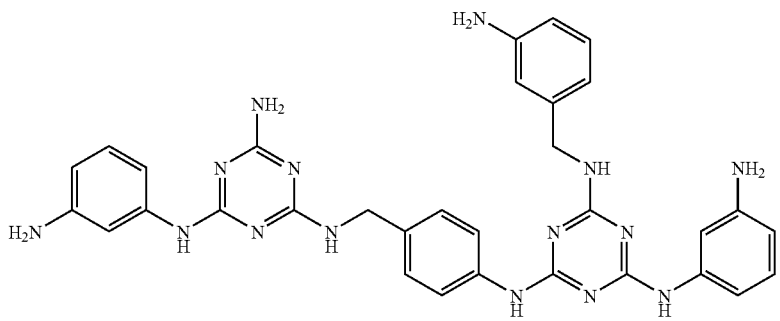 |

-continued
| Compound No. | Structure |
|---|---|
| 46 | 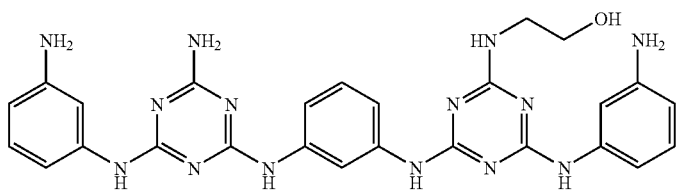 |
| 47 | 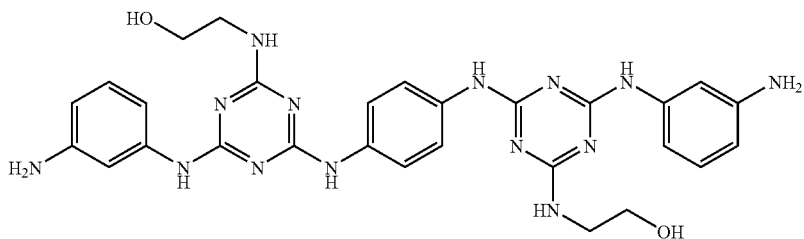 |
| 48 | 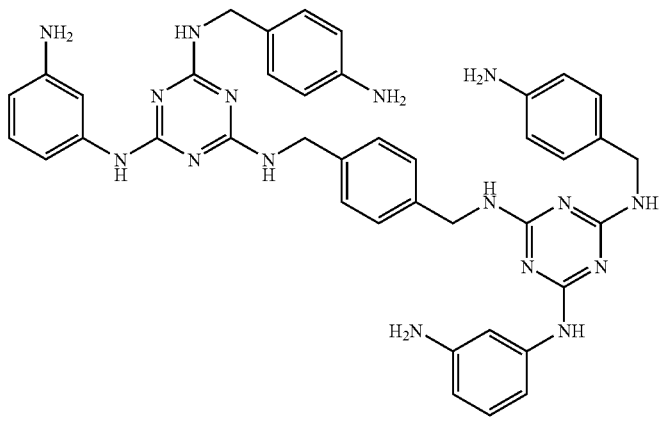 |
| 49 | 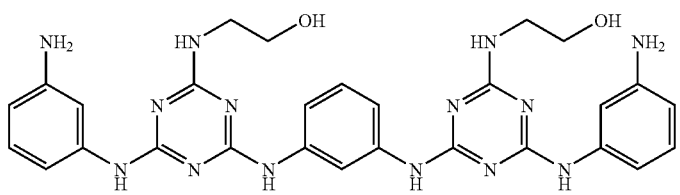 |
| 50 | 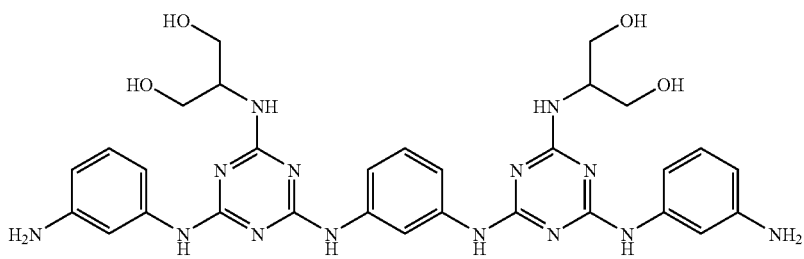 |
| 51 | 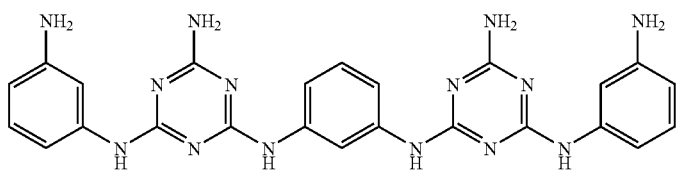 |

Compounds of the present invention may facilitate the clearance of immune complexes by phagocytosis or may limit the deposition of complexes within body organs and tissues by their ability to antagonize the binding of immune complexes to organ and tissue surfaces. The mechanism by which immune complexes attach to various surfaces can involve binding to cell surface Fc receptors, Fc receptors are glycoproteins of inflammatory leukocytes that bind the Fc (tail) portion of immunoglobulins. Fc receptors are also present on numerous tissues and provide a site for attachment and subsequent deposition of immune complexes onto tissue surfaces. For example, the deposition on kidney tissue of autoantibody containing complexes by binding to Fc receptors is thought to trigger an inflammatory response typical of SLE which can lead to glomerulonephritis. Well characterized Fc receptors include: FcγRI, FcγRII and FcγRIII (IgG receptors), FcεRI (the IgE receptor) and FcαRI (the IgA receptor). Interestingly, Staphylococcal protein A is a cell-surface bacterial protein which can bind to the Fc (tail) portion of most antibodies. For example, protein A will bind to human IgG1, IgG2 and IgG4 immunoglobulins. More importantly, it has been known for many years that protein A can inhibit the binding of IgG antibody containing immune complexes to Fc receptors. For example, A. Sulica et al. Immunology 38, 173-179 (1979) reported that protein A does inhibit IgG containing immune complex binding to Fc receptors but protein A enhances binding of IgG to lymphocytes and macrophages.

More recently, with the availability of Fc receptor (γchain) deficient mice, it became possible to establish the primary role of the IgG Fc receptors (FcγR) in mediating the effector responses seen in autoimmune diseases such as SLE and rheumatoid arthritis, as noted by M. Marino et al. Nature Biotechnology 18, 735-739 (2000). More specifically, these authors stated that agents which can interfere with the binding of immune complexes to FcγR should ameliorate SLE. They provided experimental support for this statement by treating a special strain of mice MRL/lpr) that develops a syndrome which is similar to human SLE with a peptide which binds to the Fc portion of IgG. The survival rate of treated animals (80%) was significantly greater than untreated animals (10%). In a recent review article by P. M. Hogarth Current Opinion Immunology 14, 798-802 (2002), it is stated that FcγR acts early in the inflammation process and engagement by immune complexes is a potent signal for the release of proinflammatory cytokines such as TNFα. In those cases where compounds of the present invention affect some aspect of immune complex clearance or deposition, they may do so by their ability to mimic protein A. That is, such compounds can bind to the Fc portion of human IgG as ascertained by their ability to inhibit the binding of protein A to human IgG, as determined in vitro by competitive ELISA. By binding to the Fc portion of human IgG in a fashion similar to protein A, such protein A mimic compounds may disrupt the binding of IgG containing immune complexes to FcγR. Subsequently, this should prevent deposition of immune complexes and thereby facilitate their clearance as well as diminish the release of proinflammatory cytokines.

Additionally, or alternatively, compounds of the present invention may inhibit the proinflammatory activity of TNFα. Unlike currently approved recombinant anti-TNFα TNFα monoclonal antibodies (Remicade, Humira) or soluble TNFα receptor (Enbrel), compounds of the present invention do not inhibit the binding of TNFα to the p55 TNFα receptor (CD120a) or the p75 TNFα receptor (CD120b). Nonetheless, compounds of the present invention may inhibit the effect of TNFα as ascertained by their ability to inhibit TNFα induced apoptosis/cytotoxicity in the WEHI 164 (13var) murine cell line. Additionally, compounds of the present invention may inhibit the production of TNFα as ascertained by their ability to inhibit LPS induced production of TNFα in the J774A-1 murine cell line.

TNFα is produced by many cell types which include fibroblasts and numerous immune cell subsets. Examples of the latter include macrophages, monocytes, B and T cells and mast cells. It is a pleiotropic molecule produced in response to a variety of stimuli and which can exert effects on most cell types. Under normal circumstances, low levels of serum TNFα confer protection against pathogens, tumors and tissue damage. Therefore, in terms of chronic or continued use of compounds of the present invention as therapeutic agents, one aspect of this invention may be that these compounds are not potent inhibitors of the effects or production of TNFα, nor do they potently inhibit the binding of TNFα to its receptor. The potential for long-term use of compounds of this invention is demonstrated by the treatment of NZBW/F1 mice (another model for human SLE) with compounds for approximately one year without observation of any significant toxicity.

Similar to biologicals described above, other TNFα inhibitors display toxicity which limits long-term or chronic use. For example, thalidomide (N-phthalimidoglutarimide) is a synthetic anti-inflammatory drug which inhibits TNFα synthesis. But clinical trials for patients with rheumatoid arthritis have been mostly unsuccessful because of unacceptable toxicity. Severe side effects included somnolence, peripheral neuropathy and severe rash. Many drugs that are commonly used as immunosuppressants such as cyclosporin A and methotrexate show TNFα inhibitory properties but also cannot be used on a chronic bass because of their toxicity.

Indeed, the pivotal role played by TNFα in many autoimmune diseases, as evidenced by the therapeutic success of recently approved biologicals along with the lack of efficacious yet nontoxic drugs available for chronic treatment, has led to the investigation of a number of approaches for the inhibition of TNFα. Approaches have included the search for inhibitors of phosphodiesterase IV, agonists of adenosine, matrix metalloproteinase inhibitors (e.g., inhibitors of TACE) signal transduction inhibitors (e.g., p38 MAP kinase) and inhibitors of transcription factors (e.g., NFκB). Clearly then, a need exists for compounds which can efficaciously inhibit the effects of TNFα but which can be used on a long-term basis for the treatment of chronic autoimmune diseases.

The present invention provides novel compounds as defined by the general formula above which are useful for the treatment of chronic autoimmune disease. These compounds may facilitate the clearance of immune complexes by phagocytosis or may limit the deposition of immune complexes within body organs and tissues by their ability to antagonize the binding of immune complexes to organ and tissue surfaces. In this case, such compounds may be particularly useful for the treatment of those autoimmune diseases where immune complexes play an important role in disease pathology: e.g., Neuritis, SLE, ITP, glomerulonephritis and vasculitis. Alternatively, the compounds of this invention may inhibit the proinflammatory actions of TNFα. In this case, such compounds may be particularly useful for the treatment of autoimmune diseases where inhibition of biological activity of TNFα is important to disease pathology: e.g., arthritis, psoriatic arthritis, psoriasis, Crohn's disease, inflammatory bowel disease, ankylosing spondylitis, Sjögren's syndrome, Still's disease (macrophage activation syndrome), uveitis, scleroderma, myositis, Reiter's syndrome and Wegener's syndrome. In a preferred embodiment of this invention, these compounds may mimic the activity of bacterial protein A thereby facilitating the clearance of immune complexes and inhibit the biological activity and subsequent effect of TNFα. In any case, it is not intended that the scope of the present invention be limited by the mechanism by which an improvement in any inflammatory condition indicative of an autoimmune disease occurs. Indeed, an improvement in an autoimmune condition may occur by use of compounds of this invention by a poorly defined or unknown mechanism, but said improvement being determined by in vivo activity displayed in an appropriate animal model. Therefore, the mechanism(s) by which compound efficacy occurs is not an important nor limiting aspect of this invention. Important, however, is the fact the compounds of this invention exhibit limited toxicity such that they may be administered accordingly for the treatment of chronic autoimmune disease.

Compounds of the present invention include all pharmaceutically acceptable derivatives, such as salts and prodrug forms thereof, and analogues as well as any geometrical isomers or enantiomers. Formulations of the active compound may be prepared so as to provide a pharmaceutical composition in a form suitable for enteral, mucosal (including sublingual, pulmonary and rectal), parenteral (including intramuscular, intradermal, subcutaneous and intravenous) or topical (including ointments, creams or lotions) administration. In particular, compounds of the present invention may be solubilized in an alcohol or polyol solvent (e.g., solutol HS 15 (polyethylene glycol 660 hydroxystearate from BASF), glycerol, ethanol, etc.) or any other biocompatible solvent such as dimethyl sulfoxide (DMSO) or cremophor EL (also from BASF). The formulation may, where appropriate, be conveniently presented in discrete dosage units and may be prepared by any of the methods well-known in the art of pharmaceutical formulation. All methods include the step of bringing together the active pharmaceutical ingredient with liquid carriers or finely divided solid carriers or both as the need dictates. When appropriate, the above-described formulations may be adapted so as to provide sustained release of the active pharmaceutical ingredient. Sustained release formulations well-known to the art include the use of a bolus injection, continuous infusion, biocompatible polymers or liposomes.

Suitable choices in amounts and timing of doses, formulation, and routes of ministration can be made with the goals of achieving a favorable response in the mammal (i.e., efficacy), and avoiding undue toxicity or other harm thereto (i.e., safety). Therefore, "effective" refers to such choices that involve routine manipulation of conditions to achieve a desired effect: e.g., reducing or otherwise ameliorating tissue injury associated with an immune response to body constituents (organs and tissues like adrenal, eye, joint, kidney, liver, lung, pancreas, nervous system, skin, thyroid etc.); restoring the immunological status or normalizing a pathological disorder/condition of the mammal (antibody titer, immune cell subsets, signaling by cytokines or chemokines, antibody-antigen immune complexes etc.); removal of free antibodies and/or antibody-antigen immune complexes from the circulation; laboratory indicia of autoimmune disease (concentration or absolute amount of soluble mediators of inflammation, presence of autoantibodies, cellular proliferation etc.); and combinations thereof. In particular, deleterious effects of conventional anti-TNFα treatment may be avoided.

The amount of compound administered is dependent upon factors such as, for example, bioactivity and bioavailability of the compound (e.g., half-life in the body, stability, and metabolism); chemical properties of the compound (e.g., molecular weight, hydrophobicity, and solubility); route and scheduling of administration; and the like. It will also be understood that the specific dose level to be achieved for any particular patient may depend on a variety of factors, including age, health, medical history, weight, combination with one or more other drugs, and severity of disease.

The term "treatment" refers to, inter alia, reducing or alleviating one or more symptoms of autoimmune disease in a mammal (e.g., human) affected by disease or at risk for developing disease. For a given patient, improvement in a symptom, its worsening, regression, or progression may be determined by an objective or subjective measure. Treatment may also involve combination with other existing modes of treatment and agents (e.g., anti-inflammatory drugs, agents binding TNFα like antibody or soluble receptor, NSAIDs, corticosteroids, DMARDs). Thus, combination treatment may be practiced. In such embodiments, it is preferred that toxicity of chronic treatment or the additional agent is at least reduced or avoided by reducing the amount or concentration of the additional agent used in comparison to treatment without a compound of the present invention.

It will be appreciated by those skilled in the art that the reference herein to treatment extends to prophylaxis as well as therapy of established or chronic autoimmune disease. It will be further appreciated that the amount of a compound of the invention required for treatment will vary not only with the particular compound used for treatment but also with the route of administration, the nature of the autoimmune condition being treated and the age and general health of the patient. The dose to be administered will ultimately be at the discretion of the physician. In general, however, the dose will be in the range from about 0.1 mg/kg to about 200 mg/kg of body weight per day. Preferably, doses will range from about 1 mg/kg to about 100 mg/kg of body weight per day. More preferably, the range will be between 2 mg/kg to 50 mg/kg of body weight per day.

Finally, and where appropriate, compounds of the present invention may be used in combination with other treatments for autoimmune disease well-known to the art. Other prior art treatments include those described above as represented by nonsteroidal anti-inflammatory drags (NSAIDs) (e.g., ibuprofen, aspirin, naproxen, etodolac and ketoprofen); corticosteroids (e.g., hydrocortisone, prednisone and dexamethasone); disease-modifying anti-rheumatic drugs (DMARDs) (e.g., cytotoxic drugs like methotrexate or azathioprine, immunosuppressants like cyclosporin or FK506, hydrochloroquine, organogold salts) and biological. The individual components of such combinations may be administered either sequentially or simultaneously in separate or combined pharmaceutical formulations. Alternatively, new pharmaceutical formulations may be created to accommodate the combination of compounds of this invention with conventional treatments for autoimmune disease.

Compounds of the present invention may also be used as affinity agents to bind antibody (e.g., human isotypes like IgM, IgD, IgA1, IgA2, IgE, IgG1, IgG2, IgG3, and/or IgG4) in vitro or ex vivo. Free (i.e., not bound to antigen) antibody and/or antibody-antigen immune complex may be specifically bound by such affinity agents. Large affinity complexes may be isolated by selective precipitation or differential centrifugation, or identified by flocculation assays. But it is preferred to immobilize one or more compounds to an insoluble support material (e.g., agarose, dextran, cellulose, polyacrylamide, other polymeric materials, silica and glass) preferably covalently linked directly or indirectly by a linker. A compound of the present invention may be synthesized in situ on the support or through an activated organic linker. Optionally, the linker may be cleavable (e.g., by a reducing agent or site-specific protease) such that the compound (with or without bound antibody) may be detached from the support. For example, one or more compounds of the present invention may be covalently inked to a support in the form of a glass slide, multiwell plate, optical fiber, protein chip or test tube for assays and analysis; tissue culture dish for incubating cells or antigen; and magnetic beads, porous membrane or chromatographic media for separation. Antibody or other Fc containing material may be bound to one or more compounds of the present invention (i.e., isolation), and then optionally separated from unbound material (with or without washing and multiple rounds of binding under different conditions) to purify Fc containing material. For example, ionic strength (e.g., salt concentration) or pH may change binding conditions and be used to release Fc containing material.

Free antibody and/or immune complexes may be isolated for clinical laboratory diagnosis. Apheresis using standard or fluidized bed chromatography may be used to remove free antibody and/or immune complexes from the circulation: a physiological fluid (e.g., blood) is incubated with insoluble support material on which one or more compounds of the present invention are attached, at least some antibody material is bound to the compound(s) and immobilized on the support, bound antibody is separated from the rest of the physiological fluid, and at least some of the remaining (soluble) components of the physiological fluid is returned to the mammal from whom it was obtained. It is convenient to package the device containing one or more compounds of the invention for apheresis (e.g., a column) under aseptic conditions and to replace it after every use.

Antibody may be isolated from a composition and then optionally separated to any desired degree of purification. An antibody containing composition is incubated with insoluble support material on which one or more compounds of the present invention are attached, and at least some antibody material is bound to the compound(s) and mobilized on the support. Bound antibody may be separated from the remainder of the composition and that remainder is depleted of total antibody or that fraction of antibody which binds (e.g., one or more isotypes). Isolated antibody on the support may be released by washing or cleaving the linker. Either enriched antibody or the components of the depleted composition or both is the desired product. It is convenient to repeat binding and washing under different incubation conditions to increase the efficiency of isolation and separation.

Therefore, in another embodiment of the present invention, a device or kit is provided for use in the methods described above. For example, it may be used to bind antibody, for isolation of antibody, to remove antibody from a composition or the circulation, for separation of antibody, and to purify antibody from a source material or other composition. The product may be packaged aseptically under pharmaceutically acceptable conditions or stored under sterile conditions for the clinical laboratory. One or more compounds of the present invention are attached to an insoluble support material and packaged in a device (e.g., column) or kit with one or more optional components: storage buffer, binding and washing solutions, and an agent to cleave compounds from the support.

EXAMPLES

The following examples further illustrate the practice of this invention but are not intended to be limiting thereof.

The general synthetic sequence for preparation of the compounds useful in the present invention is outlined in schemes I and II. Scheme I illustrates the synthetic route employed for compounds described in this invention except those compounds belonging to Group 2. Also, scheme II demonstrates the synthetic method used for compounds described in this invention except those compounds belonging to Group 1.

SCHEME 1

Method A

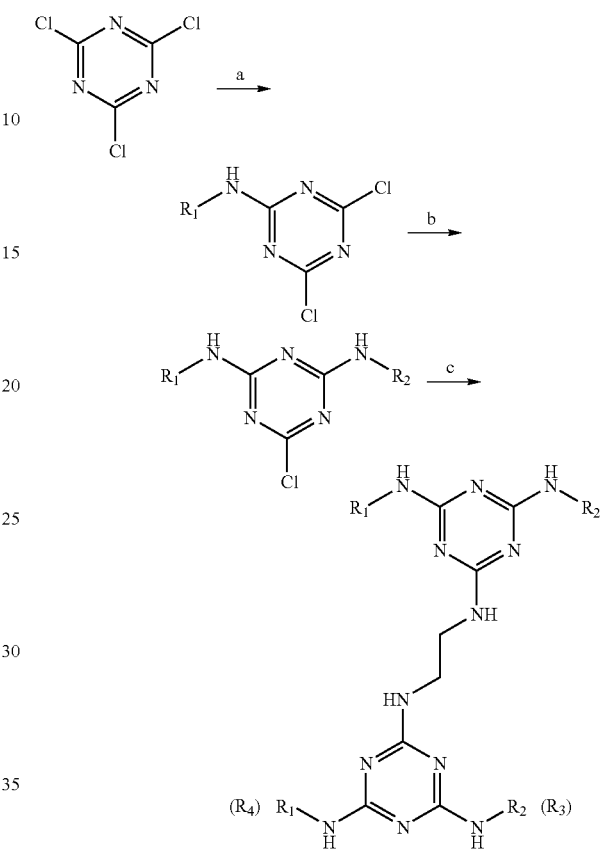

Method B

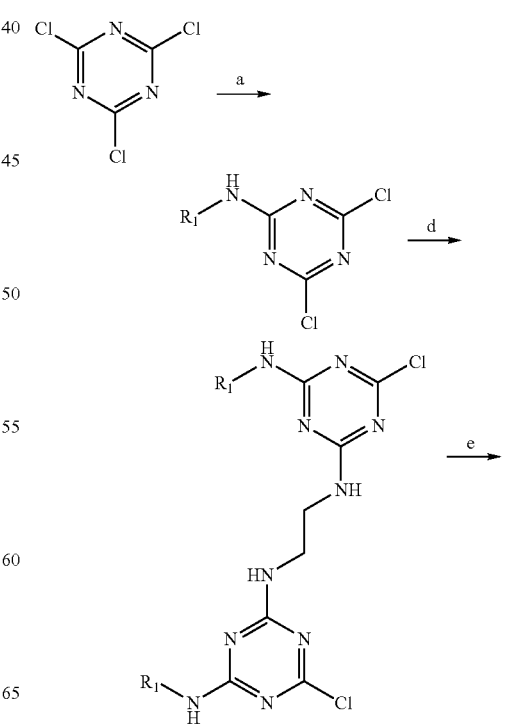

-continued

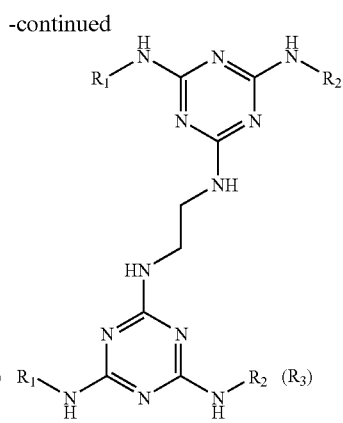

$R_1$, $R_2$, $R_3$ and $R_4$ are defined as above.

Reagents: (a) aniline or other arylamine, aq. NaHCO$_3$, acetone/H$_2$O, 0° C.; (b) 2-(4-hydroxyphenyl)ethylamine or other aralkylamine, aq. NaHCO$_3$, THF/acetone/H$_2$O, room temperature; (c) ethylenediamine, DIEA, THF, 60° C.; (d) ethylenediamine, aq. NaHCO$_3$, THF/acetone/H$_2$O, room temperature; (e) 2-(4-hydroxyphenyl)ethylamine or 2-(4-hydroxyphenyl)ethylamine derivatives, Et$_3$N, THF, 60° C.

SCHEME 2

Method A

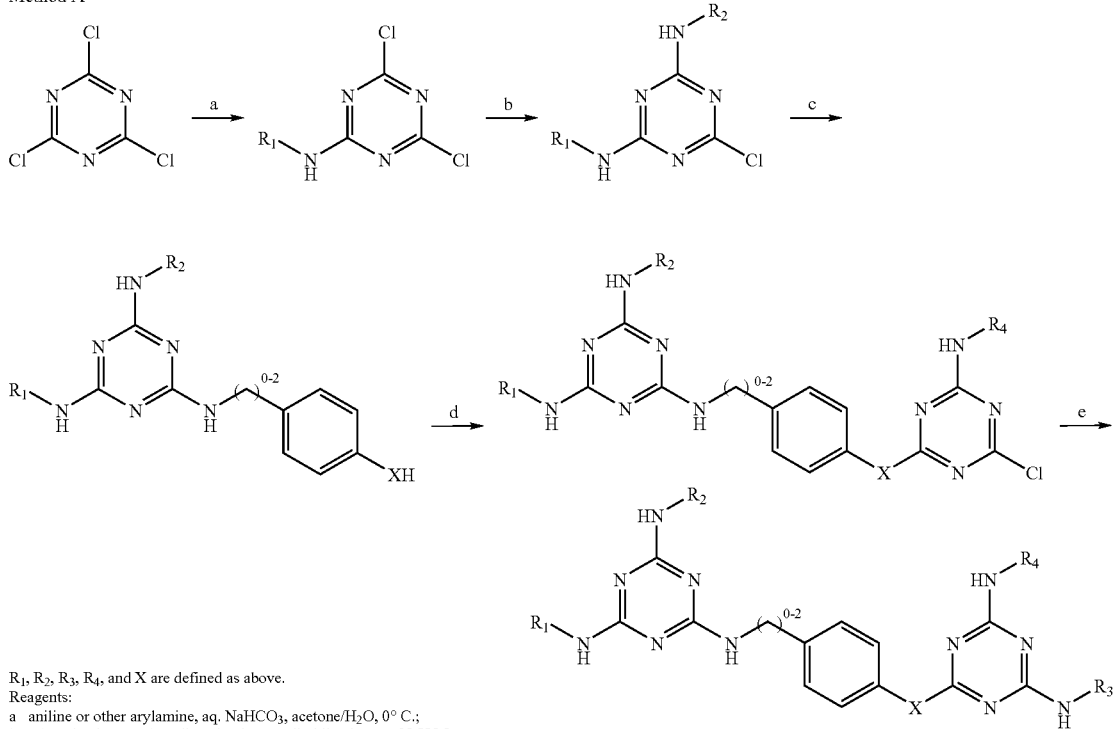

$R_1$, $R_2$, $R_3$, $R_4$, and X are defined as above.
Reagents:
a  aniline or other arylamine, aq. NaHCO$_3$, acetone/H$_2$O, 0° C.;
b  ethanolamine or other alkanolamine, or alkyldiamine, aq. NaHCO$_3$, THF/acetone/H$_2$O, room temperature;

c  H$_2$N—(CH$_2$)$_{0-2}$—[phenyl]—XH,  Et$_3$N, THF, 50° C.;

d  [dichlorotriazine with R$_4$-NH], NaHCO$_3$, THF/acetone/H$_2$O, room temperature or NaH/THF;

e  R$_3$—NH$_2$,  Et$_3$N, THF, 50° C.

Method B (Solid Phase Synthesis)
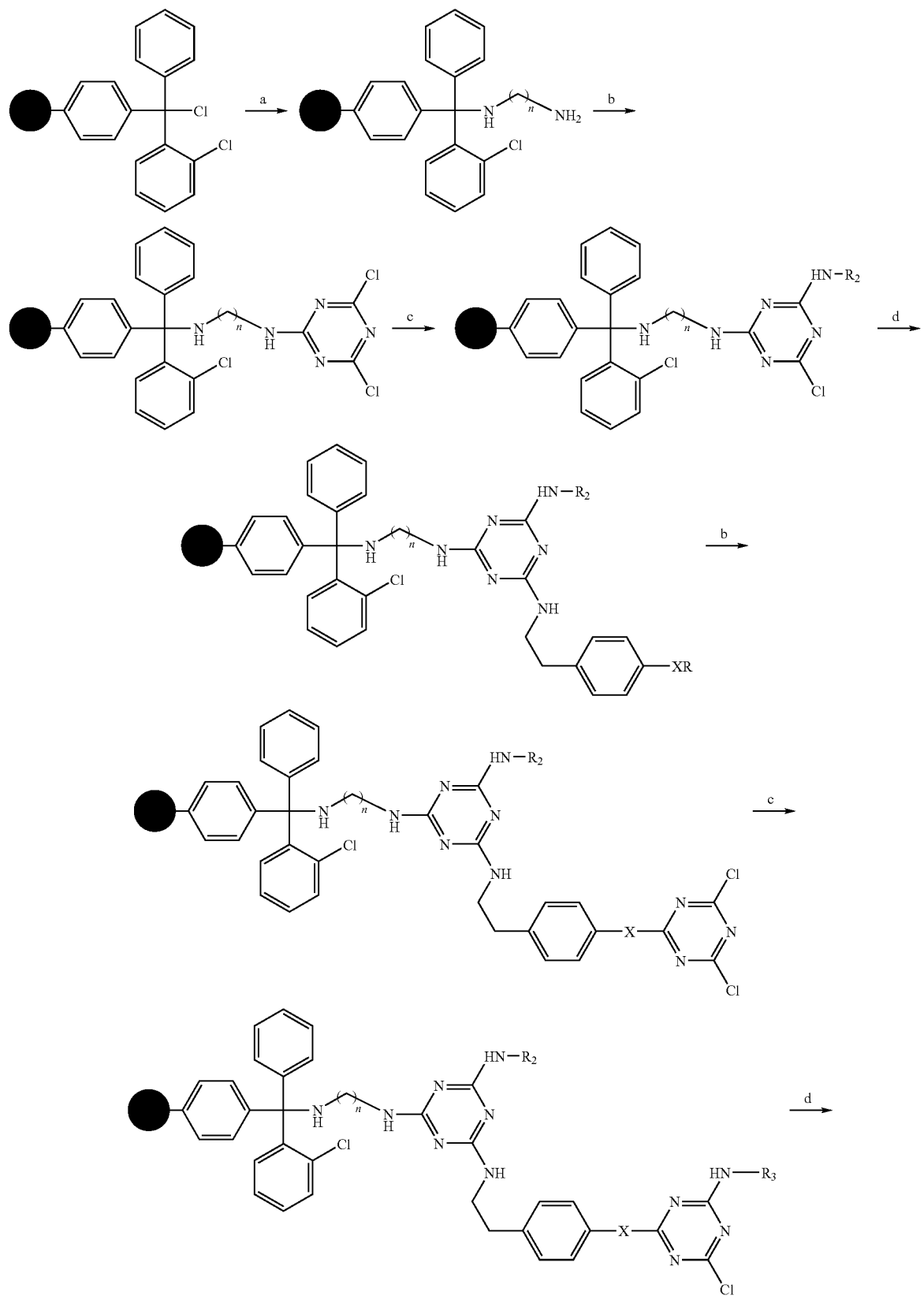

-continued

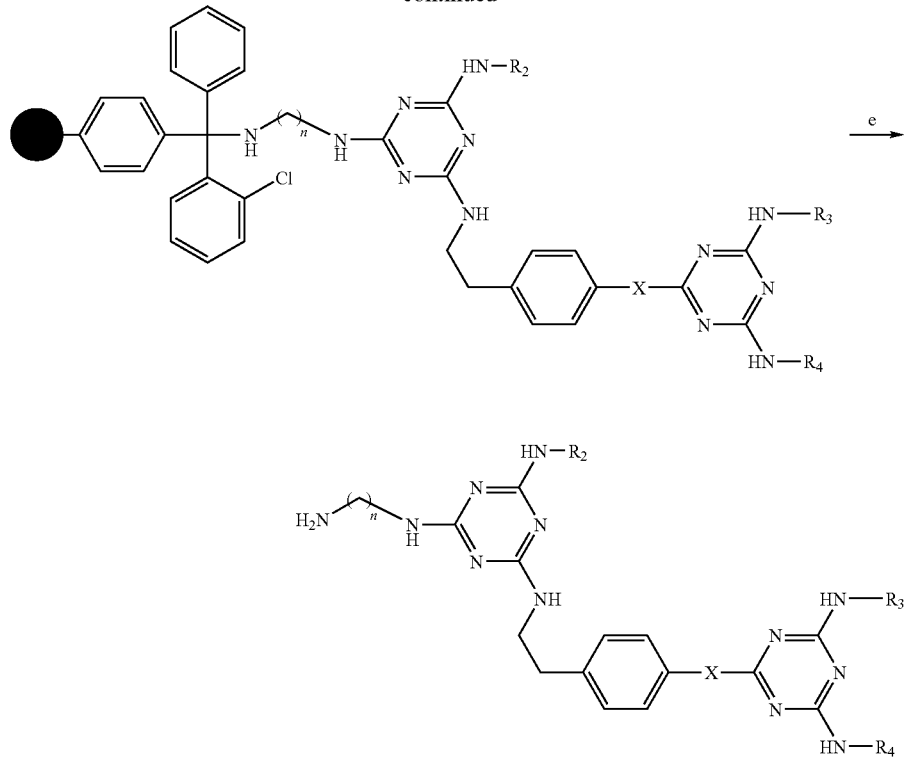

n = 2-6, X ia defined as above
Reagents:
a 1) amine, DCE, RT, 17.5 h, 400 rpm; 2) methanol, DIEA, RT, 1 h, 400 rpm;
b cyanuric chloride, DIEA, THF, room temperature, 30 min, 400 rpm;
c 1) for aliphatic amines: amine, DIEA, NMP, room temperature, 20 h, 400 rpm; 2) for aromatic amines: amine, DIEA, NMP, 50° C., 24 h, 400 rpm;
d amine, DIEA, NMP, 80° C., 20 h, 400 rpm;
e 5% trifluoroacetic acid/dichloroethane, room temperature, 1 h, 400 rpm.

Instrumentation

All HPLC chromatograms and mass spectra were recorded on a HP 1100 LC-MS Agilent instrument using a diode array defector. An analytical C18 column (250×4.6 mm, 5 microns) with a gradient of 10-70% acetonitrile-water containing 0.01% TFA in 10 min and a flow of 1 mL/min (method 1) or an analytical C18 column (75×4.6 mm, 5 microns) with a gradient of 10 to 99% acetonitrile-water containing 0.01% TFA in 10 min and a flow of 1 mL/min (method 2) or an analytical C18 column (75×4.6 mm, 5 microns) with a gradient of 15-99% acetonitrile-water containing 0.01% TFA in 6 min and a flow of 2 mL/min (method 3) or an analytical C18 column (75×4.6 mm, 5 microns) with a gradient of 10-40% acetonitrile-water containing 0.01% TFA in 6 min and a flow of 2 mL/min (method 4) or an analytical C18 column (75×4.6 mm, 5 microns) with a gradient of 1-20% acetonitrile-water containing 0.01% TFA in 6 min and a flow of 2 mL/min (method 5).

Example 1

Representative Example of Scheme I Method A: Synthesis of Compound 1

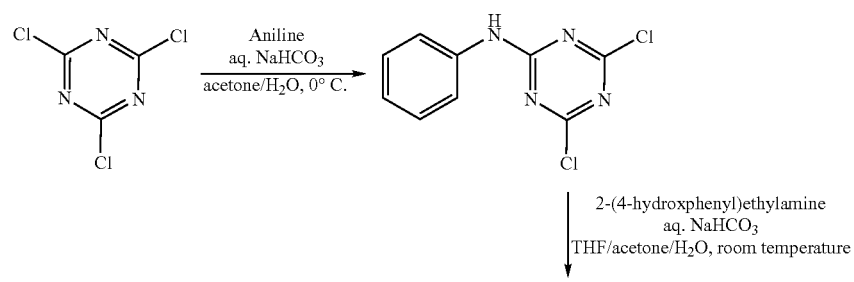

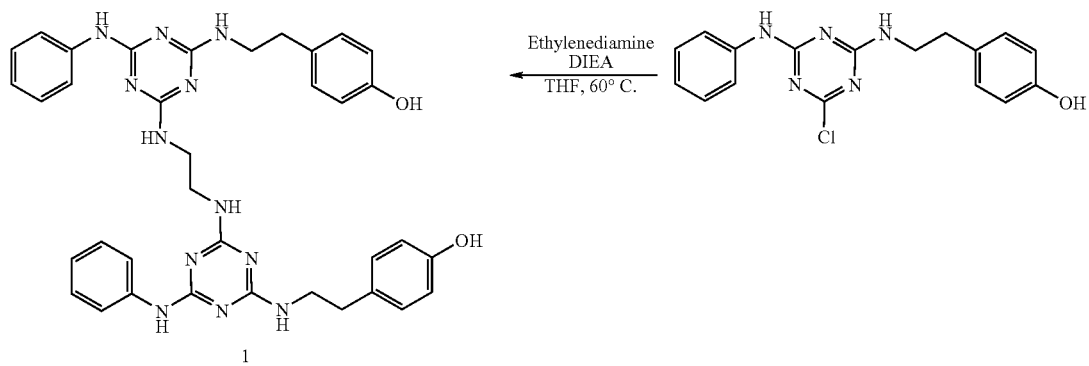

To a suspension of cyanuric chloride (20 g, 108 mmol) in acetone (120 mL) and ice (50 mL) at 0° C. was added dropwise a solution of aniline (10 g, 107 mmol) in acetone (45 mL). At the end of the addition, the pH of the solution was adjusted from 1 to 7 with 5% aqueous sodium bicarbonate (150 mL). The precipitate was filtered, washed several times with water and dried in vacuo. This gave 2,4-dichloro-6-phenylamino-1,3,5-triazine as an off-white solid (24.3 g, 93% yield). The product was used in the next step without further purification. To a solution of the dichlorotriazine (6.2 g, 25.7 mmol) in THF (300 mL) at room temperature was added a solution of 2-(4-hydroxyphenyl)ethylamine (3.6 g, 25.9 mmol) in acetone (100 mL) and water (100 mL), followed by 5% aqueous sodium bicarbonate (50 mL). After 20 h reaction at room temperature, the solution was diluted with water (50 mL) and ethyl acetate (50 mL). The aqueous layer was extracted with ethyl acetate (2×50 mL). The organic layers were washed with brine (150 mL), dried over anhydrous sodium sulphate, filtered and evaporated to dryness. This gave 2-chloro-4-(2-[4-hydroxyphenyl]ethylamino)-6-phenylamino-1,3,5-triazine as an off-white solid (8.5 g, 97% yield). The product was used for the next step without further purification. This triazine derivative (384 mg, 1.1 mmol) was dissolved in THF (11 mL) at room temperature. To this solution was added ethylenediamine (68 µL, 1.0 mmol) followed by diisopropylethylamine (355 µL, 2.0 mmol). After 20 h at 50° C., the solution was diluted with methanol (10 mL) and concentrated under reduced pressure. The crude residue was purified on a Biotage™ 25S column (silica, hexane/AcOEt 9:1 to 0:1) to yield compound 1 as a white solid. Yield of product: 267 mg (78%); $^1$H NMR (300 MHz, CD$_3$OD) δ 7.63 (m, 4H), 7.21 (t, 4H, J=7.6 Hz), 6.98 (m, 6H), 6.68 (d, 4H, J=7.9 Hz), 3.48 (m, 8H), 2.84 (m, 4H); LRMS (FAB+): m/z 672.0 (MH$^+$); HRMS: Calc. for MH+ C$_{36}$H$_{39}$N$_{12}$O$_2$, 671.33191; found 671.33060; HPLC (method 1): 8.0 min.

Example 2

A Representative Example of Scheme II Method A: Synthesis of Compound 17

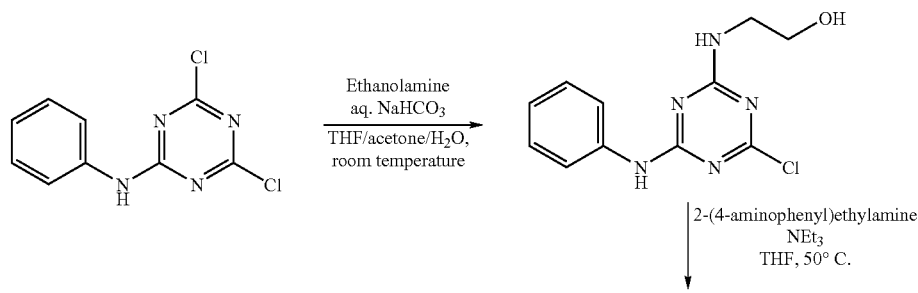

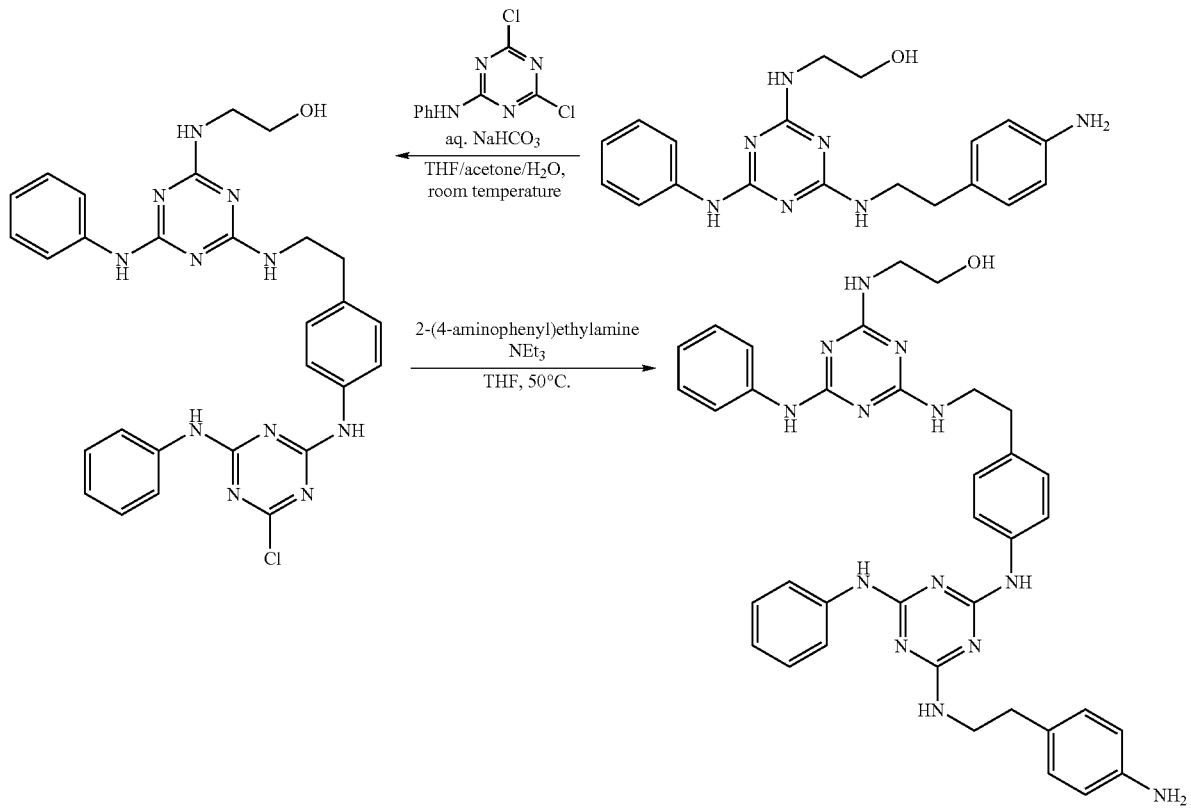

To a solution of 2,4-dichloro-6-aminophenyl-1,3,5-triazine (1.6 g, 6.6 mmol) in THF (70 mL) at room temperature was added a solution of ethanolamine (439 mg, 7.3 mmol) in acetone (24 mL) and water (24 mL), followed by 5% aqueous sodium bicarbonate (15 mL). The reaction was stirred for 20 h at room temperature. The mixture was then diluted with water (25 mL) and ethyl acetate (25 mL). The aqueous layer was extracted with ethyl acetate (2×25 mL). The organic layer was washed with brine (50 mL), dried over anhydrous sodium sulphate, filtered and concentrated under reduced pressure. The crude residue was purified on a Biotage™ 40S column (silica, hexane/AcOEt 9:1 to 0:1) to yield 2-chloro-4-(2-hydroxyethylamino)-6-aminophenyl-1,3,5-triazine as a white solid (1.6 g, 91% yield). This compound (710 mg, 2.7 mmol) was dissolved in THF (26 mL) and 2-(4-aminophenyl)ethylamine (1.1 mL, 8.0 mmol) was added followed by triethylamine (1.1 mL, 8.0 mmol). The reaction was stirred for 20 h at 60° C. and then diluted with methanol (20 mL). Solvent was removed under reduced pressure and the crude residue was purified on a Biotage™ 40S column (silica, AcOEt/MeOH 1:0 to 9:1) to yield 2-[2-(4-aminophenyl)ethylamino]-4-(2-hydroxyethylamino)-6-phenylamino-1,3,5-triazine as an off-white solid (916 mg, 91% yield). To a solution of 2,4-dichloro-6-aminophenyl-1,3,5-triazine (356 mg, 1.5 mmol) in THF (30 mL)/acetone (11 mL)/water (11 mL) was added a solution of 1,3,5-triazine derivative above (540 mg, 1.5 mmol) in THF (14 mL) followed by 5% sodium bicarbonate, solution (10 mL). The reaction was stirred for 20 h at room temperature and the solution diluted with water (30 mL) and ethyl acetate (30 mL). The aqueous layer was extracted with ethyl acetate (30 mL). The organic layers were washed with brine (40 mL), dried over anhydrous sodium sulphate and filtered. This gave 2-{4-[2-(4-{4-chloro-6-phenylamino-[1,3,5]triazin-2-ylamino}phenyl)-ethylamino]-6-phenylamino-[1,3,5]triazin-2-ylamino}-ethanol as an off-white solid (860 mg, quantitative yield). The product was used for the next step without further purification. To a solution of this compound (41 mg, 0.1 mmol) in THF (1 mL) was added 2-(4-aminophenyl)ethylamine (28 μL, 0.2 mmol) followed by triethylamine (30 μL, 0.2 mmol). After 20 h of reaction at 50° C., the solution was diluted with methanol (5 mL) and concentrated under reduced pressure. The crude residue was purified on a Biotage™ 12 M column (silica, AcOEt/MeOH 1:0 to 9:1) to yield compound 17 as a white solid. Yield of product: 30 mg (79%), $^1$H NMR (400 MHz, CD$_3$OD) δ7.63-7.39 (m, 6H), 7.14 (m, 4H), 7.04 (d, 2H, J=8.6; H), 6.86 (m, 4H), 6.56 (d, 2H, J=7.8 Hz), 3.59 (m, 2H), 3.43 (m, 6H), 2.75 (m, 2H), 2.66 (t, 2H, J=7.5 Hz); LRMS (ESI): m/z 670.2 (MH$^+$); HPLC (method 2): 4.3 min.

Example 3
A Representative Example of Scheme II Method B:
Solid Phase Synthesis of Compound 16
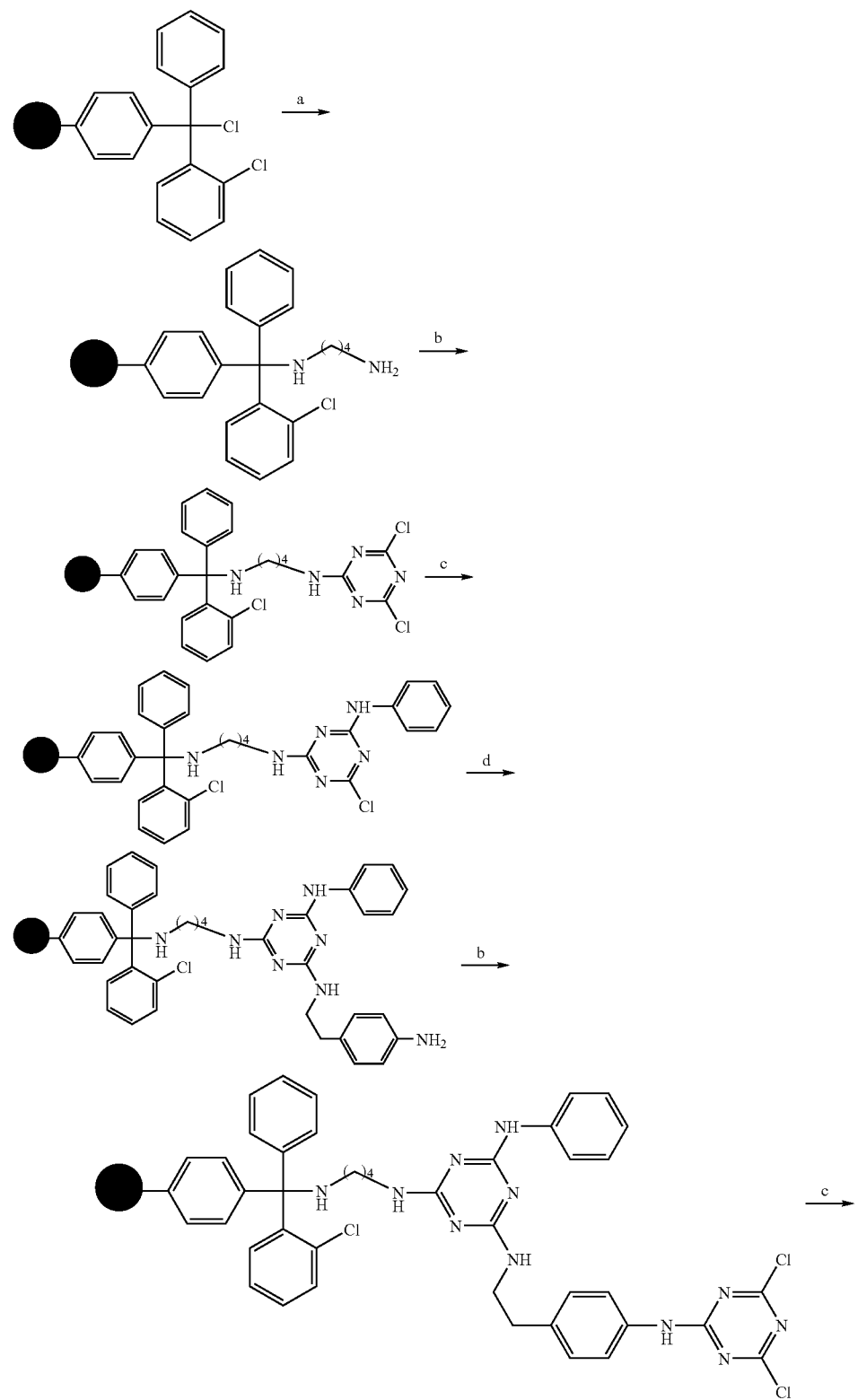

-continued

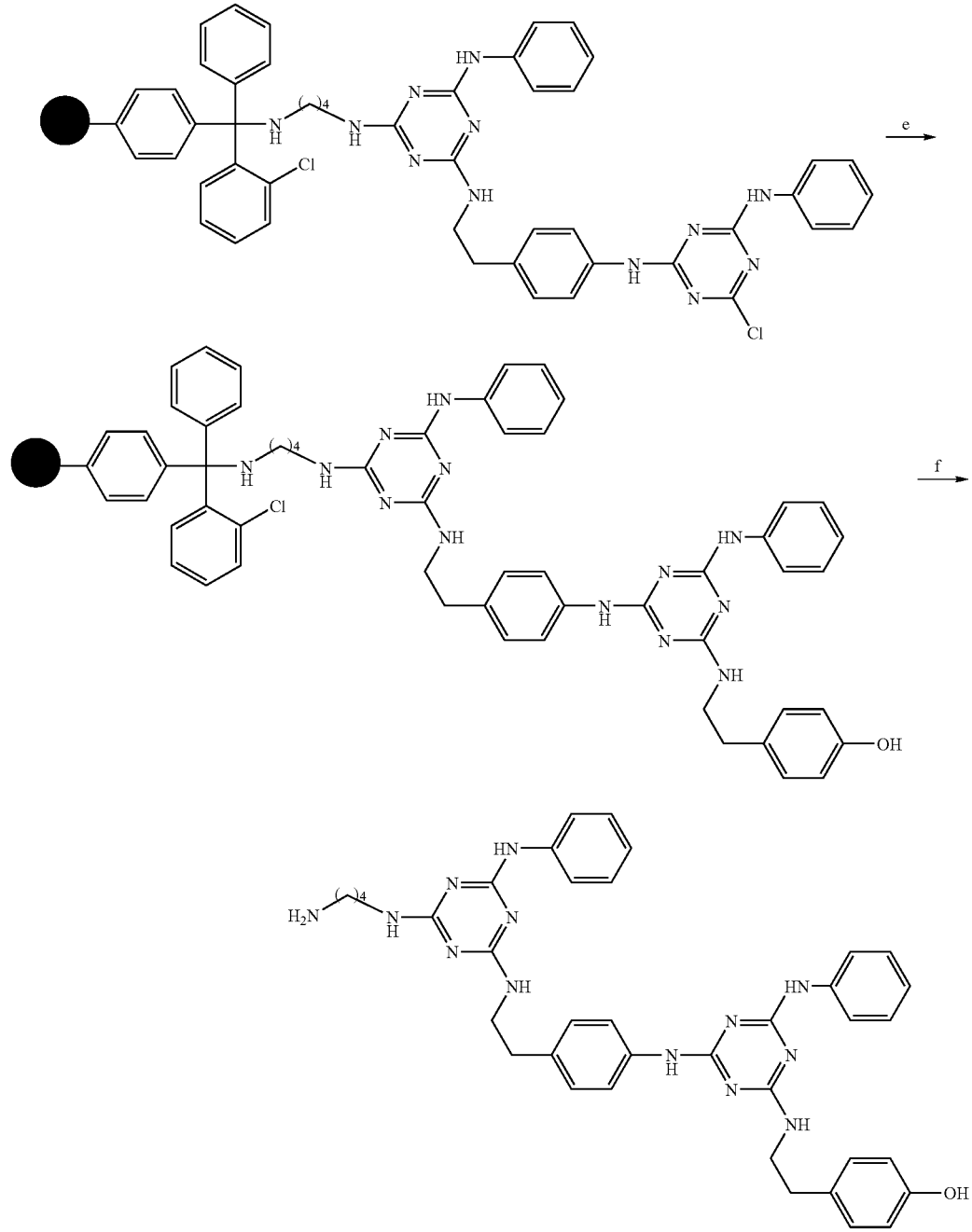

16

Reagents:
a 1) 1,4-diaminobutane, dichloromethane, 17.5 h, 400 rpm; 2) MeOH, DIEA, 25° C., 1 h, 400 rpm;
b cyanuric chloride, DIEA, THF, 25° C., 30 min., 400 rpm;
c aniline, DIEA, NMP, 50° C., 24 h, 400 rpm;
d 2-(4-aminophenyl)ethyamine, NMP, 80° C., 20 h 400 rpm;
e 2-(4-hydroxyphenyl)ethyamine, DIEA, NMP, 80° C., 20 h, 400 rpm;
f 5% trifluoroacetic acid/dichloroethane, 25° C., 1 h, 400 rpm.

Instrumentation

The solid phase synthesis was performed in Bohdan Miniblocks. They were in sets of two, possessing forty-eight polypropylene reaction tubes. Each tube had a frit at the bottom for filtration of the solid support. A screw acting as a valve allows (or not) the flow of liquids. A heat transfer block surrounding all the tubes was added to provide appropriate heating of the reactions. The heat transfer blocks were coupled to a Julabo FP 40 refrigerated heating circulator. The tubes were covered with a Teflon sheet, rubber septa and closed with the top of the block that contains clips to keep them tightly closed. The blocks were agitated on a modified Innova shaker from New Brunswick Scientific. For evaporation, a Genevac HT-4II was used Attachment of 1,4-Diaminobutane to the 2-Chlorotrityl Resin for Solid Phase Synthesis In a vial (4.0 mL) was placed resin (53.0 mg, 1.9 mmol) followed by dichloromethane (1.5 mL) and THF (0.5 mL). This mixture was homogenized by use of an automatic pipette. From this mixture, 2.0 mL were placed in the well in a block. By opening the valve, the resin was filtered from the solvent. Dichloromethane (1.0 mL) was then added to wash the resin in each well. The valve was closed and 1,4-diaminobutane (41 mg, 0.47 mmol) in dichloromethane (2.0 mL) was added and the block was capped and placed on the shaker for 17.5 h at room temperature and 400 rpm. The blocks were then placed on the vacuum collection set, and the resin filtered by opening the valve. The resin was washed with N (2×), methanol (2×), water (3×), methanol (2×), dichloromethane (2×) and THF (1×) respectively.

First Addition of Cyanuric Chloride

The valve was closed and 1.0 mL of a solution of DIEA (68 µL, 0.5 mmol) in THF (1 mL) was then dispensed in the well. To this mixture was added 1 mL of a solution of cyanuric chloride (87 mg, 0.5 mmol) in THF (1.0 mL). The block were capped with a Teflon sheet and a rubber septum was placed on the shaker and agitated for 30 min at room temperature, 400 rpm. The block was removed from the shaker and placed on a vacuum collection base set. The valve was then opened to filter the resin. THF (1.0 mL) was added to wash the mixture. The valve was closed and more THF (1.0 mL) was added. The block was placed on a shaker for 5 min and the valve opened to filter the resin. After three washes with THF, a last wash with NMP was undertaken for the next reaction.

Addition of Aniline to Dichloro-1,3,5-Triazine

A solution of DIEA (82 µL 0.5 mmol) in NMP (1.0 mL) was prepared and placed in the well with the valve closed. To this mixture was added a solution of aniline (43 µL, 0.5 mmol) in NMP (1.0 mL). 1.0 ml of this solution was distributed in each well. The blocks were placed on the shaker and agitated for 17.5 h at 50° C. at 400 rpm. The blocks were cooled to 25° C. and removed from the shaker. The resin was then filtered and washed with NMP (5×) using the same procedure described above.

Addition of the Linker to Monochloro-1,3,5-Triazine

A solution of DIEA (82 µL, 0.5 mmol) in NMP (1.0 mL) was prepared and placed in the well with the valve closed. 2-(4-aminophenyl)ethylamine (52 µL, 0.4 mmol) was placed in a vial (4.0 mL) and NMP (1.0 mL) was added to give a solution. The blocks were placed on the shaker and agitated for 18.5 h at 80° C. at 400 rpm. After 18 h, the blocks were cooled to 25° C. and removed from the shaker. The resins were filtered and washed with NMP (5×), dichloromethane (1×), methanol (1×), dichloromethane (1×), methanol (1×) and dichloromethane (1×) according to the same procedure as described above. By closure of the valve, the blocks were ready for the next step.

Second Addition of Cyanuric Chloride

Same procedure as above.

Second Addition of Aniline to Dichloro-1,3,5-Triazine

A solution of DIEA (82 µL, 0.5 mmol) in NMP (1.0 mL) was prepared and placed in the well with the valve closed. Aniline (43 µL, 0.5 mmol) was placed in a vial (4.0 mL) and NMP (1.0 mL) was added The aniline solution was dispensed in the well. The blocks were placed on the shaker and agitated for 19 h at 50° C. at 400 rpm. The blocks were then cooled to 25° C., removed from the shaker and treated according to the same procedure as described previously. The resin was filtered and washed with NMP (5×). By closing the valve, the blocks were ready for the next step.

Second Addition of 2-(4-Hydroxyphenyl)Ethylamine to Monochloro-1,3,5-Triazine

A solution of DIEA (82 µL 0.5 mmol) in NMP (1.0 mL) was prepared and placed in the well with the valve closed. 2-(4 Hydroxyphenyl)ethylamine (65 mg, 0.5 mmol) was placed in the vial (4 mL) and NMP (1.0 mL) was added to yield a solution. The 2-(4-hydroxyphenyl)ethylamine solution (1 mL) was distributed in the well and the block was placed on the shaker and agitated for 23 h at 80° C. at 400 rpm. The block was cooled to 25° C., removed from the shaker and treated according to the same procedure as described previously. The resin was filtered and washed with NMP (5×), dichloromethane (1×), methanol (1×), dichloromethane (1×), methanol (1×) and dichloromethane (1×) respectively. By closing the valve, the blocks were ready for the next step.

Cleavage of the Resin

A solution of 5% trifluoroacetic acid in dichloroethane was prepared and 2 mL was added to the well. The blocks were capped, placed on the shaker and agitated for 1 h at room temperature at 400 rpm. Then, the blocks were placed on the vacuum collection base set. The resin was filtered into a clean 96 deep well plate #1. A new clean 96 deep well plate #2 was placed in vacuum collection set. Dichloroethane (1.0 mL) was then added in well, the valve closed and methanol (1.0 mL) was added. The blocks were agitated on the shaker for 5 min, and filtered into the deep well plate #2. A new clean 96 deep well plate #3 was placed in the vacuum collection set, and methanol (1.0 mL) was added to the well. The 96 deep well plates (1 and 2) were then evaporated in the Genevac apparatus. Plate #1 was analyzed by LC/MS. The plates were combined and placed in the Genevac apparatus and evaporated again. The plates were placed on the HPLC/Gilson for purification. Yellow solid; $^1$H NMR (400 MHz, CD$_3$OD): δ 7.64-6.67 (m, 18H), 3.65 (m, 4H), 3.48 (m, 2H), 2.99-2.79 (m, 6H), 1.72 (m, 4H); LRMS (ESI): m/z 698.2 (MH$^+$), 720.2 (M+Na); HPLC (method 2): 4.4 min.

Example 4

Synthesis of Compound 2

The above compound was prepared as in Example 1 starting with methyl anthranilate and 2-(4-hydroxyphenyl)ethylamine. White solid; $^1$H NMR (400 MHz, CD$_3$OD): δ 8.82-6.69 (m, 16H), 3.86 (s, 6H), 3.63-3.49 (m, 8H), 2.73 (s, 4H); LRMS (EST): m/z 787.2 MH$^+$); HPLC (method 1): 8.2 min.

Example 5

Synthesis of Compound 3

The above compound was prepared by modification of the procedure in Example 1. To a suspension of cyanuric chloride (4 g, 21.7 mmol) in acetone (25 mL) and ice (10 mL) at 0° C. was added dropwise a solution of 2-(4-hydroxyphenyl)ethylamine (2.9 g, 21.5 mmol) in THF (15 mL), acetone (10 mL) and water (10 mL). After the end of addition, the pH of the solution was brought from 3 to 7 with a 5% solution of sodium bicarbonate (40 mL). After 2 h of reaction at 0° C., the solution was diluted with water (10 mL) and ethyl acetate (20 mL). The two layers were separated and the aqueous layer was extracted with ethyl acetate (25 mL). The combined organic layers were washed with brine (25 mL), dried over magnesium sulfate, filtered and evaporated to dryness to give a light yellow solid (5.3 g, 86%). The product was used for the next step without further purification. To a solution of this dichlorotriazine (1.21 g, 4.2 mmol) in acetone (25 mL) at room temperature was added a solution of ammonia 0.5 M in dioxane (25 mL, 12.7 mmol) and the solution was then stirred at 50° C. in a sealed tube for 60 h. The solution was then concentrated under reduced pressure. The crude residue was first purified on a Biotage™ 40M column (silica, hexane/AcOEt 9:1 to 0:1) and then on a semi-preparative HPLC (C18 double-end capped column, 250×10 mm, 5 microns, $H_2O$/$CH_3CN$ containing 0.05% trifluoroacetic acid 7:3 to 1:9 over 20 min) to yield the chlorotriazine as a white solid (70 mg, 6%).

To a suspension of cyanuric chloride (3 g, 16.3 mmol) in acetone (30 mL) and ice (15 mL) at 0° C. was added dropwise a solution of methyl anthranilate (2.46 g, 16.3 mmol) in acetone (10 mL). At the end of the addition the pH of the solution was brought from 1 to 8.5 with a 5% solution of sodium bicarbonate. After 20 h of reaction at room temperature, the precipitate was filtered off, washed several times with water and dried in vacuo to give an off-white solid (4.51 g, 93%). The product was used for the next step without further purification. To a solution of this dichlorotriazine (2.0 g, 6.7 mmol) in THF (55 mL) at room temperature was added a solution of 2-(4-hydroxyphenyl)ethylamine hydroxyphenyl)ethylamine (918 mg, 6.7 mmol) in acetone (5 mL) and water (2 mL), followed by a 5% solution of sodium bicarbonate. After 5 h of reaction at 50° C., the solution was diluted with water and ethyl acetate. The aqueous layer was extracted with ethyl acetate (3×20 mL). The organic layers were washed with brine (20 mL), dried over sodium sulphate, filtered and evaporated. An off-white solid was obtained (2.45 g, 92%). The product was used for the next step without further purification. To a solution of this chlorotriazine (350 mg, 0.9 mmol) in THF (9 mL) at room temperature was added ethylenediamine (584 µL, 8.7 mmol), followed by triethylamine (1.22 µL, 8.7 mmol). After 20 h of reaction at 55° C., the solution was diluted with methanol (10 mL) and concentrated under reduced pressure. The crude residue was purified on a Biotage™ 25 S column (silica, hexane/AcOEt 1:1 to AcOEt/MeOH 3:7) to yield the primary amine as a white solid (227 mg, 62%). To a solution of this amine (37 mg, 87 µmol) in THF (1.5 mL) was added a solution of 2-amino-4-chloro-6-[2-(4 hydroxyphenyl)ethylamino]-1,3,5-triazine (30 mg, 79 µmol) in THF (1.5 mL), followed by diisopropylethylamine (50 µL, 280 µmol). After 48 h of reaction at 50° C., the solution was diluted with methanol (10 mL) and concentrated under reduced pressure. The crude residue was first purified on a Biotage™ 12 M column (silica, hexane/AcOEt 8:2 to AcOEt/MeOH 9:1) and then on a semi-preparative HPLC (C18 double-end capped column, 250×10 µm, 5 microns, $H_2O$/$CH_3CN$ containing 0.05% trifluoroacetic acid 7:3 to 1:9 over 20 min) to yield-compound 3 as a white solid. Yield of product: 17 mg, 33%; $^1H$ NMR (300 MHz, $CD_3OD$): δ 8.60-6.55 (m, 12H), 3.90 (s, 3H), 3.70-3.39 (m, 8H), 2.78-2.66 (m, 4H); LRMS (ESI): m/z 653.2 ($MH^+$); HPLC (method 1): 4.68 min.

Example 6

Synthesis of Compound 4

The above compound was prepared as in Example 1 starting with aniline and N-1-tert-butyloxycarbonyl-2-(4-aminophenyl)ethylamine. Removal of the Boc group was undertaken using a mixture of HCl/dioxane at room temperature for 3 h. White solid; $^1H$ NMR (400 MHz, $CD_3OD$): δ 7.59-7.21 (m, 161), 3.74-3.69 (m, 4H), 3.25-2.94 (m, 8H); LRMS (ESI): m/z 669.4 ($MH^+$); HPLC (method 2): 4.2 min.

Example 7

Synthesis of Compound 5

The above compound was prepared as in Example 1 starting with o-toluidine and 2-(4-hydroxyphenyl)ethylamine. White solid; $^1H$ NMR (400 MHz, $CD_3OD$): δ 7.11 (m, 2H), 7.02 (m, 4H), 6.97 (m, 6H), 6.66 (d, J=7 Hz, 4H), 3.47 (m, 8H), 2.70 (m, 4H), 2.24 (s, 6H); LRMS (ESI): m/z 699 ($MH^+$), 721 (M+Na); HPLC (method 2): 4.8 min.

Example 8

Synthesis of Compound 6

The above compound was prepared as in Example 1 starting with aniline and 4-aminobenzylamine. Light pink solid; $^1$NMR (400 MHz, $CD_3OD$) δ 7.72-6.61 (m, 18H), 4.39 (s, 4H), 3.55 (m, 4H); LRMS (ESI): m/z 663.2 (M+Na); HPLC (method 2): 3.6 min.

Example 9

Synthesis of Compound 7

The above compound was prepared by modification of the procedure of Example 1. To a suspension of 1,3-phenylenediamine (8.2 g; 75.3 mmol) in $CH_2Cl_2$ (21 mL) at 25° C. was added dropwise over 1 h a solution of di-tert-butylcarbonate (2.7 g, 12.6 mmol) in $CH_2Cl_2$ (130 mL), The solution was then stirred at room temperature overnight. After 18 h of reaction, the solution was evaporated to dryness under reduced pressure. The residual oil was dissolved in ethyl acetate (50 mL) and washed with a 2 N sodium carbonate solution (50 mL). The aqueous layer was extracted with ethyl acetate (2×50 mL). The combined organic layers were washed with brine (50 mL), dried over sodium sulphate, filtered and evaporated to dryness. The crude residue was purified on a Biotage™ 40S column silica, hexane/AcOEt 95:5 to 1:1) to yield N-1-tert-butyloxycarbonyl-1,3-phenylenediamine as an off-white solid (2.4 g, 93%). To a suspension of cyanuric chloride (2.2 g, 11.7 mmol) in acetone (15 mL) and ice (6 mL) at 0° C. was added dropwise over 15 min, a solution of N-1-tert-butyloxycarbonyl-1,3-phenylenediamine (2.4 g, 11.6 mmol) in acetone (7 mL). At the end of the addition the pH of the solution was adjusted from 1 to 7 with a 5% solution of sodium bicarbonate (25 mL). The white precipitate was filtered and washed thoroughly with water before being dried under high vacuum. This gave pure 2,4-dichloro-6-(3-N-1-tert-butyloxycarbonylaminophenyl) amino-1,3,5-triazine as an off-white solid (4.1 g, 99%). The product is used in the next step without further purification. To a solution of this compound (400 mg, 1.12 mmol) in THF (5 mL) at room temperature was added ethylenediamine (38 µL, 0.562 mmol), followed by diisopropylamine (345 µL, 1.97 mmol). After 20 h at 25° C., the solution was diluted with methanol (5 mL) and concentrated under reduced pressure. The crude residue was purified on a Biotage™ 25M column (silica, hexane/AcOEt 8:2 to 4:6) to yield N,N'-ethylenediamine di[4-chloro-6-(3-N-1-tert-butyloxycarbonylaminophenyl)-amino-1,3,5-triazine as a white solid (314 mg, 80%). This compound (85 mg, 0.1 mmol) was dissolved in THF (3 mL) at room temperature and add to a solution of 2-(4-aminophenyl)ethylamine (100 mg, 0.7 mmol) in THF (1 mL) followed by triethylamine (102 μL, 0.7 mmol). After 20 h at 60° C., the solution was diluted with methanol (2 mL) and concentrated under reduced pressure. The crude residue was purified on a Biotage™ 25S column (silica, hexene/EtOAc 8:2 to 2:8) to yield N,N'-ethylenediamine di[4-(2-[4-aminophenyl]ethylamino)-6-(3-N-tert-butyloxycarbonylaminophenyl)amino-1,3,5-triazine] as a white solid (97 mg, 89%). To a solution of this material (97 mg, 0.1 mmol) in $CH_2Cl_2$ (1.5 mL) at room temperature was added a solution of 4 N HCl in dioxane (1.5 mL). After 3 h at 25° C., the solution was diluted with 1,2-dichloroethane (10 mL), concentrated under reduced pressure and dried for 20 h under high vacuum. Yellow solid (74 mg, quantitative); $^1$H NMR (400 MHz, $CD_3OD$): δ 8.10-7.10 (m, 16H), 3.80-3.60 (m, 8H), 2.99 (m, 4H); LRMS (ESI): m/z 699.2 ($MH^+$); HPLC (method 2): 2.8 min.

Example 10

Synthesis of Compound 8

The above compound was prepared as in Example 1 starting with 2-(4-hydroxyphenyl)ethylamine and L-tyrosine methyl ester. Light pink solid; $^1$H NMR (400 MHz, $CD_3OD$): δ 7.54-6.65 (m 18H), 4.75 (m, 2H), 3.75-3.40 (m, 14H), 3.18-2.86 (m, 8H). LRMS (ESI): m/z 921.2; ($MH^+$); HPLC (method 2): 5.1 min.

Example 11

Synthesis of Compound 9

The above compound was prepared by saponification of compound 2 using excess lithium hydroxide in a mixture of methanol/water (4:1) at 50° C. overnight. Yellow solid; $^1$H NMR (400 MHz, $CD_3OD$): δ 9.00-6.50 (m, 16H), 3.70-3.45 (m, 8H), 2.90-2.75 (m, 4H); LRMS (ESI): m/z 759.20 ($MH^+$); HPLC (method 2): 7.1 min.

Example 12

Synthesis of Compound 10

The above compound was prepared as in Example 1 starting with (R)-2-phenylglycine methyl ester and 2-(4-hydroxyphenyl)ethylamine. Saponification was undertaken as described in Example 11. White solid; $^1$H NMR (300 MHz, $CD_3OD$); δ 7.48-7.32 (m, 10H), 7.05-6.89 (m, 4H), 6.70 (m, 4H), 5.45 (m, 2H), 3.53 (m, 8H), 2.66 (m, 4H); LRMS (ESI): m/z 787.2 ($MH^+$), 785.2 (M-H); HPLC (method 1): 6.5 min.

Example 13

Synthesis of Compound 11a

The above compound was prepared as in Example 1 except aniline was replaced by phenol, sodium bicarbonate by sodium hydride and diisopropylamine by sodium carbonate. White solid; $^1$H NMR (300 MHz, $CD_3OD$): δ 7.45-6.95 (m, 12H), 6.80-6.61 (m, 6H), 3.48 (m, 8 M), 2.72 (m, 4H); LRMS (ESI): m/z 673.2 ($MH^+$); HPLC (method 1): 8.4 min.

Example 14

Synthesis of Compound 11b

The above compound was prepared as in Example 1 starting with thiophenol and 2-(4-hydroxyphenyl)ethylamine. Pale orange solid; $^1$H NMR (400 M, $CD_3OD$): δ 7.10-7.64 (m, 10H), 6.40-7.00 (m, 8H), 2.92-3.50 (m, 8H), 2.29-2.70 (m, 10H). LRMS (ESI): m/z 705 ($MH^+$), 727 (M+Na); HPLC (method 2): 7.9 min.

Example 15

Synthesis of Compound 12

The above compound was prepared by coupling compound 1 and 4-(dimethylamino)butyric acid hydrochloride using an excess of 2-chloropyridinium iodide and triethylamine in DMF at room temperature overnight. The compound was purified on a semi-preparative HPLC (C18 double-end capped column, 250×10 μm, 5 microns, $H_2O/CH_3CN$ containing 0.05% trifluoroacetic acid 4:2 to 3:2 over 25 min). White solid; $^1$H NMR (400 MHz, $CD_3OD$): δ 7.52-7.04 (m, 18H), 3.70-3.39 (m, 12H), 3.00-2.75 (m, 8H), 2.92 (s, 9H), 2.85 (s, 3H), 2.11 (m, 4H); $^{19}$F NMR (400 MHz, $CD_3OD$): δ −77.5; quantitative $^{19}$F NMR (400 MHz, $CD_3OD$, coaxial insert trifluorotoluene): 8 TFA; LRMS (ESI): m/z 897 ($MH^+$), 919 (M+Na); HPLC (method 2): 3.8 min.

Example 16

Synthesis of Compound 13

The above compound was prepared as in Example 2 except 2-(4-hydroxyphenyl)ethylamine was first added to the 2,4-dichloro-6-phenylamino-1,3,5-triazine followed by adding the linker 2-(4-hydroxyphenyl)ethylamine using sodium hydride instead of sodium bicarbonate. The side chain ethanolamine was replaced by N-1-tert-butyloxycarbonylethylenediamine. Removal of the Boc group was undertaken with 5% trifluoroacetic acid in dichloromethane (0° C.). White powder; 1H NMR (300 MHz, $CD_3OD$): δ 7.59 (m, 6H), 7.21 (m, 8H), 7.05 (d, 1H, J=8 Hz), 6.91 (d, 1H, J=8 Hz), 6.71 (d, 1H, J=8H), 6.67 (d, 1H, J=8 Hz), 3.72 (m, 4H), 3.59 (t, 1H, J=8 Hz), 3.39 (m, 1H), 3.22 (m, 2H), 2.97 (m, 2H), 2.80 (t, 1H, J=7 Hz), 2.70 (t, 1H, J=7 Hz); $^{19}$F NMR (300 MHz, $CD_3OD$): δ −74.8; quantitative $^{19}$NMR (300 MHz, $CD_3OD$, coaxial insert trifluorotoluene): 3 TFA; LRMS (ESI): m/z 671 ($MH^+$), 654 (M-$NH_2$); HPLC (method 2): 4.5 min.

Example 17

Synthesis of Compound 14

The above compound was prepared by reacting compound 13 with 1-H-pyrazole-1-carboxamidine hydrochloride. Removal of the Boc group was undertaken as described in Example 16. White solid; $^1$H NMR (400 MHz, $CD_3OD$): δ 7.56 (m, 4H), 7.37 (m, 4H), 7.21 (m, 6H), 7.03 (d, 1H, J=8 Hz), 6.90 (d, 1H, J=8 Hz), 6.70 (d, 1H, J=8 Hz), 6.65 (d, 1H, J=8 Hz), 3.65 (m, 6H), 3.45 (m, 2H), 2.97 (m, 2H), 2.80 (t, 1H, J=8 Hz), 2.68 (t, 1H, J=8 Hz); $^{19}$F NMR (400 MHz, $CD_3OD$): δ −77.8; quantitative $^{19}$F NMR (400 MHz, $CD_3OD$, coaxial insert trifluorotoluene): 2 TFA; LRMS (ESI): m/z 713 ($MH^+$), 696 (M-$NH_2$); HPLC (method 2): 4.8 min.

Example 18

Synthesis of Compound 15

The above compound was prepared as in Example 2 except 2-(4-aminophenyl)ethylamine was first added to the 2,4-dichloro-6-phenylamino-1,3,5-triazine followed by adding the side chain N-1-acetylethylenediamine. White solid; $^1$H NMR (400 MHz, CD$_3$OD): δ 7.77-7.49 (m, 6H), 7.24 (t, 4H, J=7.9 Hz), 7.12 (d, 2H, J=8.4 Hz), 7.04 (d, 2H, J=8.4; H), 6.96 (m, 2H), 6.70 (d, 2H, J=8.4 Hz), 3.66-3.46 (m, 8H), 2.88-2.72 (m, 4H); LRMS (ESI): m/z 712.2 (MH$^+$); HPLC (method 2): 5.0 min.

Example 19

Synthesis of Compound 18

The above compound was prepared as in Example 2 except 2-(4-hydroxyphenyl)ethylamine was first added to the 2,4-dichloro-6-phenylamino-1,3,5-triazine followed by 2-(4-aminophenyl)ethylamine. Final substitution on the triazine ring was achieved using N-1-tert-butyloxycarbonylpiperazine and the removal of the Boc group was undertaken as described in Example 16. Yellow solid; $^1$H NMR (400 MHz, CD$_3$OD): δ 7.58 (m, 6H), 7.39-6.95 (m, 10H), 6.69 (m, 2H), 4.08 (m, 4H), 3.74-3.52 (m, 4H), 2.96-2.75 (m, 4H); LRMS (ESI): m/z 696.2 (MH$^+$); HPLC (method 2): 4.7 min.

Example 20

Synthesis of Compound 19a

The above compound was prepared as in Example 2 except aniline was replaced by N-1-tert-butyloxycarbonyl-1,3-phenylenediamine. Removal of the Boc group was undertaken as described in Example 9. Yellow solid; $^1$H NMR (400 MHz, CD$_3$OD): δ 8.05-7.11 (m, 16H), 3.94-3.48 (m, 8H), 3.00 (m, 4H); LRMS (ESI): m/z 700.2 (MH$^+$); HPLC (method 2): 3.2 min.

Example 21

Synthesis of Compound 19b

The above compound was prepared as in Example 2 except aniline was replaced by N-1-tert-butyloxycarbonyl-1,3-phenylenediamine and ethanolamine by 1,2-diaminoethane. Removal of the Boc group was undertaken as described in Example 9. Yellow solid; $^1$H NMR (400 MHz, CD$_3$OD): δ 7.00-7.60 (m, 16H), 3.40-3.70 (m, 6H), 3.00-3.20 (m, 2H), 2.70-2.90 (m, 4H); LRMS (ESI): m/z 700 (MH$^+$); HPLC (method 3): 1.3 min.

Example 22

Synthesis of Compound 20

The above compound was prepared as in Example 2 starting with aniline and ethanolamine. 2-(4-aminophenyl)ethylamine was replaced by 2-(4-hydroxyphenyl)ethylamine. Yellow solid; $^1$H NMR (400 MHz, CD$_3$OD): δ 7.61 (m, 6H), 7.25 (m, 4H), 7.14 (d, 2H, J=8.5 Hz), 7.07 (d, 2H, J=8.5 Hz), 6.98 (m, 2H), 6.70 (m, 2H), 3.69 (m, 2H), 3.55 (m, 6H), 2.83 (m, 4H); LRMS (ESI): m/z 671.2 (MH$^+$); HPLC (method 2): 5.1 min.

Example 23

Synthesis of Compound 21

The above compound was prepared as in Example 16. The side chain ethylenediamine was replaced by ethanolamine. White solid; $^1$H NMR (500 MHz, CD$_3$OD): δ 7.58-6.61 (m, 18H), 4.51 (m, 2H), 3.84 (m, 2H), 3.63 (m, 4H), 2.82 (m, 4H); LRMS (ESI): m/z 673.2 (MH$^+$), 695.2 (M+Na); HPLC (method 2): 9.7 min.

Example 24

Synthesis of Compound 22

The above compound was prepared using the solid phase procedure described in Example 3 starting with ethylenediamine and 2-methoxyaniline. LRMS (ESI): m/z 701.2 (MH$^+$), 722.4 (M+Na); HPLC (method 2): 4.2 min.

Example 25

Synthesis of Compound 23

The above compound was prepared using the solid phase procedure described in Example 3 starting with 1,4-diaminobutane and 2-methoxyaniline. LRMS (ESI): m/z 729.2 (MH$^+$), 751.2 (M+Na); HPLC (method 2): 4.9 min.

Example 26

Synthesis of Compound 24

The above compound was prepared using the solid phase procedure described in Example 3 starting with 1,3-diaminopropane and aniline. LRMS (ESI): m/z 684.4 (MH$^+$), 706.2 (M+Na); HPLC (method 2): 4.4 min.

Example 27

Synthesis of Compound 25

The above compound was prepared as in Example 1 except ethylenediamine linker was replaced with 1,3-diaminopropane. White solid; $^1$H NMR (400 MHz, CD$_3$OD): δ 7.72-7.48 (m, 4H), 7.20 (m, 4H), 7.08 (m, 6H), 6.66 (m, 4H), 3.46 (m, 8H), 2.71 (m, 4H), 1.74 (m, 2H); LRMS (ESI): m/z 685.2 (MH$^+$); HPLC (method 2): 6.0 min.

Example 28

Synthesis of Compound 26

The above compound was prepared as in Example 1 except 2-(4-hydroxyphenyl)ethylamine was replaced with ethanolamine and the linker ethylenediamine with 4-aminomethylpiperidine. White solid; $^1$H NMR (400 MHz CD$_3$OD): δ 7.60 (m, 4H), 7.24 (t, 4H, J=7.9 Hz), 6.95 (m, 2H), 3.69 (t, 4H, J=5.8 Hz), 3.50 (t, 4H, J=5.8 Hz), 3.31 (m, 4H), 2.85 (t, 2H, J=12.4 Hz), 1.95 (m, 1H), 1.81 (m, 2H), 120 (m, 2H); LRMS ESI): m/z 573.2 (MH$^+$); HPLC (method 2): 4.1 min.

Example 29

Synthesis of Compound 27

The above compound was prepared as in Example 22 except the linker 2-(4-aminophenyl)ethylamine was replaced with 4-aminobenzylamine and the side chain ethanolamine was replaced by histamine. White solid; $^1$H NMR (400 MHz, CD$_3$OD): ϵ 7.66 (m, 7H), 7.22 (m, 6H), 7.08-6.65 (m, 7H), 4.53 (s, 2H), 3.63 (t, 2H, J=7.1 Hz), 3.53 (m, 2H), 2.89 (t, 2H, J=7.1 Hz), 2.77 (m, 2H); LRMS (ESI): m/z 707.2 (MH$^+$), HPLC (method 2): 4.4 min.

Example 30

Synthesis of Compound 28

The above compound was prepared as in Example 9 except N-1-tert-butyloxycarbonyl-1,3-phenylenediamine was replaced with aniline, 2-(4-hydroxyphenyl)ethylamine with 2-(4-aminophenyl)ethylamine and the linker ethylenediamine with 1,4-phenylenediamine. White solid; $^1$H NMR (400 MHz, CD$_3$OD): δ 7.72-7.51 (m, 8H), 7.26 (t, 4H, J=7.9 Hz), 7.06 (d, 4H, J=7.1 Hz), 6.98 (t, 2H, J=7.1 Hz), 6.71 (t, 4H, J=8.2 Hz), 3.57 (t, 4H, J=7.3 Hz), 2.82 (t, 4H, J=7.3 Hz); LRMS (ESI): m/z 719.2 (MH$^+$); HPLC (method 1): 9.0 min.

Example 31

Synthesis of Compound 29

The above compound was prepared as in Example 1 except aniline was replaced with with N-1-tert-butyloxycarbonyl-1,3-phenylenediamine, 2-[4-hydroxyphenyl]ethylamine with 2-(4-aminophenyl)ethylamine and the linker ethylenediamine with piperazine. Removal of the Boc group was undertaken as described in Example 9. Brown solid; $^1$H NMR (400 MHz, CD$_3$OD): δ 7.46-7.30 (m, 14H), 6.98 (m, 2H), 4.00-3.85 (m, 8H), 3.80-3.75 (m, 4H), 3.01 (m, 4H); LRMS (ESI): m/z 725.4 (MH$^+$); HPLC (method 2): 3.4 min.

Example 32

Synthesis of Compound 30

The above compound was prepared as in Example 1 except aniline was replaced with N-1-tert-butyloxycarbonyl-1,3-phenylenediamine, 2-(4-hydroxyphenyl)ethylamine with 2-(4-aminophenyl)ethylamine and the linker ethylenediamine with 4-aminomethylpiperidine. Removal of the Boc group was undertaken as described in Example 9. Yellow solid; $^1$H NMR (400 MHz, CD$_3$OD): δ 7.78-7.07 (m, 16H), 3.83-3.56 (m, 6H), 3.14-2.92 (m, 8H), 2.17-1.75 (m, 5H); LRMS (ESI): m/z 753.4 (MH$^+$); HPLC (method 2): 3.2 min.

Example 33

Synthesis of Compound 31

The above compound was prepared as in Example 1 except aniline was replaced with N-1-tert-butyloxycarbonyl-1,3-phenylenediamine, 2-(4-hydroxyphenyl)ethylamine with 2-(4-aminophenyl)ethylamine and the linker ethylenediamine with 1,6-diaminohexane. Removal of the Boc group was undertaken as described in Example 9. Yellow solid: $^1$H NMR (400 MHz, CD$_3$OD): δ 7.85-7.06 (m, 16H), 3.74 (m, 4H), 3.48 (m, 4H), 3.01 (m, 4H), 1.68 (m, 4H), 1.47 (m, 2H); LRMS (ESI): m/z 755.2 (MH$^+$), 777.2 (M+Na); HPLC (method 3): 1.4 min.

Example 34

Synthesis of Compound 32

The above compound was prepared as in Example 1 except 2-(4-hydroxyphenyl)ethylamine was replaced with 2-(4-aminophenyl)ethylamine and the linker ethylenediamine with 4-aminomethylpiperidine. Yellow solid; $^1$H NMR (400 MHz, CD$_3$OD): δ 7.66-6.74 (m, 18H), 3.64 (m, 4H), 3.09-2.78 (m, 10H), 2.04 (m, 2H), 1.88 (m, 3H); LRMS (ESI): m/z 723.2 (MH$^+$); HPLC (method 2): 4.1 min.

Example 35

Synthesis of Compound 33

The above compound was prepared as in Example 2 except the linker 2-(4-aminophenyl)ethylamine was replaced with N-1-tert-butyloxycarbonylpiperazine. Removal of the Boc group was undertaken as described in Example 16. Light yellow solid; $^1$H NMR (400 MHz, CD$_3$OD): δ 7.60 (m, 4H), 7.25 (m, 4H), 6.98 (m, 4H), 6.68 (d, 2H), J=8.2 Hz), 3.83 (m, 8H), 3.70 (t, 2H, J=5.6 Hz), 3.52 (m, 6H), 2.76 (t, 4H, J=6.3 Hz); LRMS (ESI): m/z 620.2 (MH$^+$); HPLC (method 2): 4.3 min.

Example 36

Synthesis of Compound 34

The above compound was prepared as in Example 2 except the linker 2-(4-aminophenyl)ethylamine was replaced with 5-amino-2-methylbenzylamine. Light yellow solid. $^1$H NMR (400 MHz, CD$_3$OD): δ 7.75-6.92 (m, 15H), 6.64 (d, 2H, J=8.0 Hz), 4.52 (s, 2H), 3.68-3.41 (m, 6H), 2.73 (m, 2H), 2.30 (s, 3H); LRMS (ESI): m/z 670.2 (MH$^+$); HPLC (method 2): 4.4 min.

Example 37

Synthesis of Compound 35

The above compound was prepared as in Example 2 except the linker 2-(4-aminophenyl)ethylamine was replaced with 3-aminobenzylamine. Orange solid; $^1$H NMR (400 MHz, CD$_3$OD): δ 7.75-6.64 (m, 18H), 4.37 (s, 2H), 3.77-3.39 (m, 6H), 2.79 (m, 2H); LRMS (ESI): m/z 656.2 (MH$^+$); HPLC (method 3): 2.4 min.

Example 38

Synthesis of Compound 36

The above compound was prepared as in Example 1 except 2-(4-hydroxyphenyl)ethylamine was replaced with 2-(4-aminophenyl)ethylamine and the linker ethylenediamine with piperazine. Pink solid; $^1$H NMR (400 MHz, CD$_3$OD): δ 7.75-6.68 (m, 18H), 3.98-3.65 (m, 16H), 2.77 (m, 4H); LRMS (ESI): m/z 695.2 (MH$^+$); HPLC (method 3): 2.2 min.

Example 39

Synthesis of Compound 37

The above compound was prepared as in Example 2 except ethanolamine was replaced with 2-(4-hydroxyphenyl)ethylamine and the linker 2-(4-aminophenyl)ethylamine with 2-aminobenzylamine. White solid; $^1$H NMR (400 MHz, CD$_3$OD): δ 7.62-6.60 (m, 22H), 4.44-4.38 (m, 2H), 3.53-3.47 (m, 4H), 2.80-2.72 (m, 4H); LRMS (ESI): m/z 733.2 (MH$^+$); HPLC (method 2): 6.5 min.

Example 40

Synthesis of Compound 38

The above compound was prepared as in Example 9 except N-1-tert-butyloxycarbonyl-1,3-phenylenediamine was replaced with aniline, 2-(4-aminophenyl)ethylamine with 2-(4-hydroxyphenyl)ethylamine and the linker ethylenediamine with 1,3-phenylenediamine. Light yellow solid; $^1$H NMR (400 MHz, CD$_3$OD): δ 7.61 (m, 4H), 7.29-6.92 (m, 14H), 6.69 (d, 4H, J=7.4 Hz), 3.52 (t, 4H, J=7.2 Hz), 2.79 (t, 4H, J=7.2 Hz); LRMS (FAB+): m/z 719.4 (MH$^+$); LRMS (ESI): m/z 719.2 (MH$^+$); HPLC (method 1): 8.6 min.

Example 41

Synthesis of Compound 39

The above compound was prepared as in Example 1 except that the monochlorotriazine was treated first with (R)-phenylglycinol and triethylamine and the product obtained was treated with sodium hydride. White solid; $^1$H NMR (500 MHz, CD$_3$OD): δ 7.69-6.61 (m, 23H), 5.15 (m, 1H), 3.96-3.37 (m, 6H), 2.89 (m, 4H); LRMS (ESI): m/z 748.2 (MH$^+$); HPLC (method 1): 8.8 min.

Example 42

Synthesis of Compound 40

The above compound was prepared using the solid phase procedure described in Example 3 starting with aniline and ethylenediamine. LRMS (ESI): m/z 670.4 (MH$^+$), 692.2 (M+Na); HPLC (method 2): 4.2 min.

Example 43

Synthesis of Compound 41

The above compound was prepared by method B (scheme 1) starting with N-1-tert-butyloxycarbonyl-1,3-phenylenediamine and p-xylenediamine. 2-(4-hydroxyphenyl)ethylamine was replaced by ammonia gas. Yellow solid; $^1$H NMR (400 MHz, CD$_3$OD): δ 7.83 (m, 2H), 7.69 (m, 2H), 7.41 (m, 6H), 7.12 (m, 2H), 4.63 (m, 4H); $^{19}$F NMR (376 MHz, CD$_3$OD, coaxial insert trifluorotoluene): 2 TFA; LRMS (ESI): m/z 537.4 (MH$^-$), 559.2 (M+Na); HPLC (method 5): 4.1 min.

Example 44

Synthesis of Compound 42

The above compound was prepared as in Example 2 starting with N-1-tert-butyloxycarbonyl-1,3-phenylenediamine. 2-(4-aminophenyl)ethylamine was replaced by ethanolamine and the linker 2-(4-aminophenyl)ethylamine with 4-aminobenzylamine. Pale yellow solid; $^1$H NMR (400 MHz, CD$_3$OD): δ 8.10-7.87 (m, 1H); 7.86-7.70 (m, 4H); 7.69-7.58 (m, 2H); 7.57-7.40 (m, 5H): 7.20-7.06 (m, 3H); 4.74 (s, 2H); 3.79-3.71 (m, 2H); 3.68-3.56 (m, 2H); LRMS (ESI) m/z 658 (MH$^+$), 680 (M+Na); HPLC (method 5): 5.7 min.

Example 45

Synthesis of Compound 43

The above compound was prepared as in Example 2 starting with N-1-tert-butyloxycarbonyl-1,3-phenylenediamine. 2-(4-aminophenyl)ethylamine was replaced by ethanolamine and the linker 2-(4-aminophenyl)ethylamine with 3-aminobenzylamine. Pale yellow solid; $^1$H NMR (400 MHz, CD$_3$OD): δ 8.06-7.90 (m, 1H); 7.85-7.67 (m, 4H); 7.66-7.57 (m, 2H); 7.56-7.38 (m, 5H); 7.20-7.08 (m, 3H); 4.77 (s, 2H); 3.76-3.72 (m, 2H); 3.68-3.56 (m, 2H); LRMS (ESI) m/z 658 (MH$^+$), 680 (M+Na); HPLC (method 5): 5.7 min.

Example 46

Synthesis of Compound 44

The above compound was prepared as in Example 2 starting with N-1-tert-butyloxycarbonyl-1,3-phenylenediamine. 2-(4-aminophenyl)ethylamine was replaced by ethanolamine and the linker 2-(4-aminophenyl)ethylamine with piperazine. Off-white solid; $^1$H NMR (400 MHz, CD$_3$OD); δ 8.10-7.82 (m, 3H); 7.8-7.65 (m, 2H); 7.63-7.57 (m, 2H); 7.52 (t, J=8.2 Hz, 2H); 7.31-7.19 (m, 1H); 7.11 (d, J=8.0 Hz, 2H); 4.09 (s, 8H); 3.81-3.70 (m, 2H); 3.60-3.53 (m, 2H; LRMS (ESI) m/z 622 (MH$^+$), 644 (M+Na); HPLC (method 5): 5.9 mm.

Example 47

Synthesis of Compound 45

The above compound was prepared as in Example 2 starting with N-1-tert-butyloxycarbonyl-1,3-phenylenediamine and ammonia. 2-(4-aminophenyl)ethylamine was replaced by 3-aminobenzylamine and the linker 2-(4-aminophenyl)ethylamine with 4-aminobenzylamine. Yellow solid: $^1$H NMR (400 MHz, CD$_3$OD): δ 7.85-1.24 (m, 14H), 7.14 (m, 2H), 4.72 (m, 4H); LRMS: (ESI): m/z 628.4 (MH$^+$), 651.2 (M+Na); HPLC (method 4): 2.7 min.

Example 48

Synthesis of Compound 46

The above compound was prepared by method B (scheme 1) starting with N-1-tert-butyloxycarbonyl-1,3-phenylenediamine and 1,3-phenylenediamine. 2-(4-hydroxyphenyl)ethylamine was replaced by ethanolamine and ammonia gas. White solid; $^1$H NMR (400 MHz, CD$_3$OD): δ 7.69 (m, 3H), 7.42 (m, 6H), 7.08 (m, 3H), 3.73 (m, 2H), 3.64 (m, 2H); LRMS (ESI): m/z 553.4 (MH$^+$), 575.6 (M+Na); HPLC (method 4): 2.0 min.

Example 49

Synthesis of Compound 47

The above compound was prepared by method B (scheme 1) starting with N-1-tert-butyloxycarbonyl-1,3-phenylenediamine and 1,4-phenylenediamine. 2-(4-hydroxyphenyl)ethylamine was replaced by ethanolamine. White solid; $^1$H NMR (400 MHz, CD$_3$OD): δ 7.74 (m, 2H), 7.69 (m, 6H), 7.53 (m, 2H), 7.19 (m, 2H), 3.77 (m, 4H), 3.64 (m, 4H); LRMS (ESI): m/z 597.4 (MH$^+$), 619.6 (M+Na); HPLC (method 4): 2.3 min.

Example 50

Synthesis of Compound 48

The above compound was prepared by method B (scheme 1) starting with N-1-tert-butyloxycarbonyl-1,3-phenylenediamine and p-xylenediamine. 2-(4-hydroxyphenyl)ethylamine was replaced by aminobenzylamine. Yellow solid; $^1$H NMR (400 MHz, CD$_3$OD): δ 7.75-7.23 (m, 18H), 7.38 (m, 2H), 4.71 (m, 8H); LRMS (ESI): m/z 747.4 (MH$^+$); HPLC (method 4): 3.5 min.

Example 51

Synthesis of Compound 49

The above compound was prepared by method B (scheme 1) starting with N-1-tert-butyloxycarbonyl-1,3-phenylenediamine and 1,3-phenylenediamine 2-(4-hydroxyphenyl)ethylamine was replaced by ethanolamine. White solids: $^1$H NMR (400 MHz, CD$_3$OD): δ 7.71 (m, 3H), 7.48 (m, 6H), 7.11 (m, 3H), 3.74 (m, 4H), 3.65 (m, 4H); LRMS (ESI): m/z 597.2 (MH$^+$); HPLC (method 4): 2.2 min.

Example 52

Synthesis of Compound 50

The above compound was prepared by method B (scheme 1) starting with N-1-tert-butyloxycarbonyl-1,3-phenylenediamine and 1,3-phenylenediamine. 2-(4-hydroxyphenyl)ethylamine was replaced by serinol. Brown solid; $^1$H NMR (400 MHz, CD$_3$OD): δ 8.20-7.00 (m, 12H), 3.75 (m, 8H), 3.64 (m, 2H); LRMS (ESI): m/z 657.4 (MH$^+$), HPLC (method 5): 4.5 min.

Example 53

Synthesis of Compound 51

The above compound was prepared by method B (scheme 1) staring with N-1-tert-butyloxycarbonyl-1,3-phenylenediamine and 1,3-phenylenediamine. 2-(4-hydroxyphenyl)ethylamine was replaced by ammonia gas. Off-white solid; $^1$H NMR (400 MHz, CD$_3$OD): δ 7.71 (m, 3H), 7.42 (m, 6H, 7.11 (m, 3H); LRMS (ESI): m/z 509.4 (MH$^+$), 531.4 (M+Na); HPLC (method 4): 1.7 min.

Example 54

Ability of Compounds to Mimic Protein A as Determined by Competitive Protein A Binding ELISA As described above, this assay evaluates the ability of the exemplified compounds to mimic protein A. Such compounds can bind to the Fc portion of human IgG as ascertained by the inhibition of binding of protein A to human IgG. The competitive protein A binding ELISA assay was performed on a 96-well plate Maxisorp surface to enhance the binding of protein A to the bottom of the plate. The wells were coated with 100 μL of protein A (0.8 μg) and incubated overnight at 4° C. After incubation, unbound protein A was removed by three washes with phosphate buffer saline (PBS). The plate was then incubated with 100 μL/well of a 2% solution of bovine serum albumin (BSA) for 1 h at 37° C. to block non specific protein binding. After incubation, the plate was washed to times with PBS. 50 μL of compound or protein A, diluted in PBS or PBS-20% DMSO at appropriate concentration, were added to the wells followed by addition of 50 μL of peroxidase-conjugated human IgG (HRP-IgG). After 1 h incubation at 37° C., the plate was washed free times with PBS to remove unbound HRP-IgG. Bound HRP-IgG was detected by incubation with 100 μL of 2,2'-Azino-di[3-ethyl-benzothiazoline sulfonate]diammonium salt crystals (ABTS) solution for 20 min in the dark at room temperature. The plate was then read at 405 nm on a EL 800, universal Microplate reader (Bio-Tek). Data was analyzed in Microsoft Excel and the concentration of compound which inhibits 50% binding of protein A (IC$_{50}$) was calculated using Prism software.

Table 1 represents the IC$_{50}$ of compounds tested in the competitive protein A binding ELISA assay, which consists of a side-by-side analysis in PBS and PBS-20% DMSO. DMSO was used to increase the solubility of some of the compounds. These data illustrate the ability of compounds of this invention to inhibit the binding of protein A to the Fc portion of IgG.

TABLE 1

IC$_{50}$ (μM) of protein A mimic compounds as ascertained by ELISA

| Compound # | IC$_{50}$ (μM): Assay in PBS | IC$_{50}$ (μM): Assay in PBS-20% DMSO |
|---|---|---|
| 1 | | 50 |
| 4 | 44 | 40 |
| 5 | | 36 |
| 6 | 2.4 | 0.4 |
| 7 | 0.2 | 0.02 |
| 8 | | 28 |
| 9 | | 50 |
| 10 | 69 | 85 |
| 11b | | 45 |
| 12 | 23 | 39 |
| 13 | 33 | 70 |
| 14 | 33 | 63 |
| 15 | | 35 |
| 16 | 36 | 55 |
| 17 | 53 | 12 |
| 18 | 26 | 43 |
| 19a | 0.06 | 0.003 |
| 20 | | 26 |
| 21 | | 34 |
| 27 | | 28 |
| 28 | | 35 |
| 29 | 0.2 | 0.003 |
| 30 | 0.4 | 0.03 |
| 31 | 0.99 | 0.12 |
| 32 | 33 | 2 |
| 33 | 18 | 18 |
| 34 | 23 | 1 |
| 35 | 23 | 1 |
| 36 | | 16 |
| 37 | | 23 |
| 39 | | 43 |
| 41 | 0.03 | 0.02 |
| 42 | 0.05 | 0.05 |
| 43 | 0.08 | 0.05 |
| 44 | 0.09 | 0.04 |
| 45 | 0.1 | 0.08 |
| 46 | 0.2 | 0.8 |
| 47 | 0.2 | 0.2 |
| 48 | 0.2 | 0.05 |
| 49 | 0.3 | 0.5 |
| 50 | 0.4 | 1 |
| 51 | 0.6 | 6 |

Table 2 summarizes the IC$_{50}$ of four potent protein A mimic compounds compared to soluble protein A on the competitive ELISA assay. The results further demonstrate the ability of protein A mimic compounds to inhibit the binding of protein A to human IgG.

TABLE 2

IC$_{50}$ (μM) of four compounds compared to protein A in the competitive ELISA assay

| IC$_{50}$ (n = 5 or 6) | Protein A | Compound 19a | Compound 7 | Compound 29 | Compound 30 |
|---|---|---|---|---|---|
| PBS | 0.187 μM | 0.088 μM | 0.187 μM | 0.225 μM | 0.426 μM |
| PBS-20% DMSO | 0.336 μM | 0.0035 μM | 0.0217 μM | 0.0029 μM | 0.033 μM |

Example 55

Effect of Compounds on Phagocytosis of Immune Complexes

This assay was performed to determine the ability of protein A mimic compounds to stimulate or inhibit uptake of FITC-Immune Complex (IC). FITC-IC was prepared by mixing human serum albumin (HSA)-fluorescein isothiocyanate (FITC) with mouse IgG anti-HSA at a 1:4 ratio (four molecules of antibody for one molecule of antigen) on a rotary shaker for 1 h at room temperature. Soluble IC was then incubated with or without compounds or protein A for 10 min. This mixture was added to RAW 264.7 cells and incubated for 2 h at 37° C. for IC phagocytosis. After incubation, cells were washed twice in cold PBS (5 min, 1200 rpm) and fixed with 500 µL PBS containing 2% formaldehyde. FITC signal taken up by RAW 264.7, which is indicative of IC phagocytosis, was determined by flow cytometry analysis in a Becton Coulter counter with an argon laser and signal was measured through a 530/30 nm filter.

FIG. 1 illustrates a dose-response curve of compound 1 on the phagocytosis of IC with RAW 264.7 (macrophage-like) cells. Results show that phagocytosis of IC is similar to the control at a concentration below 0.4 µM of compound 1. An increase in phagocytosis of IC is observed at concentrations of 1, 2 and 4 µM, followed by an inhibition at 10 and 20 µM (approximately 20%). Phagocytosis of IC was also undertaken with compound 14 and protein A. Phagocytosis of IC is inhibited by compound 14 (approximately 50% at 20 µM and protein A (approximately 50% at 2 µM and 20 µM.

Example 56

Effect of Compounds on TNFα Induced Apoptosis in WEHI 13-VAR Cell Line

Effect of compounds on TNFα-induced apoptosis was measured by a standard biological assay using WEHI-13VAR cells. These cells undergo apoptosis when they are incubated in the presence of TNFα and actinomycin D. $2\times10^4$ WEHI-13VAR cells were incubated in RPMI supplemented with 1% sodium pyruvate and 10% FBS, overnight at 37° C. for cell adherence. The cells were then cultured in the presence of 1 µg/mL of actinomycin D (to inhibit protein synthesis) and 0.04 nM TNFα with or without compounds at 37° C. After 16-24 h, 50 µL of a solution of 2 mg/mL of MTT was added to each well and the plate was then incubated for 4 h at 37° C. Only viable cells metabolize MTT to form formazan salt, which is detectable by the measurement of absorbance at 570 nm. After the incubation, the plate was inverted to remove medium and dead cells. 150 µL DMSO was added to each well to stop the reaction and solubilize the formazan salt. Optical density was read on a EL 800, universal Microplate reader (Bio-Tek). A decrease in the optical density is direct evidence of cell apoptosis induced by TNFα. Compounds were also compared to the activity of an anti-TNFα neutralizing antibody. A negative value indicates that the tested compounds, at that particular concentration, were able to stimulate apoptosis.

Table 3 represents the percentage of TNFα inhibition (apoptosis) of compounds tested in the cell-based TNFα sensitive WEHI-VAR13 cell proliferation assay. The compounds demonstrated a TNF-α inhibitory activity in the range of 30-50%. In comparison, TNFα antibody demonstrated a TNFα inhibitory activity of 90-95%. This data illustrates the ability of compounds of this invention to inhibit the apoptotic activity of TNFα on TNFα sensitive WEHI-VAR13 cells.

TABLE 3

Effect of compounds on TNF-α inhibition.

| | WEHI-13VAR assay % inhibition of apoptosis | | | |
|---|---|---|---|---|
| Compound # | $4 \times 10^{-5}$M | $2 \times 10^{-5}$M | $1 \times 10^{-5}$M | $5 \times 10^{-6}$M |
| 1 | −3.8 | 17.7 | 36.8 | 14.3 |
| 2 | 48.3 | 48.4 | 43.7 | 37.3 |
| 3 | 33.9 | 44.6 | 32.7 | 0.5 |
| 4 | 44.0 | 25.3 | 11.2 | 2.4 |
| 5 | 35.4 | 38.7 | 35.1 | 28.9 |
| 12 | −30 | −28.4 | −21.1 | 36.9 |
| 25 | −17.8 | −0.7 | 22.8 | 27.5 |
| 26 | −11.5 | 38.0 | 27.3 | 9.7 |
| 42 | 30.4 | 0.5 | −1.7 | −3.1 |
| 45 | 32.9 | 4.1 | 2.9 | −0.3 |

Example 57

Effect of Compounds on the Binding of TNFα to the p55 TNFα Receptor (CD120a) and the p75 TNFα Receptor (CD 120b)

Compounds were tested for their ability to bind to TNFα or inhibit the interaction of TNFα with its respective receptors; p55 and p75 TNFα receptor. Three binding ELISA assays were undertaken as described by Mancini et al. Biochemical Pharmacology 58, 851-859 (1999). TNFα or receptor (1 µg/mL) was coated on a 96-well plate Maxisorp, overnight at 4° C. After incubation, unbound TNFα or p55 TNFα receptor or p75 TNFα receptor was removed and the plate washed three times with PBS. The plate was then incubated with 100 µL/well of a 2% BSA solution for 1 h at 37° C. to block non specific protein binding. After incubation, the plate was washed three times with PBS. Biotinylated recombinant human TNFα p55 or p75 receptor or biotinylated recombinant human TNFα was added to the wells in the presence or absence of compounds. The plate was incubated for 1 h at 37° C. After incubation, the plate was washed three times with PBS to remove unbound labeled p55 or p75 receptor or recombinant human TNFα. 100 µL of avidin-HRP (diluted ½000 in PBS-0.1% BSA) was added to each well and incubated 1 h at 37° C. Bound p55 or p75 receptor or recombinant human TNFα was detected by the addition of 200 µL of 3,3',5,5'-tetramethylbenzidine (TMB) per well for 15 min. The plate was then read at 655 nm on a EL 800 universal Microplate reader (Bio-Tek, Mississauga, Canada). Data was analyzed in Microsoft Excel and recorded as the percentage of inhibition of p55 or p75 binding to TNFα or TNFα binding to RI (p55) or RII (p75).

Table 4 illustrates the effect of compounds on the inhibition of the direct binding of TNFα RI and RII to TNFα (plastic coated) and TNFα with its receptors plastic coated). When TNFα is coated on plastic, compounds do not inhibit the binding of RI and RII receptors to TNFα. But when the receptors are coated on plastic, compounds inhibit the binding of TNFα to RII receptor and RI receptor to a lesser extent. The results suggest that inhibition appears not to be due to direct binding of compound to TNFα receptor but instead to TNFα. An inhibition of less than 20% was considered to be insignificant. A negative percentage of inhibition may be due to precipitation or an increase in binding of TNFα to its respective receptors.

TABLE 4

Effect of compounds on binding of RI or RII or TNF-α.

| | RI and RII Binding assay to TNF | | | | TNF binding assay to TNF RI and RII Receptors | | | |
|---|---|---|---|---|---|---|---|---|
| | % Inhibition of sTNF-R1 binding to TNF-α | | % Inhibition of sTNF-R2 binding to TNF-α | | % Inhibition of TNF-α binding to TNF-R1 | | % Inbibitina of TNF-α binding to TNF-R2 | |
| Compound # | $10^{-4}$ M | $10^{-5}$ M | $10^{-4}$ M | $10^{-5}$ M | $10^{-4}$ M | $10^{-5}$ M | $10^{-4}$ M | $10^{-5}$ M |
| 1 | 2.7 | 0 | 0 | 0 | 46 | 28.9 | 63.3 | 38.4 |
| 4 | 2.19 | 4.5 | 5.26 | 2.06 | −69.37 | −47.43 | −104.77 | −86.7 |
| 5 | 1.54 | 2.95 | 2.68 | 4.31 | 15.4 | 4.6 | 38.5 | 21.2 |
| 7 | | | | | 32.6 | 10.4 | 36.9 | 43.3 |
| 12 | | | | | −8.4 | −35.7 | 3.8 | −30.4 |
| 19a | | | | | 13.3 | −4 | 27.4 | 24.3 |
| 25 | 5.65 | 6.74 | 4.22 | 6.76 | 22.95 | 3.95 | 49.25 | 4.8 |

Example 58

Effect of Compounds on LPS-Induced TNFα Production in Mouse J774A-1 Cell Line

Effect of compounds on TNFα production was measured by ELISA using J774-1 cells stimulated by LPS. J774-1 cells were cultured in the presence or absence of LPS and compound. Cells were cultured at 37° C. for 24 h and thereafter the supernatants were collected for the determination of the concentration of TNFα by ELISA as recommended by the manufacturer (BD Biosciences). Data was analyzed in Microsoft Excel and the concentration of compound which inhibits 50% of TNFα production ($IC_{50}$) was calculated using Prism software.

Table 5 summarizes the effect of compounds on TNFα production induced by LPS on J774-1 cells.

TABLE 5

Effect of compounds on the inhibition of TNFα released by LPS induction from J774A.1 cells.

| Compound # | $IC_{50}$ (μM) |
|---|---|
| 1 | 9.2 |
| 3 | 28.0 |
| 4 | 94.4 |
| 5 | 44.0 |
| 11a | 45 |
| 11b | 23.3 |
| 12 | 3.4 |
| 13 | 13.4 |
| 14 | 11.8 |
| 15 | 14.2 |
| 16 | 13.6 |
| 17 | 57.1 |
| 18 | 10.2 |
| 19a | 20.7 |
| 20 | 23.3 |
| 21 | 4.8 |
| 22 | 62.1 |
| 23 | 16.5 |
| 24 | 11.5 |
| 25 | 15.9 |
| 28 | 28.8 |
| 33 | 20.6 |
| 38 | 9.5 |
| 40 | 87.2 |

Example 59

Effect of Protein A Mimic Compounds on Peripheral Blood Mononuclear Leukocytes (PBML) Cells Cytotoxicity, DNA, RNA and Protein Synthesis PBML were obtained from the peripheral blood of healthy volunteers. Blood was submitted to gradient centrifugation with Lympholyte-poly (Cedarlane, Hornby, Canada). The layer, which contains the mononuclear leukocytes, was collected and the cells washed three times in PBS. Cells were then suspended in RPMI (Gibco, Burlington, Canada) supplemented with 10% PBS (cyclone, Logan USA). Viability was greater than 99% as determined by trypan blue exclusion.

PBML were resuspended at $2\times10^6$ cells mL. 100 μL of PBML ($2\times10^5$ cells) were incubated in a 96-well microtiter plate for 48 h in the presence or absence of compound or protein A. Cells were quiescent or stimulated with concanavalin A (ConA; T-cells) or pokeweed mitogen (PWM; B-cells). After incubation, cells were treated with MTT (cytotoxicity) or pulsed with 1 μCi of [$^3$H]-thymidine (DNA synthesis), [$^3$H]-uridine (RNA synthesis) or [$^3$H]-leucine (protein synthesis) for 6 h. Plates were harvested on a Tomteck and counted on a Microbeta β-counter.

Table 6 summarizes the effect of protein A mimic compounds on cell cytotoxicity, DNA, RNA and protein synthesis in comparison with protein A on PBML. Protein A has no effect on DNA, RNA and protein synthesis. Furthermore, it does not induce cell cytotoxicity. Cell cytotoxicity was observed only on PBML stimulated with Con A, a mitogen stimulating T-cell proliferation. No cytotoxic effect was observed in resting PBML PWM, a mitogen stimulating B-cell proliferation, stimulation is not affected by the protein A mimic compounds. Furthermore, compound 1, 7 and 19a suppress DNA and RNA synthesis in both resting and stimulated (ConA and PWM) PBML. Only compound 1 and 19a, however, inhibit protein synthesis in resting and stimulated PBML. These results suggest a suppression of both T and B cells. Theses cells are strongly implicated in autoimmune diseases.

TABLE 6

Effect of protein A mimic compounds on resting and stimulated PBML cytotoxicity, DNA, RNA and protein synthesis.

| | PBML ($IC_{50}$ Results in µM) | | | | | | | | | | | |
|---|---|---|---|---|---|---|---|---|---|---|---|---|
| | Cytotoxicity | | | DNA Synthesis | | | RNA Synthesis | | | Protein Synthesis | | |
| Compond # | Resting | ConA $IC_{50}$ | PWM | Resting | ConA $IC_{50}$ | PWM | Resting | ConA $IC_{50}$ | PWM | Resting | ConA $IC_{50}$ | PWM |
| Protein A | >20 | >20 | >20 | * | >20 | >20 | * | >20 | >20 | >20 | * | * |
| 1 | >10 | 8.7 | >10 | 2.49 | 1.42 | 0.77 | 1.1 | 0.92 | 0.66 | 6.48 | 2.44 | 2.96 |
| 7 | >10 | >10 | >10 | 3.6 | 3.52 | 1.28 | 1.12 | 1.5 | 1.78 | >10 | >10 | >10 |
| 19a | 10 | 6.8 | >10 | 1.9 | 1.57 | 4.38 | 0.399 | 0.693 | 0.398 | 9.9 | 3.91 | 4.88 |

*Increase

Example 60

Effect of Compounds on Systemic Lupus Erythematosus (SLE)-Glomerulonephritis New Zealand mice of the F1 hybrid cross NZBxNZW develop most of the autoimmune abnormalities seen in human SLE and die from SLE-like immune complex (IC)-mediated glomerulonephritis. The mice develop high titers of anti-DNA (double-strand and single-strand) and nuclear extract (NE) antibodies, as well as SLE-related clinical manifestations including leukopenia, thrombocytopenia, proteinuria and glomerulonephritis. These mice develop anti-DNA antibodies after the age of 3 months, with a peak of anti-DNA antibody response occurring at 7 months. Subsequently, the serum concentration of anti-DNA antibodies declines, presumably as a consequence of progressive uremia. The first serological manifestations of the disease occurs at about 150 days (5 months). Their survival is evaluated at approximately 250 days.

Figure 2:
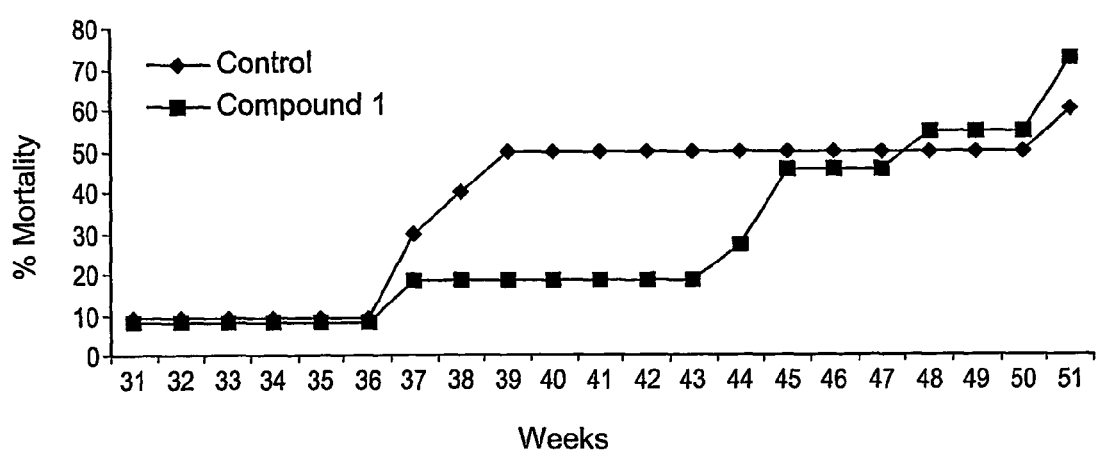

FIG. 2 illustrates the effect of compound 1 on the mortality of the NZBxNZW mice. Intravenous administration of compound or vehicle was undertaken once a week from week 18 to week 37. Treatment ceased for 11 weeks and was restarted at week 48 for the control and compound 1 groups. Results indicate that compound 1 reduces the mortality of NZBxNZW mice at week 37. It also delays the appearance of symptoms and mortality up to week 45. FIG. 3 illustrates the proteinuria at week 48 to 51. The amount of protein greater than 5 g/liter in the compound 1-treated mice was greater than the control due to the kinetics of the disease (exponential phase).

Figure 3A:
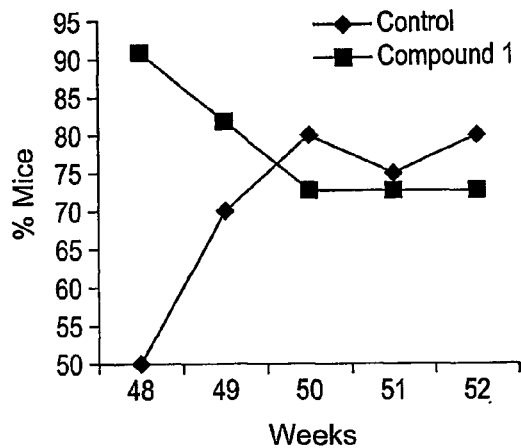
FIG. 3A illustrates mice with 5 g/L or more and FIG. 3B illustrates mice with improvement of kidney filtration.
Figure 3B:
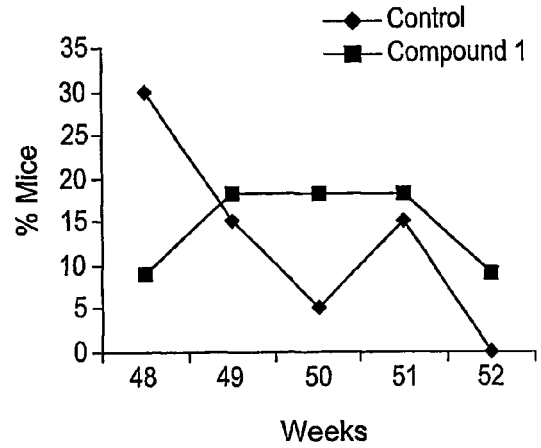

But with the continuation of treatment at week 48 to week 52 using weekly intravenous administration of the vehicle or compound, compound 1 induces a decrease in protein concentration (5 g/liter) in urine compared to the vehicle alone (FIG. 3A). Furthermore, an increase in trace amount of protein in urine is observed in mice mated with compound 1 (FIG. 3B) indicating an improvement in kidney filtration.

Figure 4:
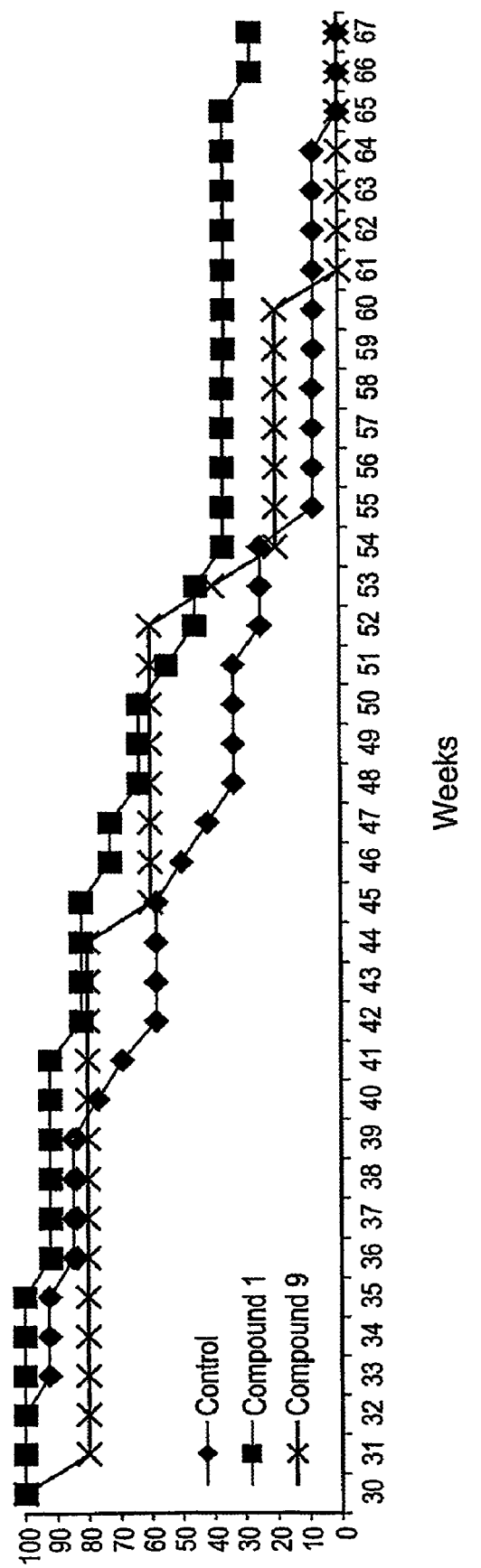
FIG. 4 illustrates the effect of compounds 1 and 9 on mortality of NZBxNZW mice.

The results of a second SLE are presented in FIG. 4. Compounds delay the mortality, as seen by an increase in survival of NZBxNZW mice. Compounds 1 and 9 increase the survival up to 35% compared to the control group. Furthermore, compound 1 extended survival up to 89 weeks compared to 65 weeks for control.

Figure 5:
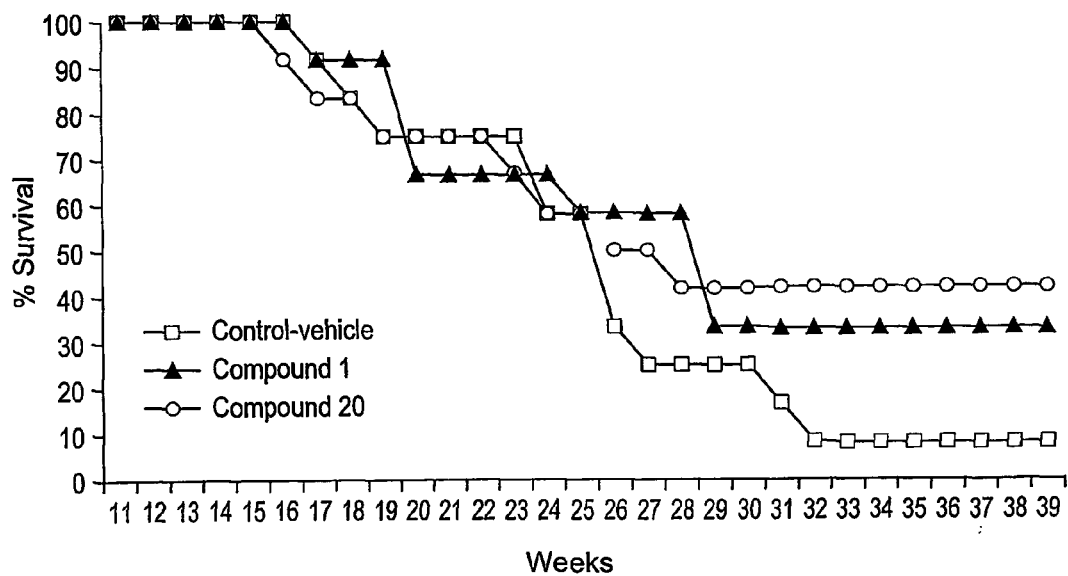
FIG. 5 illustrates the effect of compounds 1 and 20 on mortality of MRL/lpr mice.

FIG. 5 is an example of the effect of compounds on survival of MRL/lpr mice. These mice also spontaneously develop SLE-like syndrome. MRL/lpr have a homozygous fas mutation, which accelerates autoimmunity. Compounds delay the mortality as seen by an increase in survival of MRL/lpr mice. Furthermore, compounds 1 and 20 increase the survival (40%) compared to the control group (10%).

Example 61

Effect of Compounds on Oxazolone-Induced Delayed-Type Hypersensitivity (DTH)

Compounds were tested for their ability to treat oxazolone-induced delayed-type hypersensitivity (DTH) in mice. On day 0, mice were sensitized with 100 µL of oxazolone in 5% acetone. On day 0, 1 and 2, mice were treated by intravenous or oral administrations of the vehicle (control) or methotrexate (MTX, positive control/IV) or hydrocortisone (positive control/PO) or the compound at 50 mg/kg to 300 mg/kg of body weight. Mice were challenged with an application of 50 µL of oxazolone on the surface of the right ear (first challenge, day 3; second challenge, day 10). Ear thickness was measured on day 4 to day 7, and on day 11 to 14. Redness and crust formation was also observed. Mice were sacrificed on day 14. $T_{DTH}$ (CD4) cells play an important role in regulating the intensity of the DTH response. Compounds may exert an inhibitory influence on the DTH response through its inhibition of T-cell activation and DNA, RNA and or protein synthesis.

Figure 6:
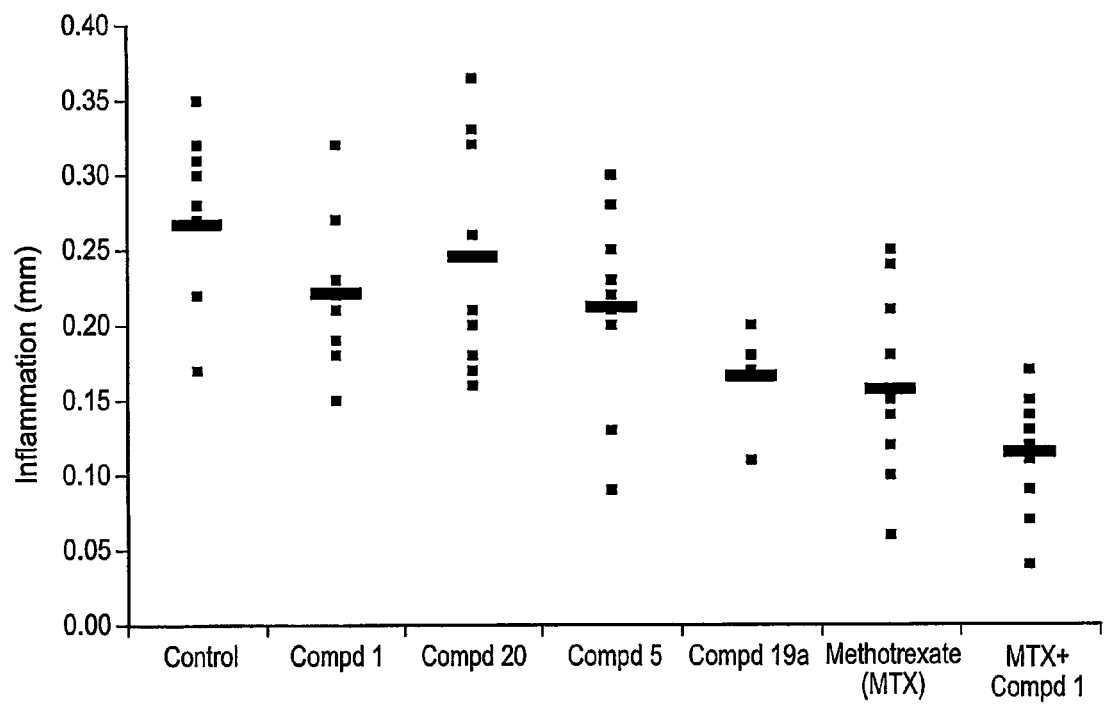
FIG. 6 illustrates the effect of compounds 1, 5 and 19a-20 on delayed-type hypersensitivity (DTH).
Figure 7:
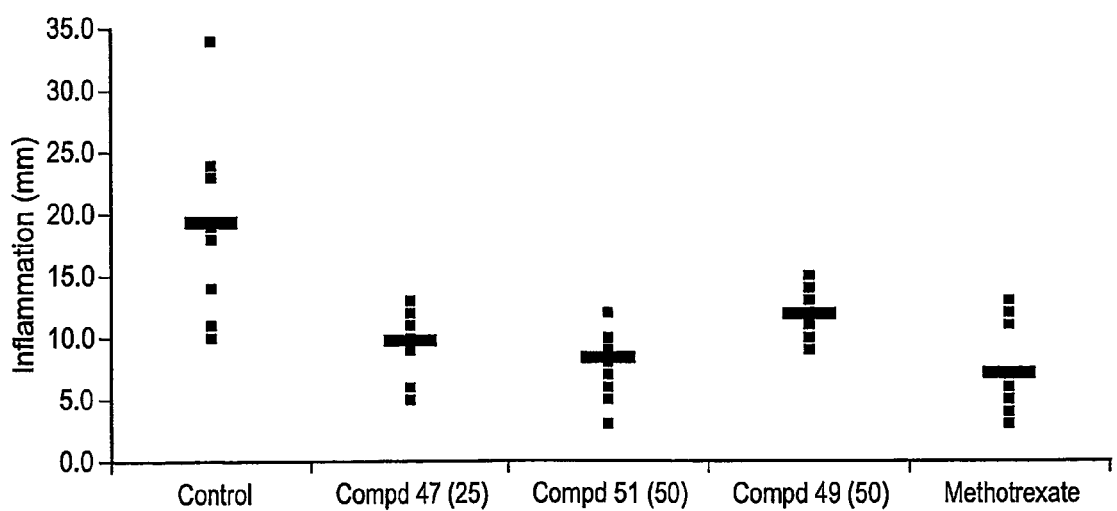
FIG. 7 illustrates the effect of compounds 47, 51 and 49 on DTH.

As illustrated in FIGS. 6 and 7, all compounds induce a significant reduction of the inflammation as seen by lower ear thickness. Also, compound 19a alone is equipotent to methotrexate. Compounds also reduce redness, crust formation and ear swelling.

Figure 8:
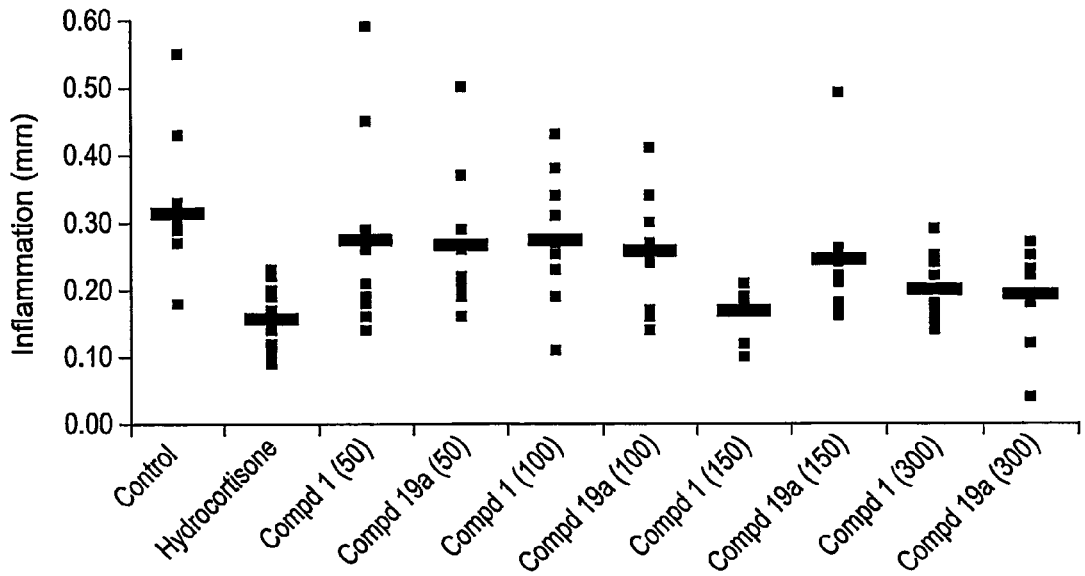
FIG. 8 illustrates the effect of compounds 1 and 19a on DTH.
Figure 9:
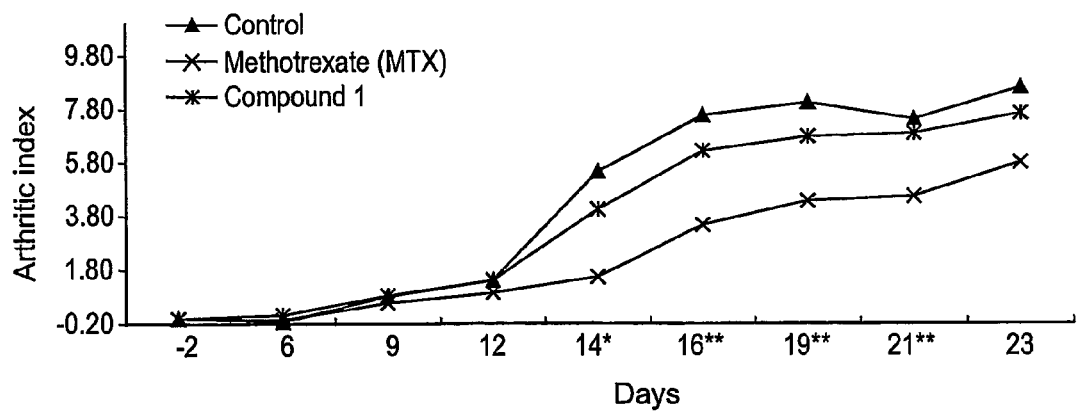
FIG. 9 illustrates the effect of compound 1 on collagen-induced arthritis.

As illustrated in FIG. 8, when administered orally at day 0, 1 and 2, compounds 1 and 19a induce a significant reduction of the inflammation as seen by lower ear thickness. Also, compounds 1 and 19a alone are equipment to hydrocortisone at concentrations of 150 mg/kg (compound 1) and 300 mg/kg (compounds 1 and 19a) of body weight. Compounds also reduce redness, crust formation and ear swelling.

Example 62

Effect of Compounds on Collagen-Induced Arthritis

Collagen-induced arthritis (CIA) was induced in female Lewis rats by intradermal administration of heterologous (bovine) type II collagen (250 µg) solubilized in 0.1 M acetic acid and emulsified in Complete Freund's Adjuvant (CFA). Rats were treated with the vehicle or methotrexate or compound 1 by intravenous injections at day 8, 9, 12, 14 and 16. Synovitis typically develops 12-15 days postimmunization in 80-90% of the animals. Once arthritis appears, each paw was examined two to three times a week. Both the incidence and severity of the arthritis was evaluated. Incidence is defined as the number of rats with clinical evidence of joint inflammation during the study period while severity was quantified by scoring daily each paw integer on a scale of 0 to 4 (0=normal, 4=maximum; Table 7) based on increasing levels of swelling, periarticular erythema and stiffness. The sum of the scores for all four paws was calculated as the arthritic index with a maximum possible score of 16 per rat. Since CIA primarily affects hind limbs, scores of 6-8 represent severe arthritis.

TABLE 7

Definition of severity score for CIA and AIA rat arthritis models

| Severity Score | Gross Pathology |
|---|---|
| 0 | No evidence of erythema and swelling |
| 1 | Erythema and mild swelling confined to the mid-foot (tarsals) or ankle joint |
| 2 | Erythema and mild swelling extending from the ankle to the mid-foot |
| 3 | Erythema and moderate swelling extending from the ankle to the metatarsal joints |
| 4 | Erythema and severe swelling encompass the ankle, foot and digits |

As illustrated in FIG. 9, 80-90% of the animals developed a severe synovitis after 12-15 days postimmunization. Inflammation reaches its maximum at day 16. A significant reduction (50%) in the severity of arthritis (arthritic index) was observed by intravenous injection of methotrexate (positive control) by day 14 and beyond. A weaker but significant reduction (20%) of the arthritic index was also observed with compound 1 from day 16 to day 21.

Example 63

Effect of Compounds on Freund's Adjuvant-Induced Arthritis (AIA)

AIA was induced in female Lewis rats by the injection of lyophilized *Mycobacterium butyricum* suspended in mineral oil into the footpad. The development of aridity was monitored over a 3 weeks period post-adjuvant injection, inflammation peaks at day 3 following the adjuvant administration. Immune activation appears around day 14. Compounds were orally or intravenously administered at different doses at day −3, −2 and −1 pre-adjuvant injection and at different regimen as specified in the exponent starting from day 10 through 21 post-adjuvant injection or animals were treated with oral admiration of compound 19a from day −3 to day 21. Body weight was recorded. The arthritis index, which is a measure of inflammation (oedema), redness and stiffness of the articulations, was used to monitor the development of the disease. The degree of arthritis was determined by measuring two perpendicular diameters of the ankles in the mediolateral and dorsoventral planes using a caliper. Joint circumference in millimeters is then calculated using a geometric formula. Both the incidence and severity of the arthritis was evaluated. Incidence is defined as the number of rats with clinical evidence of joint inflammation during the study period.

Figure 10:
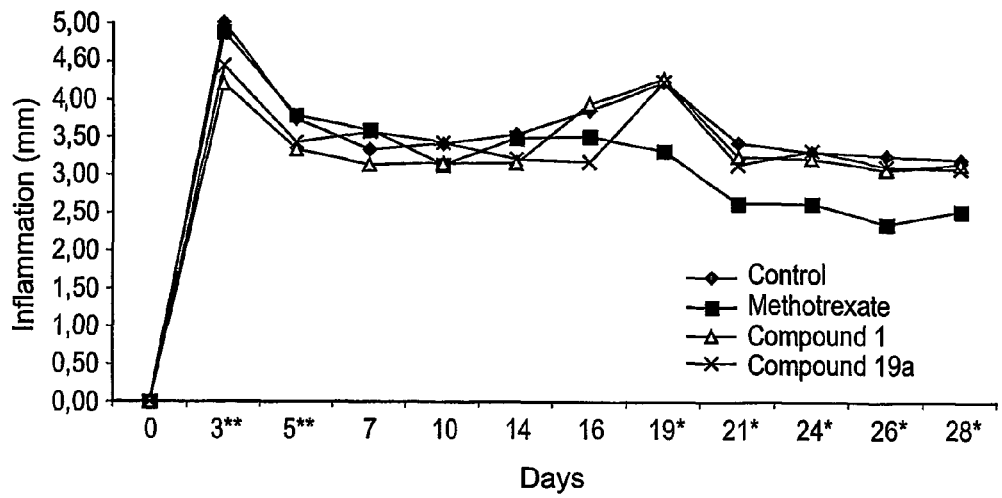
FIG. 10 illustrates the effect of compounds 1 and 19a on adjuvant-induced arthritis.

As illustrated in FIG. 10, 100% of the animals rapidly developed a synovitis. Inflammation reaches its maximum at day 3 postimmunization. Animals were treated by intravenous administration of compounds on days −3, −2, −1, 12, 13, 14, 18, 19 and 20. A significant reduction (50%) in the severity of arthritis (inflammatory index) was observed by intravenous injection of methotrexate (positive control) by day 19 and over. A weak but still significant reduction (20%) of the inflammatory index was also observed with compounds 1 and 19a from day 3 to day 5.

Figure 11:
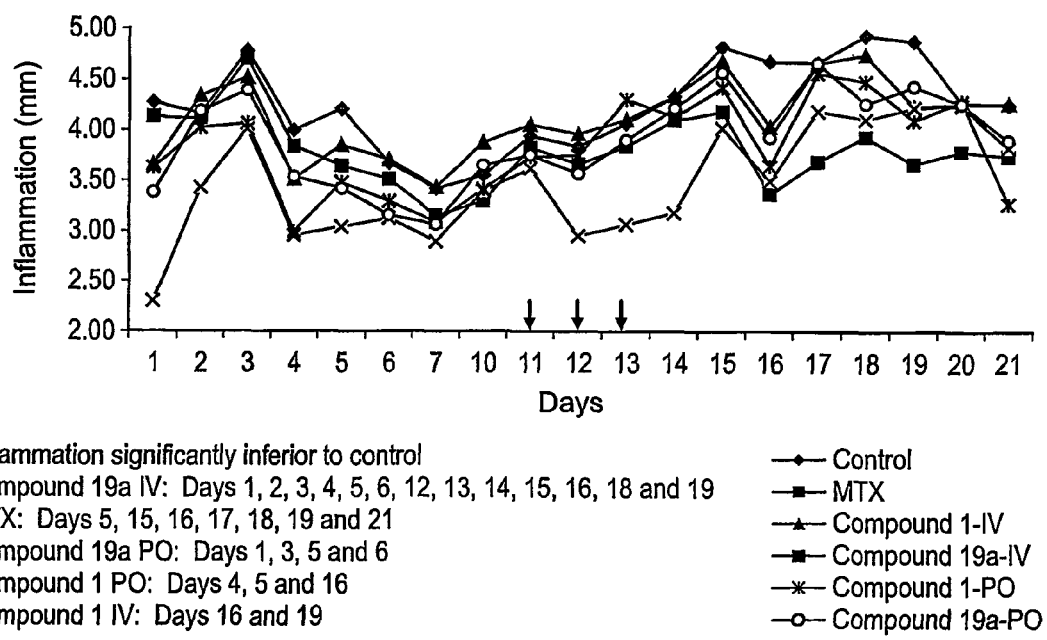
FIG. 11 illustrates the effect of oral and intravenous administration of compounds 1 and 19a on adjuvant-induced arthritis.

Furthermore in FIG. 11, a significant reduction (up to 50%) in the severity of arthritis (inflammatory index) was observed by intravenous injections (days −3, −2, −1, 11, 12 and 13) of compounds 1 and 19a on acute inflammation (days 1 to 6). Also, a significant inhibition of inflammation was observed upon oral administration of compound 19a on acute inflammation compared to the control and methotrexate. A strong and significant inhibition of inflammation was also observed on chronic inflammation (days 12 to 21) by compound 19a (IV; days 12 to 19, PO; day 16) and methotrexate (days 15 to 21).

Figure 12:
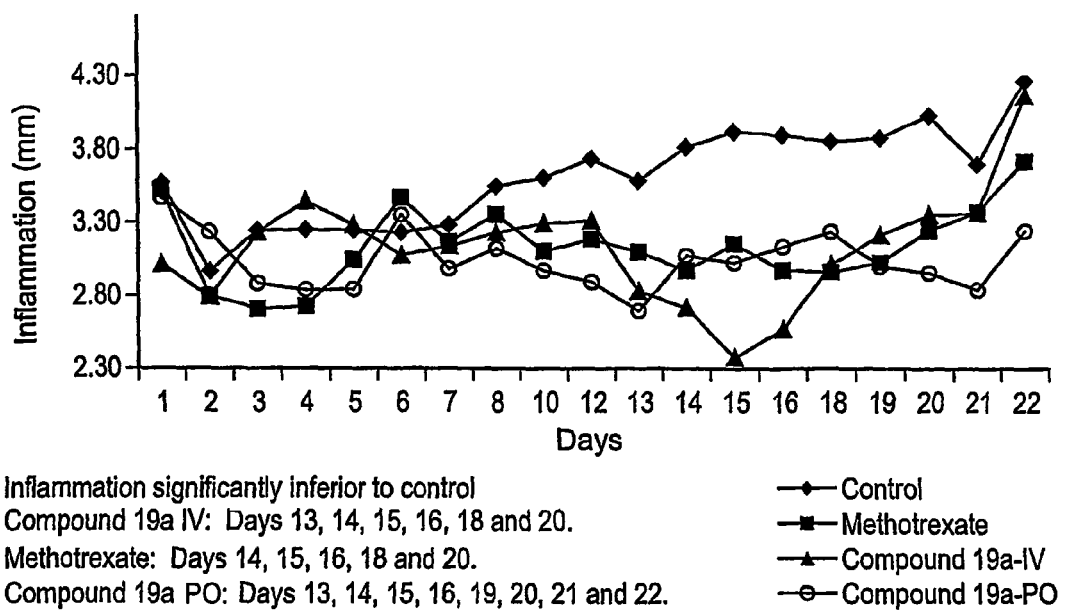
FIG. 12 illustrates the effect of oral and intravenous administration of compound 19a on adjuvant-induced arthritis.

When compound 19a was orally administered every day (days −3 to 21), a significant inhibition (up to 50%) of inflammation was observed from day 13 through day 22 (FIG. 12).

Example 64

Use of Compounds to Bind and Purify Immunoglobulins

As noted above, exemplified compounds may be used as affinity agents to bind antibody and subsequently isolate and purify the antibody from a mixture of proteins. Such purification is conveniently accomplished when the compound is first covalently linked, either directly or by a linker, to an insoluble support material. Thus 101 g of epoxide activated cross-linked (with epichlorohydrin) 6% agarose beads were treated with a solution of 6-aminohexanoic acid (8.0 g, 61 mmol) in water (101 mL) and the slurry was adjusted to pH=12 with 2 M NaOH. The reaction was shaken on a rocker plate for 44 h. The beads were filtered, washed with water (5×100 mL), then resuspended in water (100 mL) and treated with a solution of sodium borohydride (202 mg, 5.34 mmol) in 10 M NaOH (20 mL). The reaction was shaken on a rocker plate for 25 h. The beads were filtered, washed with water (11×200 mL) until the pH of the filtrate was neutral and a sample of the gel was freeze-dried for elemental analysis: C, 47.366%; H, 6.966%; N, 0.990%. Based on one atom of nitrogen per molecule of 6-aminohexanoic acid, this corresponds to a loading of 707 micromol/g freeze dried gel. The settled gel (4 g) was treated with a solution of compound 19b (275 mg, 0.30 mmol) in water adjusted to pH=4.5 (3.0 mL). A solution of 1-[3-(dimethylamino)propyl]-3-ethylcarbodiimide hydrochloride (400 mg, 2.09 mmol) in water adjusted to pH=4.5 (3.0 mL) was added to the reaction which was then shaken on a rocker plate for 21 h. The slurry was filtered, washed with 0.1 M HCl (3×10 mL) and water (10×8 mL) to yield a pale brown gel. The packed gel (200 μL in a spin column) was equilibrated in 20 mM PBS (pH=7). In this format, the exemplified compound immobilized to a solid support may be used for purification of antibody.

Figure 13:
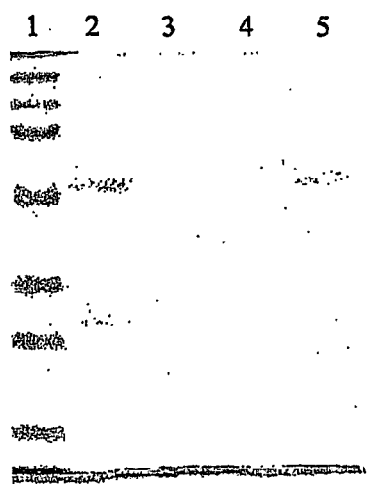
FIG. 13 illustrates denaturing (sodium dodecyl sulfate or SDS) polyacryl-amide gel electrophoresis (PAGE) of human total IgG bound and purified by compound 19b linked to the resin: lane 1, prestained standards (broad range); lane 2, human total IgG; lane 3, flow through fraction; lane 4, wash fraction; and lane 5, eluted fraction.

Solid phase binding evaluates the exemplified compounds for their ability to bind, remove, and/or purify immunoglobulins. Exemplified compounds were linked either directly or with an organic linker to an insoluble support material (resin). The gel (exemplified compound linked to the resin) was packed on a spin column. 200 μL of packed gel was equilibrated in 20 mM sodium phosphate buffer (pH=7). Total human IgG (Sigma, St. Louis, USA; purified human IgG isolated from pooled normal human serum) (see lane 2 of FIG. 13) was introduced through the gel and flow through (see lane 3 of FIG. 13) was collected The gel was washed with five-column volumes of 20 mM sodium phosphate buffer (p=7) plus 0.25 M NaCl. Wash fractions (see lane 4 of FIG. 13) were collected. Bound IgGs were eluted at low pH with 0.1 M citric acid (pH=3). Eluted IgG (see lane 5 of FIG. 13) was collected and then neutralized with Tris HCl (pH=8). SDS-PAGE (12%) of collected fractions was performed and proteins were visualized using Coomassie blue staining. As represented in FIG. 13, up to 80% of human total IgG was bound and purified when compound 19b was linked to resin by an aminohexanoic acid linker.

Patents, patent applications, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such, claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or Inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A compound of the following formula:

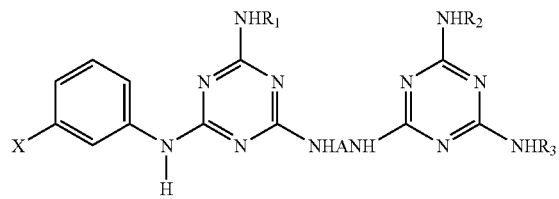

-continued

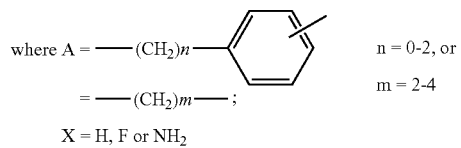

where A = —(CH$_2$)$_n$—⌬—  n = 0-2, or
    = —(CH$_2$)$_m$—;  m = 2-4

X = H, F or NH$_2$ wherein R$_1$, R$_2$, and R$_3$ are independently selected from the group consisting of

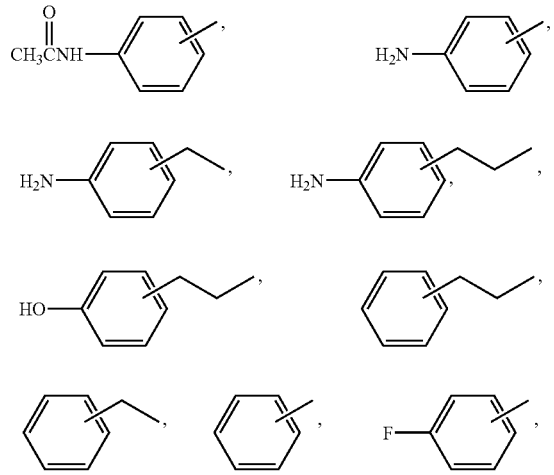

C$_{2-4}$ aminoalkyl, aminoethyloxyethyl, aminophenethyl, anilino, benzyl, bis(hydroxyethyl), bis(hydroxyethyl)aminoethyl, 1,3-dihydroxy-2-propyl, and C$_{2-4}$ hydroxyalkyl.

2. The compound according to claim 1, wherein:

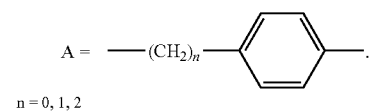

n = 0, 1, 2

3. The compound according to claim 2, wherein:
R$_1$ and R$_2$ are selected from the group consisting of aminoethyl, anilino, 1,3-dihydroxy-2-propyl, and hydroxyethyl; and
R$_3$ is selected from the group consisting of aminoethyloxyethyl, aminophenethyl, anilino, bis(hydroxyethyl), and bis(hydroxyethyl)aminoethyl.

4. The compound according to claim 3, wherein:
R$_1$ is 1,3-dihydroxy-2-propyl or hydroxyethyl; and
R$_2$ is anilino or 1,3-dihydroxy-2-propyl.

5. A compound selected from the group consisting of:
| Compound No. | Structure |
|---|---|
| 1 | 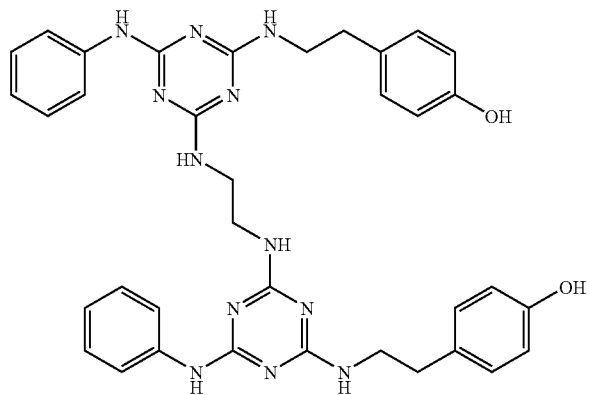 |
| 2 | 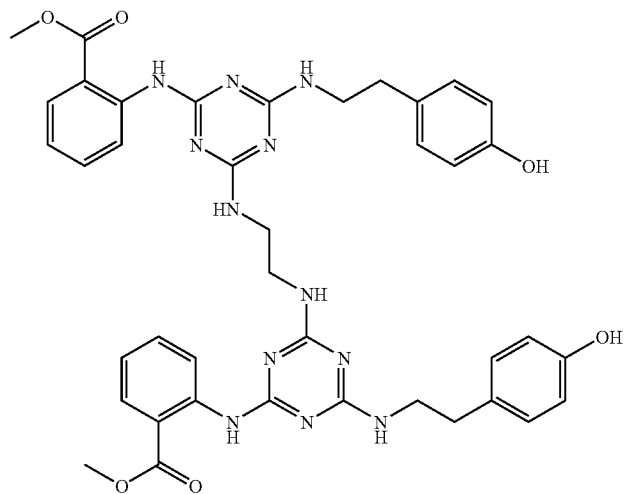 |
| 3 | 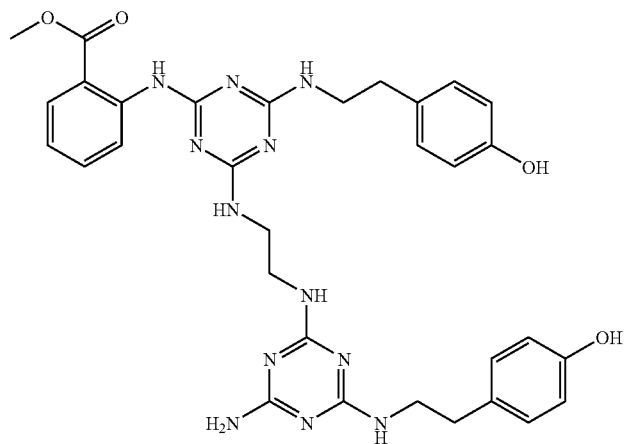 |

| Compound No. | Structure |
|---|---|
| 4 | 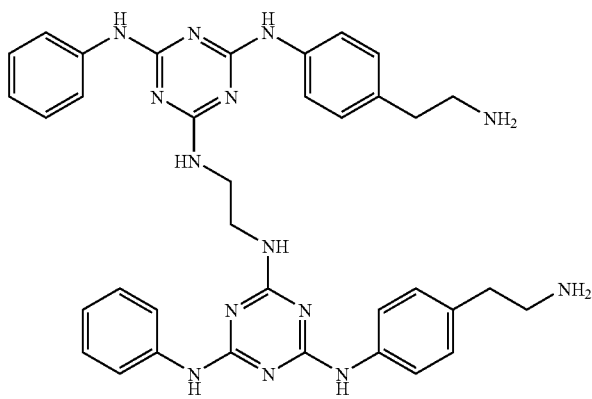 |
| 5 | 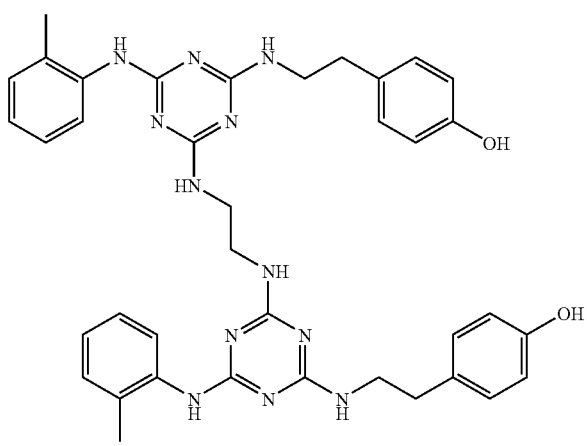 |
| 6 | 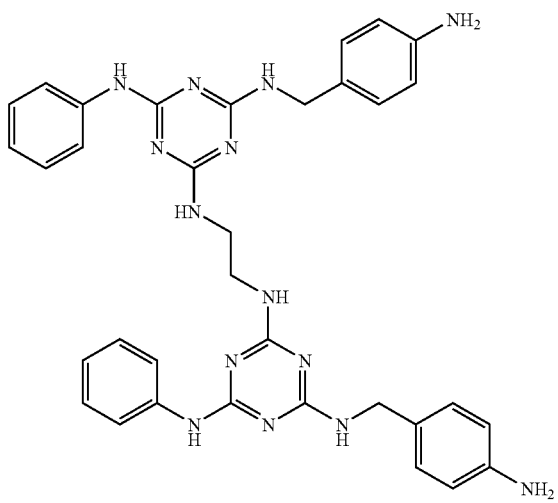 |

| Compound No. | Structure |
|---|---|
| 7 | 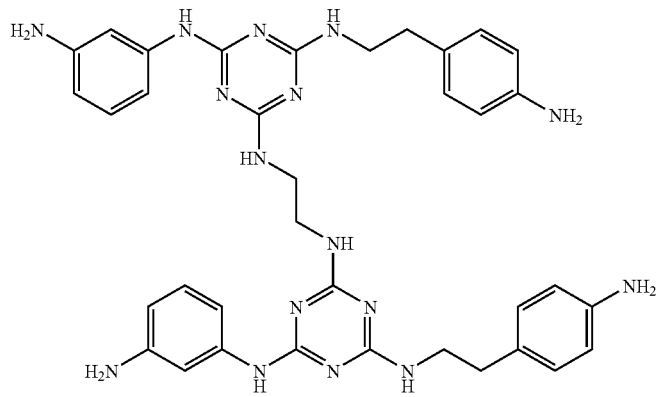 |
| 8 | 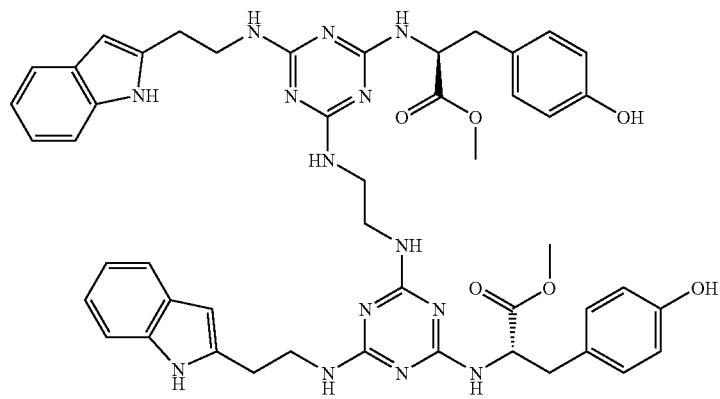 |
| 9 | 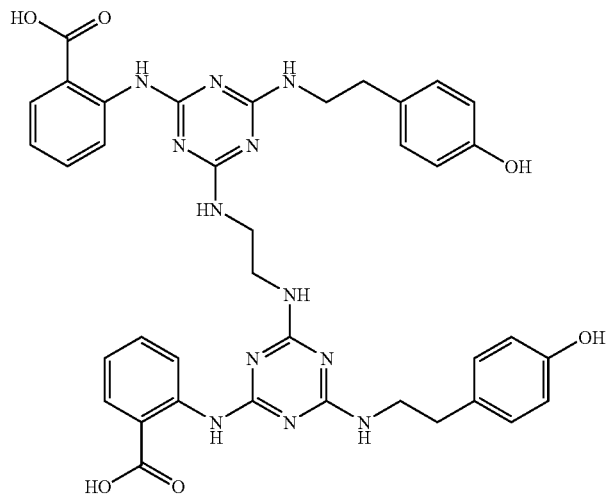 |

-continued
| Compound No. | Structure |
|---|---|
| 10 | 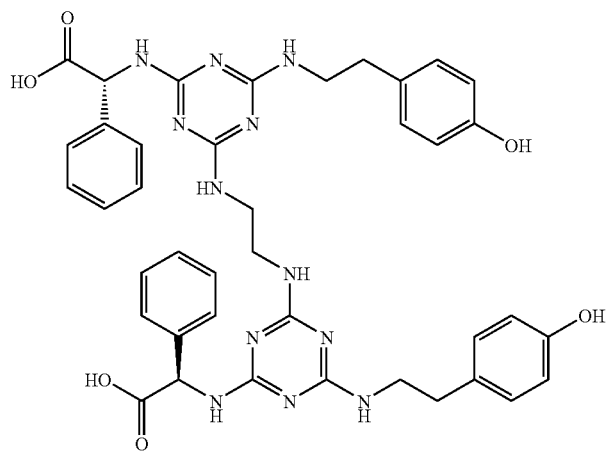 |
| 11a 11b | 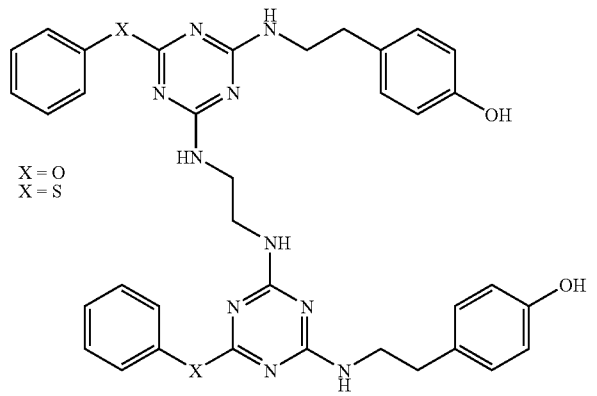
X = O
X = S |
| 12 | 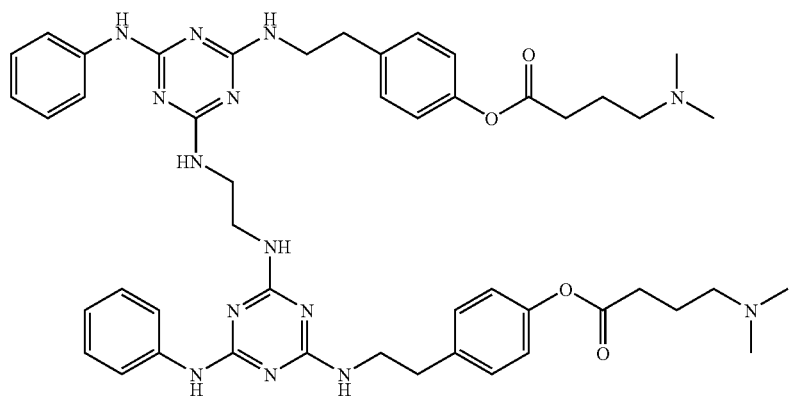 |
| 13 | 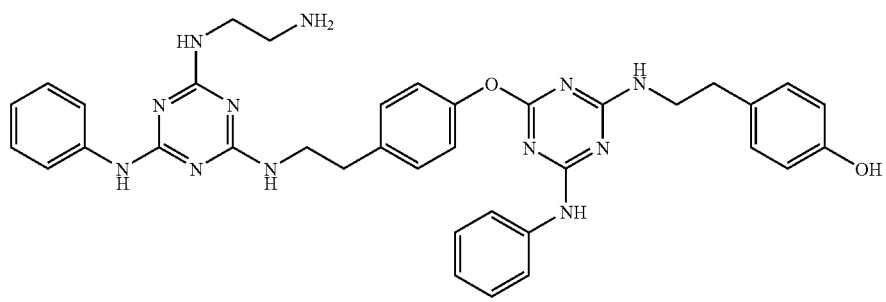 |

-continued
| Compound No. | Structure |
|---|---|
| 14 | 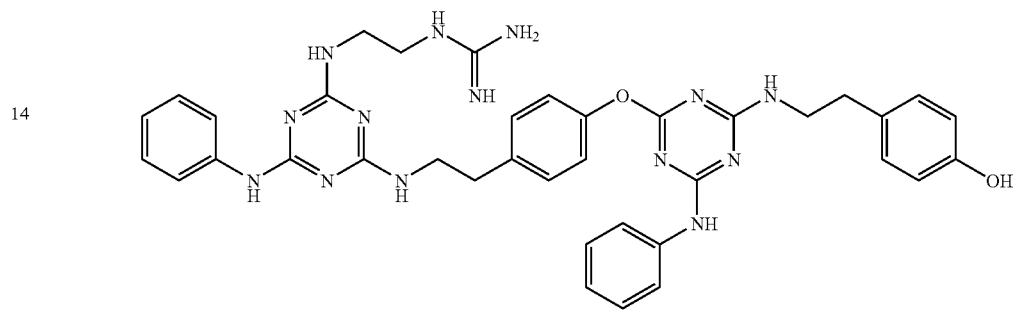 |
| 15 | 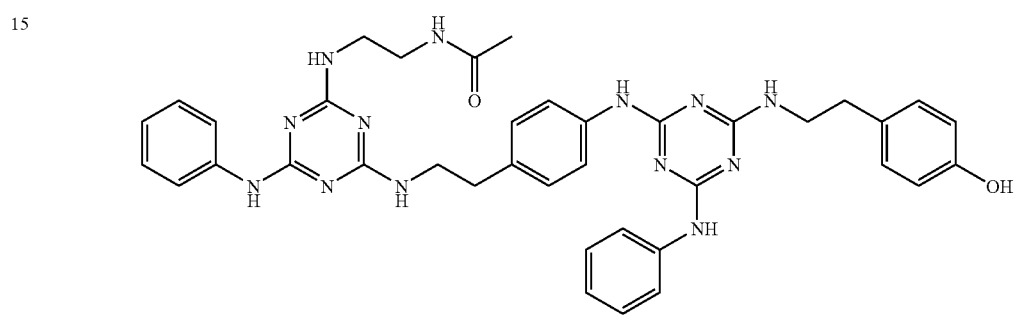 |
| 16 | 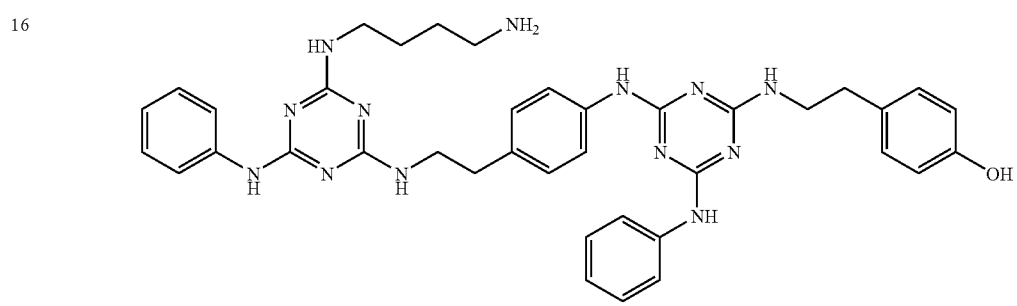 |
| 17 | 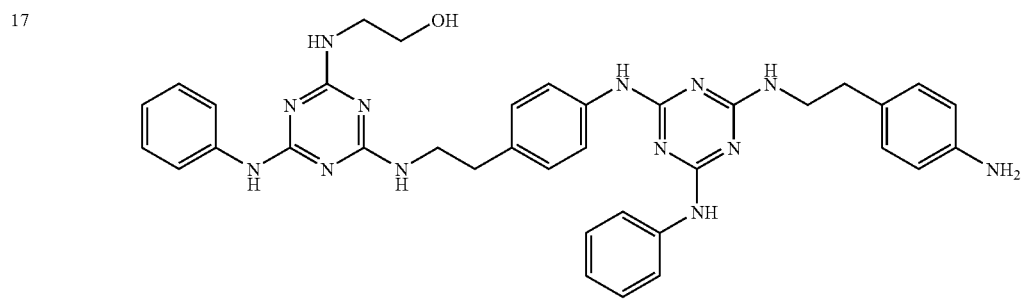 |

-continued
| Compound No. | Structure |
|---|---|
| 18 | 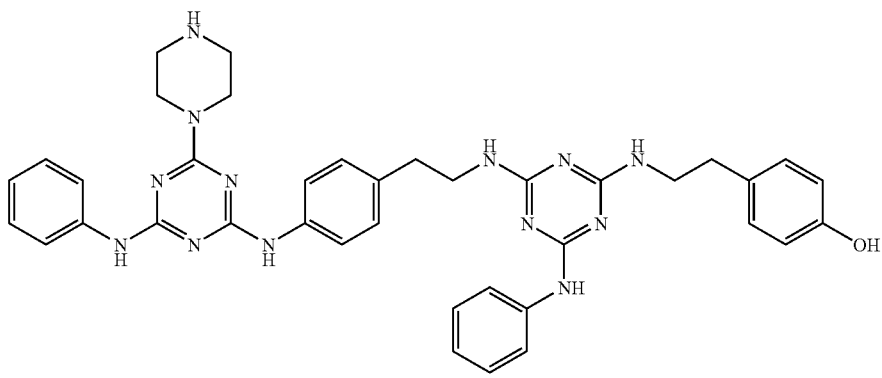 |
| 19a X = OH 19b X = NH₂ | 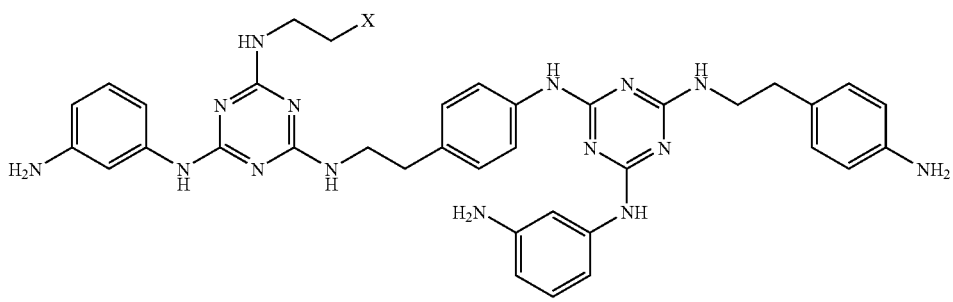 |
| 20 | 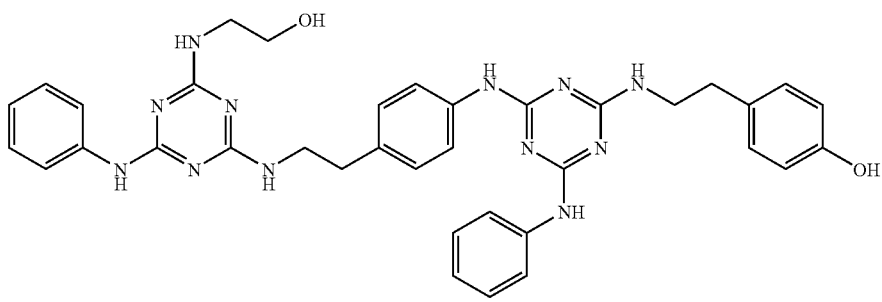 |
| 21 | 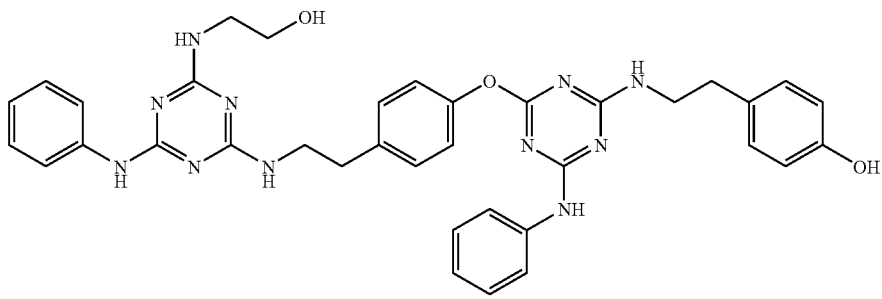 |
| 22 | 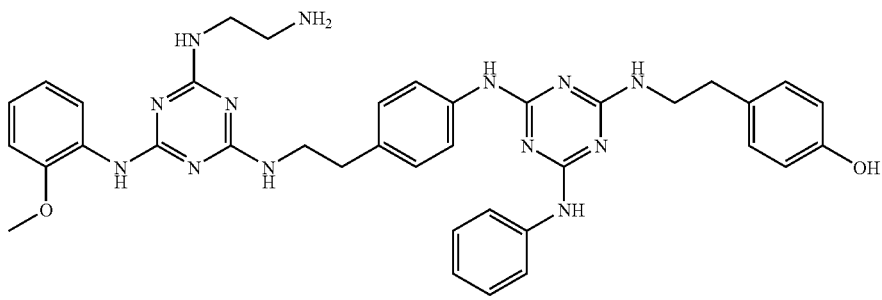 |

| Compound No. | Structure |
|---|---|
| 23 | 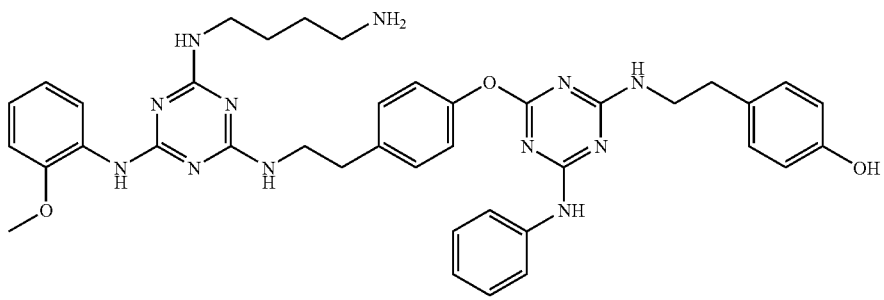 |
| 24 | 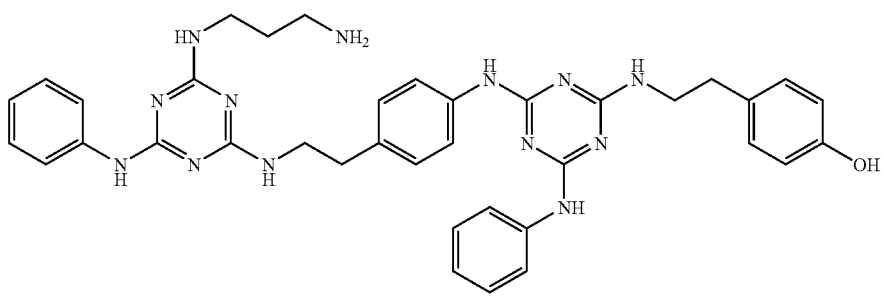 |
| 25 | 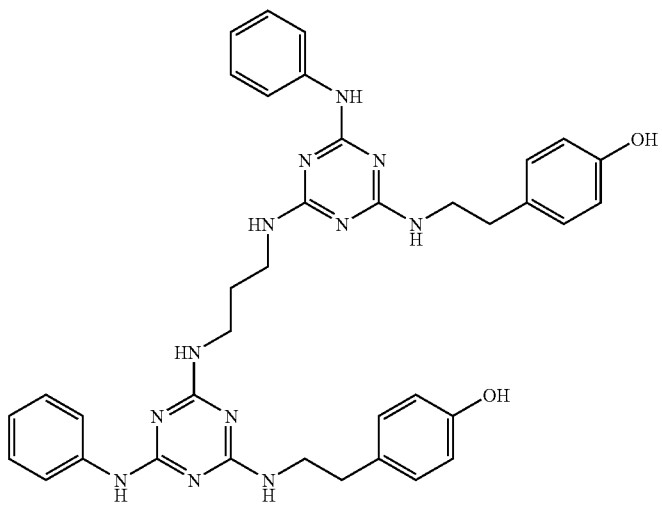 |
| 26 | 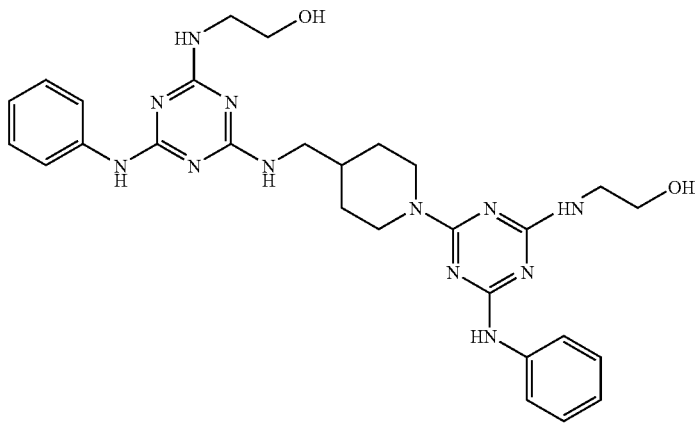 |

-continued
| Compound No. | Structure |
|---|---|
| 27 | 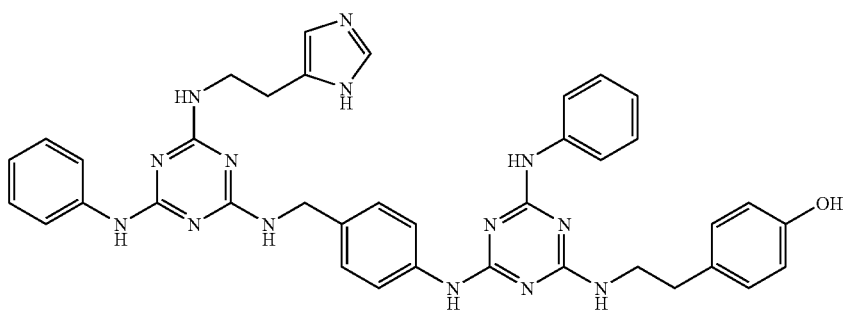 |
| 28 | 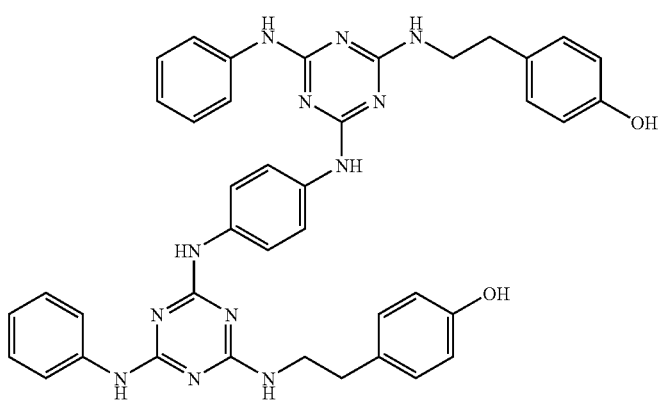 |
| 29 | 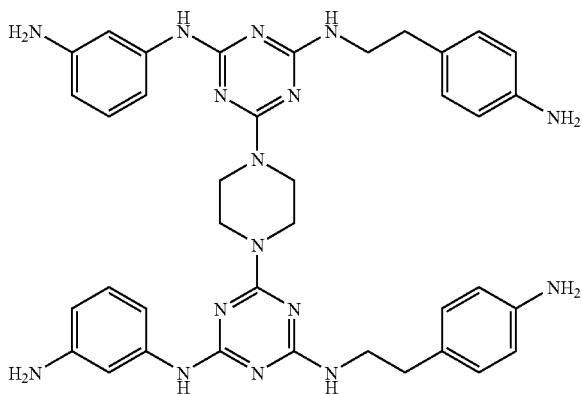 |
| 30 | 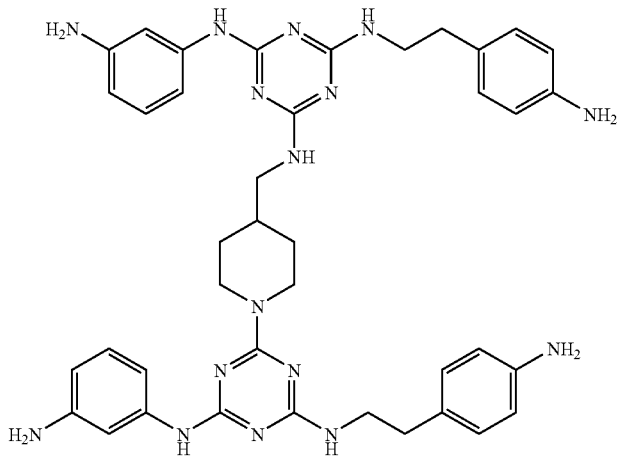 |

-continued
| Compound No. | Structure |
|---|---|
| 31 | 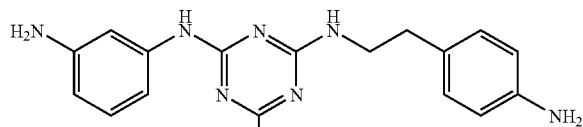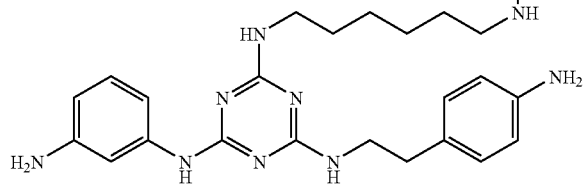 |
| 32 | 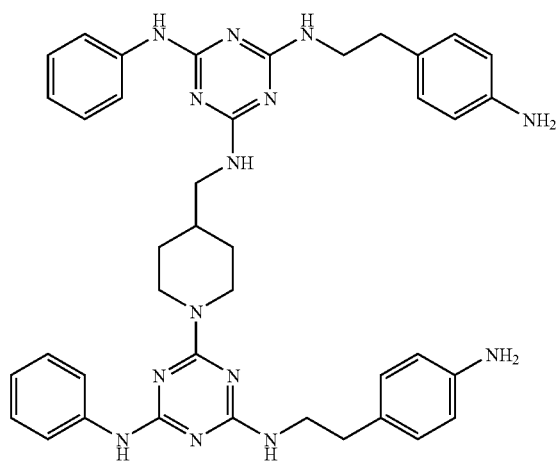 |
| 33 | 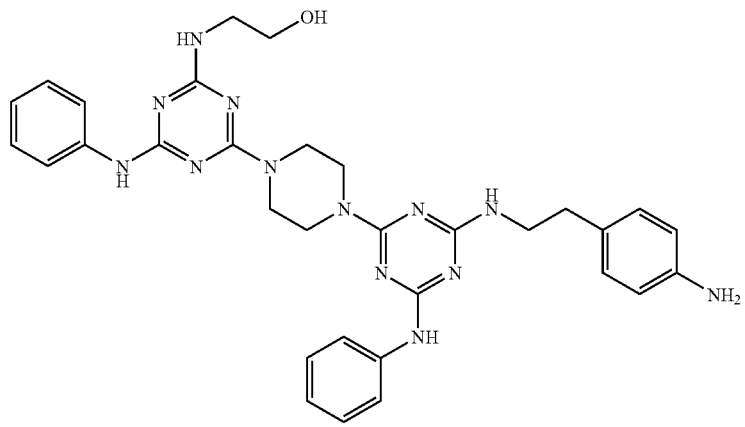 |
| 34 | 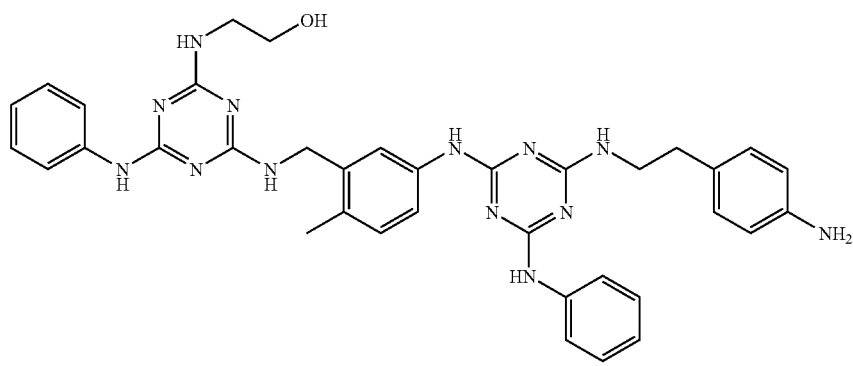 |

| Compound No. | Structure |
|---|---|
| 35 | 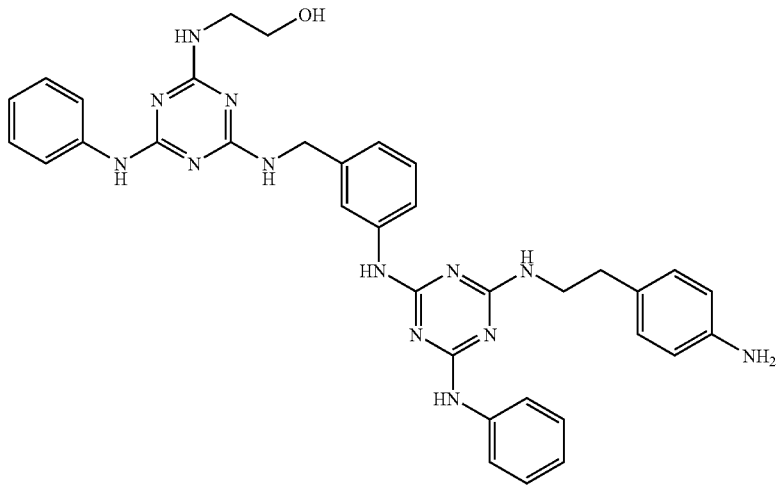 |
| 36 | 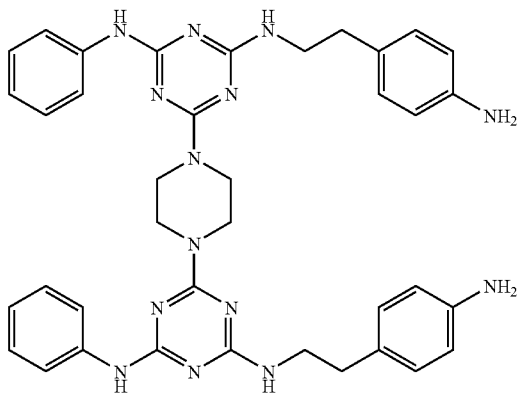 |
| 37 | 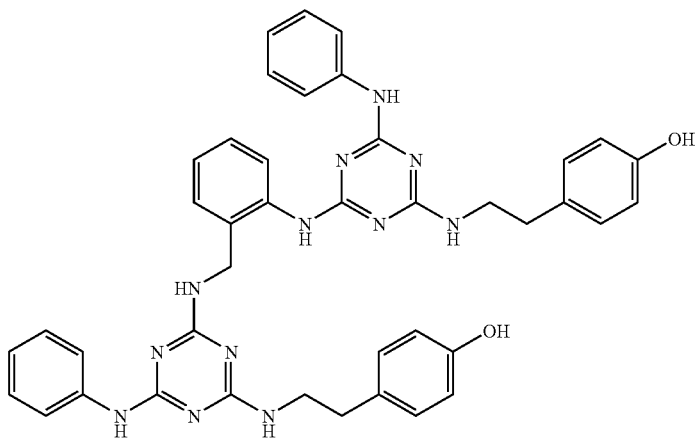 |

| Compound No. | Structure |
|---|---|
| 38 | 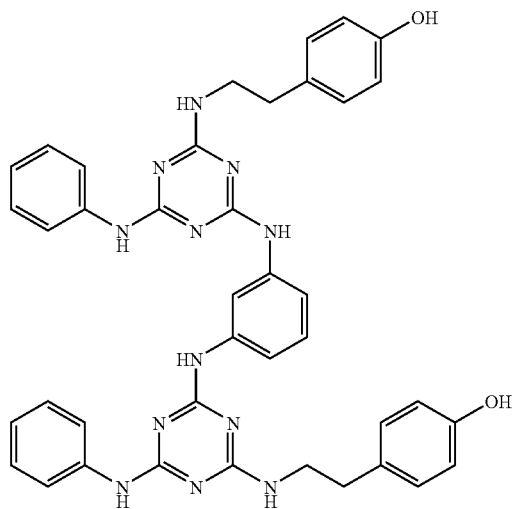 |
| 39 | 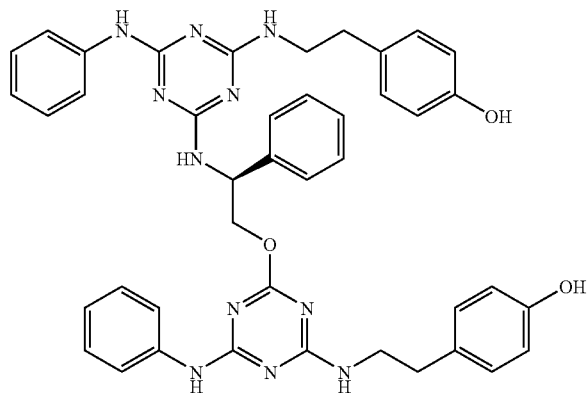 |
| 40 | 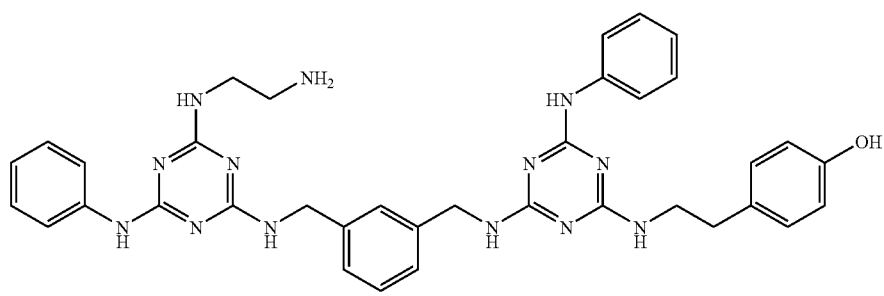 |
| 41 | 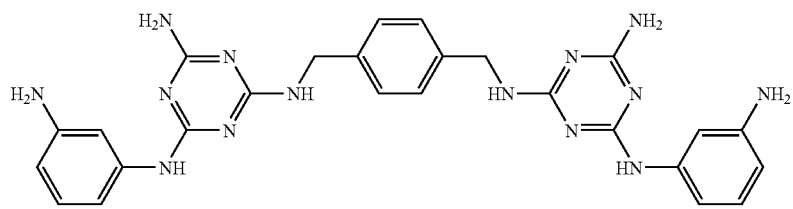 |

-continued
| Compound No. | Structure |
|---|---|
| 42 | 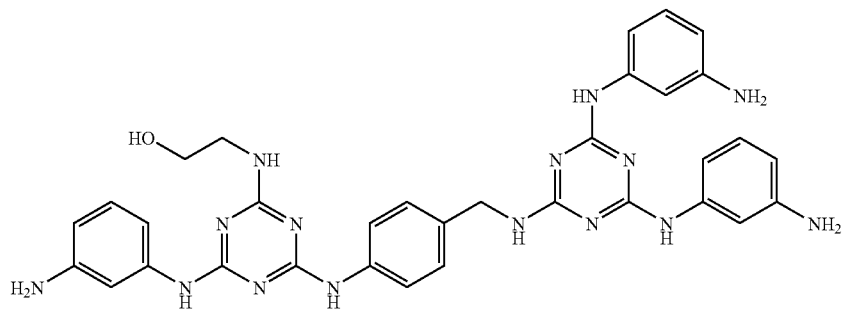 |
| 43 | 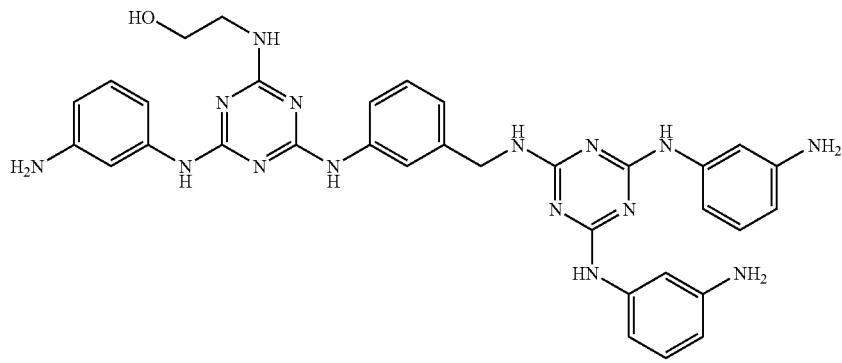 |
| 44 | 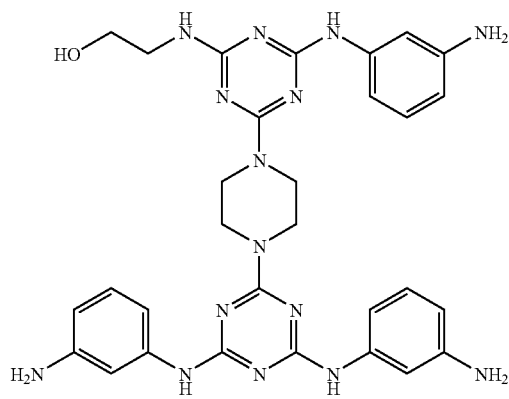 |
| 45 | 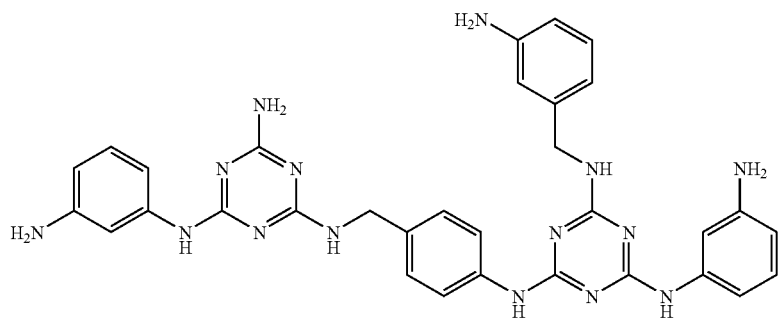 |

-continued
| Compound No. | Structure |
|---|---|
| 46 | 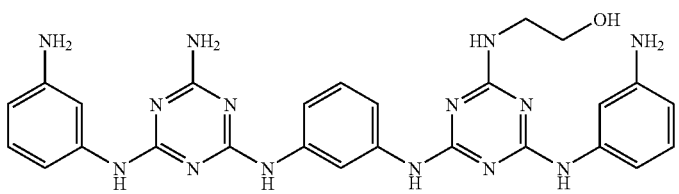 |
| 47 | 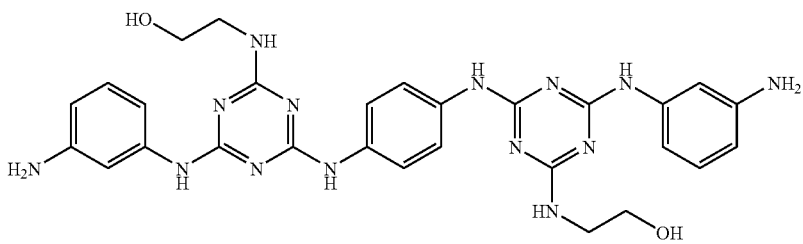 |
| 48 | 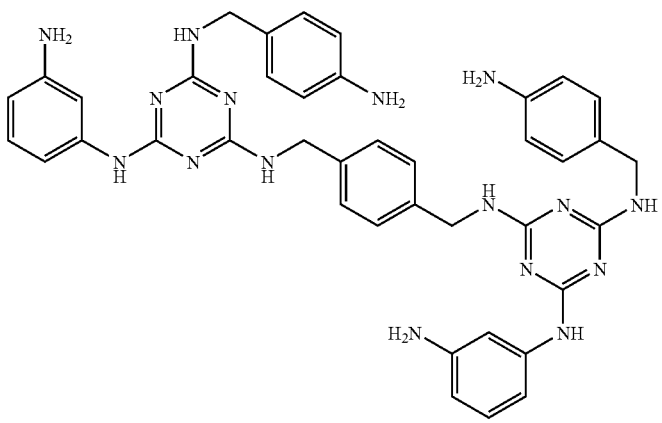 |
| 49 | 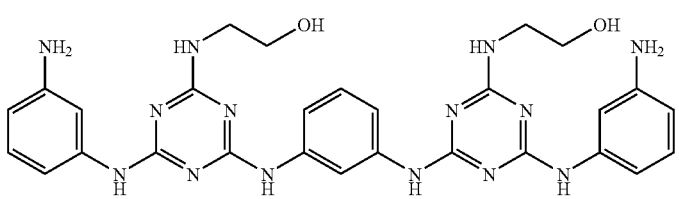 |
| 50 | 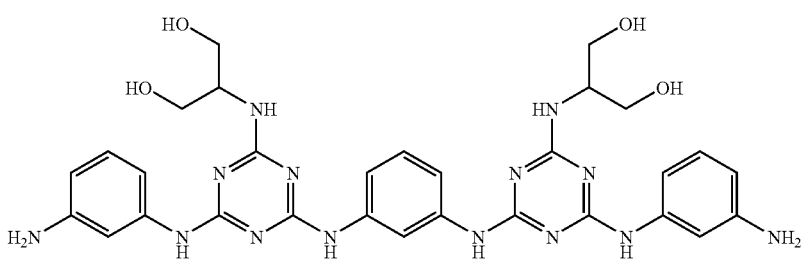 |
| | and |
| 51 | 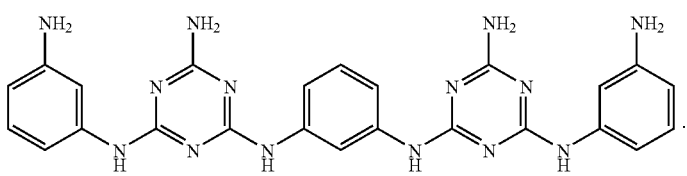 |

6. The compound according to claim 1 which can noncovalently bind to antibodies.

7. The compound according to claim 1 which can noncovalently bind to antibodies, wherein one, two, three or all of the substituents $R_1$, $R_2$, $R_3$, $R_4$ is

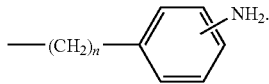

$n = 0, 1, 2$

8. The compound according to claim 6, wherein the antibodies are at least of the human IgG isotype.

9. A composition comprised of one or more compound(s) according to claim 1, wherein said compound(s) is combined with a pharmaceutically acceptable carrier.

10. The composition according to claim 9, wherein said carrier solubilizes said compound in an alcohol or polyol solvent.

11. The composition according to claim 9 further comprised of a recombinant protein which is able to bind to human TNFα.

12. The composition according to claim 11, wherein said recombinant protein is anti-TNFα antibody or soluble TNFα receptor.

13. The composition according to claim 9 further comprised of methotrexate.

14. The composition according to claim 9 further comprised of an anti-inflammatory corticosteroid.

15. The composition according to claim 9 further comprised of a nonsteroidal anti-inflammatory drug.

16. A method of treating a patient with glomerulonephritis, psoriasis, rheumatoid arthritis, or systemic lupus erythematosus comprising administering a therapeutically effective amount of a compound according to claim 1 to said patient.

17. A method of treating a patient with glomerulonephritis, psoriasis, rheumatoid arthritis, or systemic lupus erythematosus comprising administering a therapeutically effective amount of a composition according to claim 9 to said patient, wherein said composition is further comprised of methotrexate, an anti-inflammatory corticosteroid, or a nonsteroidal anti-inflammatory drug.

18. A method of treating a patient with glomerulonephritis, psoriasis, rheumatoid arthritis, or systemic lupus erythematosus comprising administering a therapeutically effective amount of a composition according to claim 11 to said patient.

19. The method of claim 16 further comprising simultaneously administering a therapeutically effective amount of a recombinant protein which is able to bind to human TNFα, wherein said therapeutically effective amount of recombinant protein is reduced in the presence of said compound.

20. The method of claim 16 further comprising separately administering therapeutically effective amount of a recombinant protein which is able to bind to human TNFα before and/or after administration of said compound, but not simultaneous administration.

21. A method of removal of human antibodies comprised of circulating blood or other physiological fluid through an apheresis column, wherein one or more compounds according to claim 1 are covalently linked either directly or with an organic linker to an insoluble support material which constitutes part of said apheresis column such that at least some free antibodies and/or antibody-antigen immune complexes are bound thereto; and returning at least some said blood or other physiological fluid, wherein at least some human antibodies have been removed therefrom, to a patient from whom said blood or other physiological fluid was obtained.

22. A method of purification of antibodies comprised of binding antibodies with one or more compounds according to claim 1 covalently linked either directly or with an organic linker to an insoluble support material such that at least some antibodies are noncovalently bound to said compounds linked to the insoluble support and purifying said antibodies.

23. A method of binding antibody using one or more compounds according to claim 1, comprised of incubating said one or more compounds to bind the antibody and then separating bound antibody from free antibody.

24. A compound selected from the group consisting of:

| Compound No. | Structure |
|---|---|
| 1 | 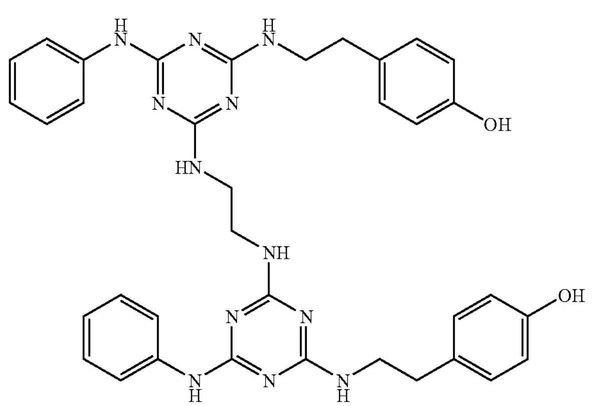 |

| Compound No. | Structure |
|---|---|
| 17 | 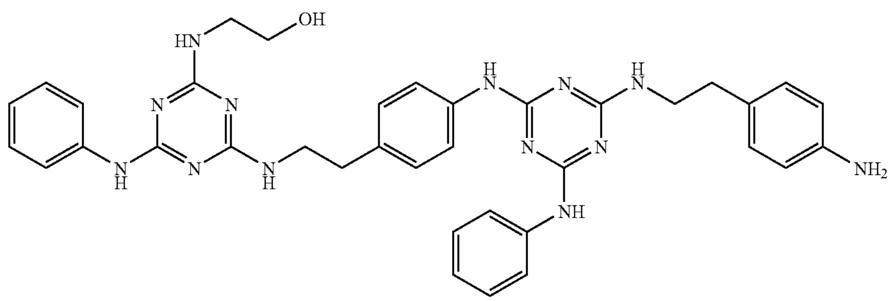 |
| 19a | 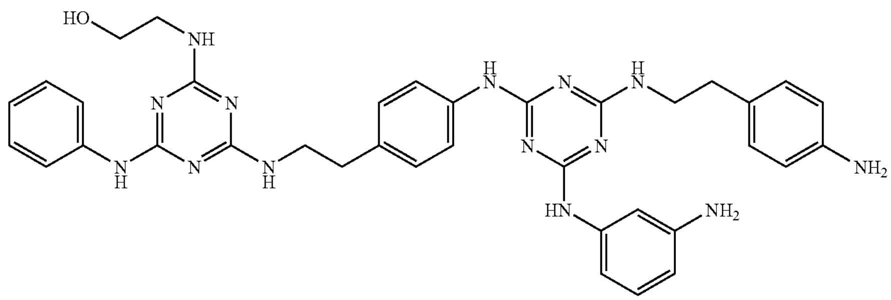 |
| 35 | 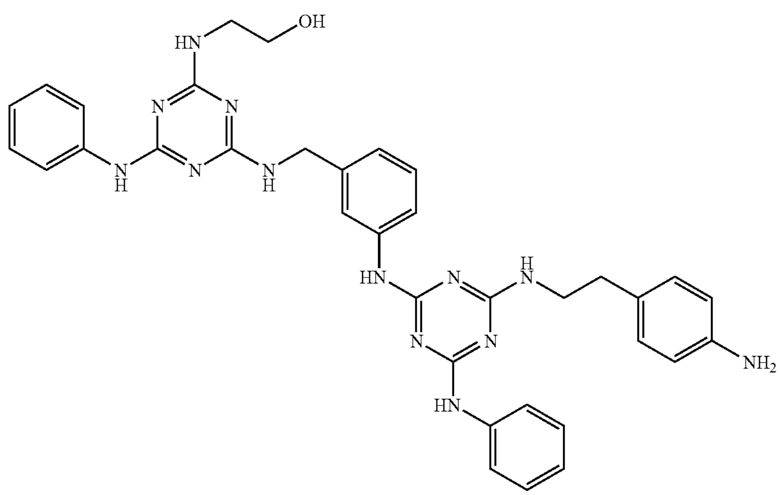 |
| 38 | 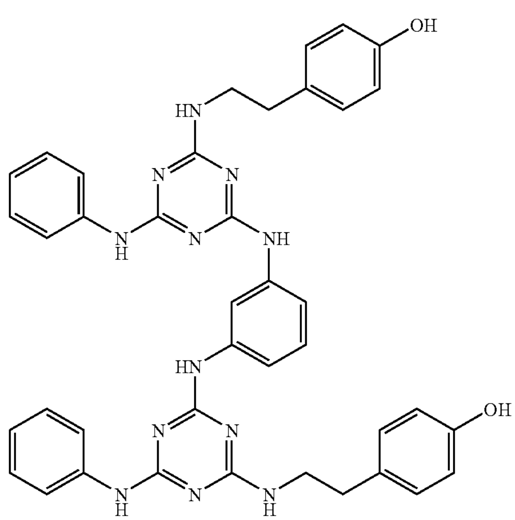 |

-continued

| Compound No. | Structure |
|---|---|
| 47 | 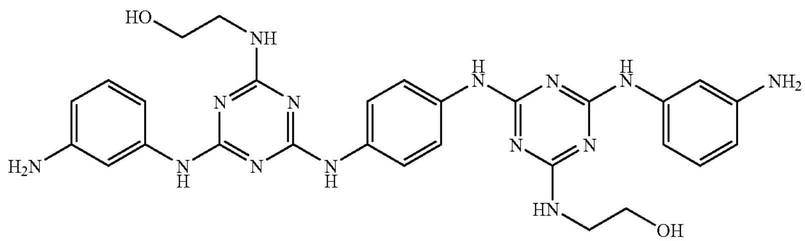 |
| 50 | 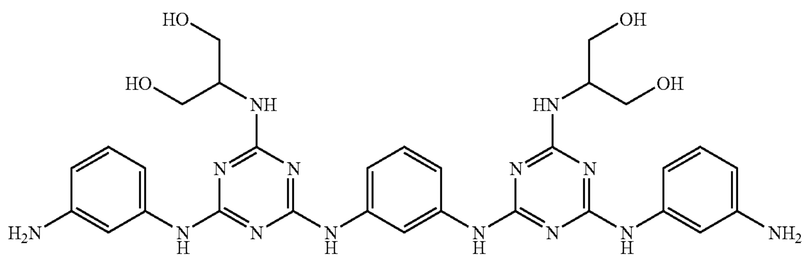 |
| 52 | 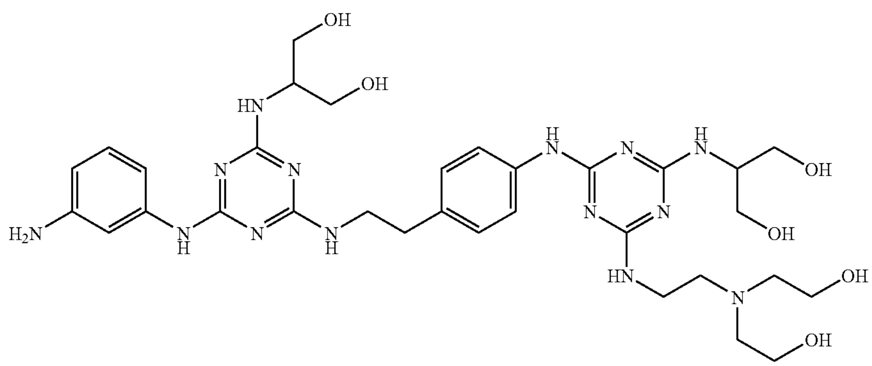 |
| 53 | 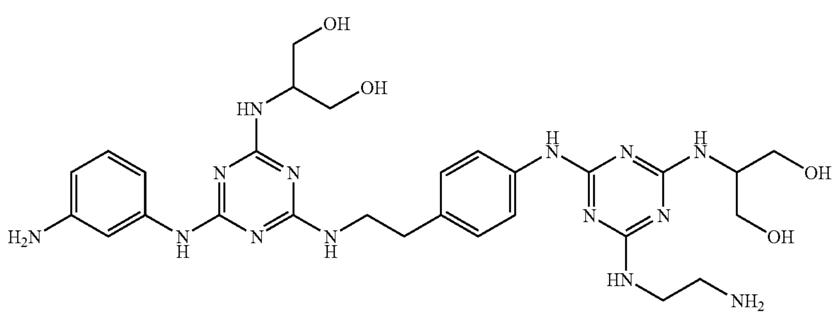 |
| 54 | 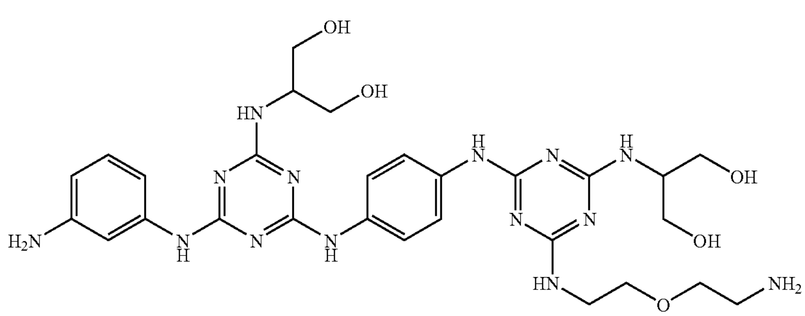 |

-continued
| Compound No. | Structure |
|---|---|
| 55 | 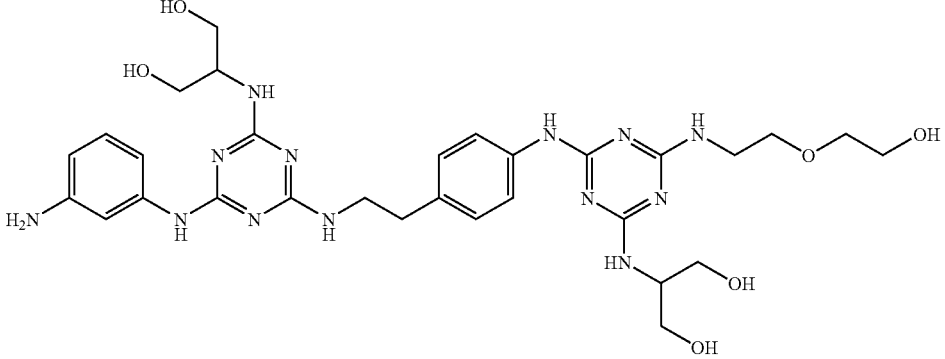 |
| 56 | 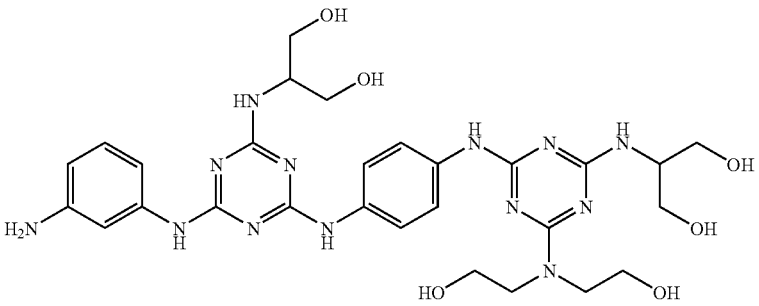 |
| 57 | 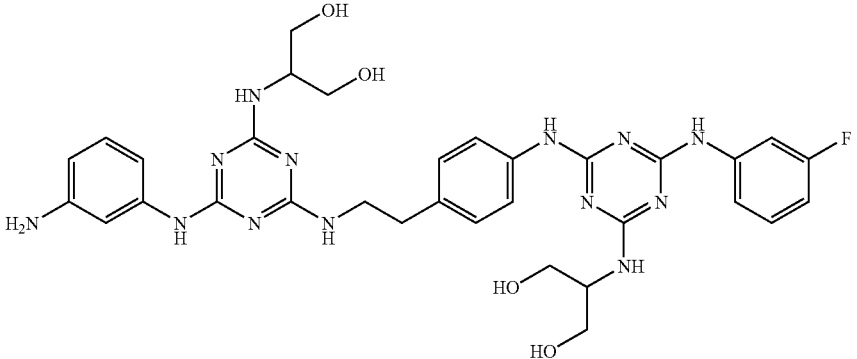 |
| 58 | 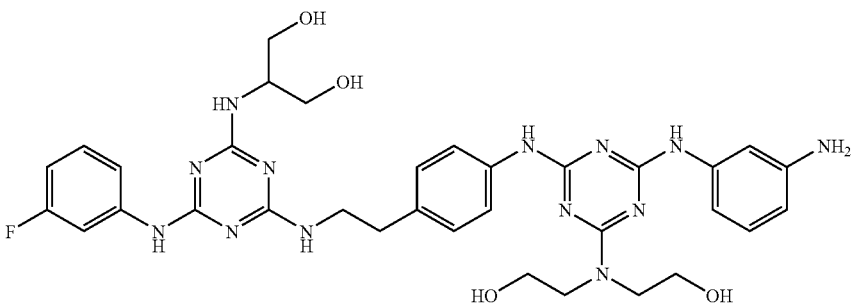 |
| 59 | 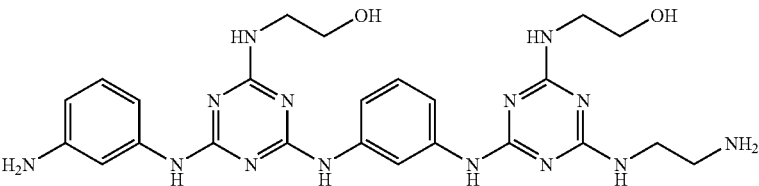 |

| Compound No. | Structure |
|---|---|
| 60 | 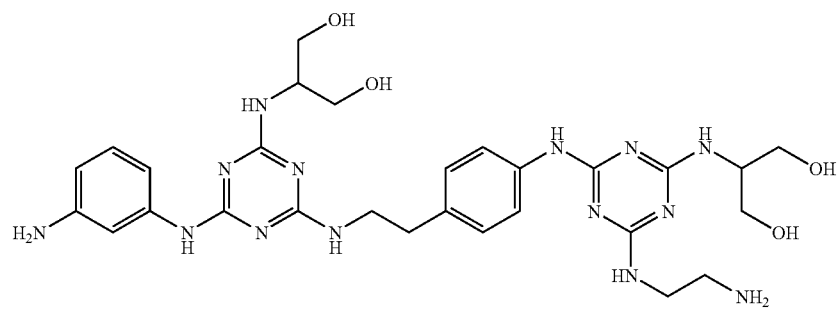 |
| 61 | 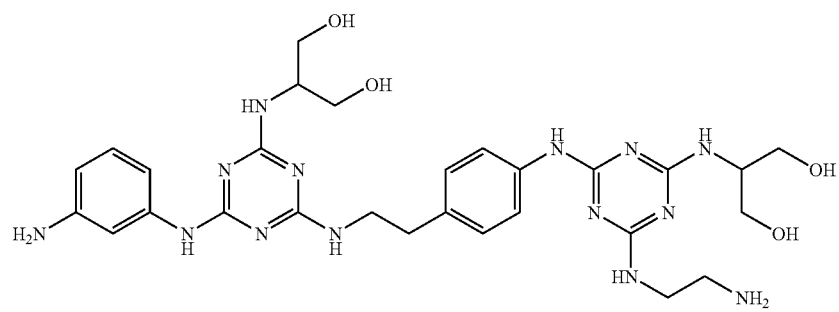 |
| 62 | 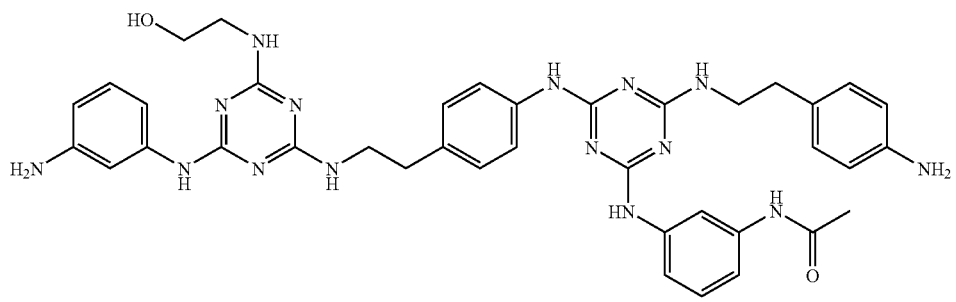 |
| 63 | 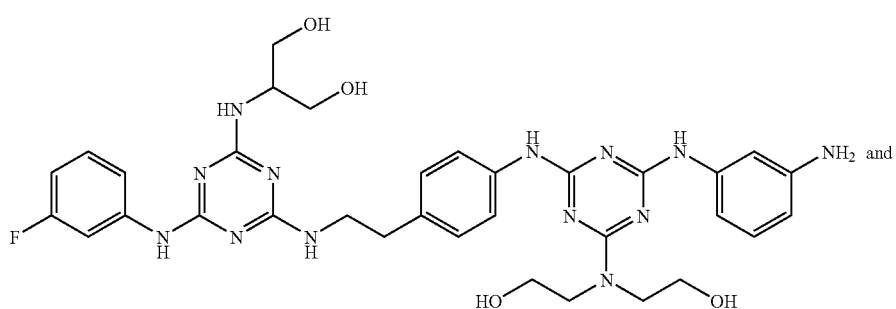 and |

-continued
| Compound No. | Structure |
|---|---|
| 64 | 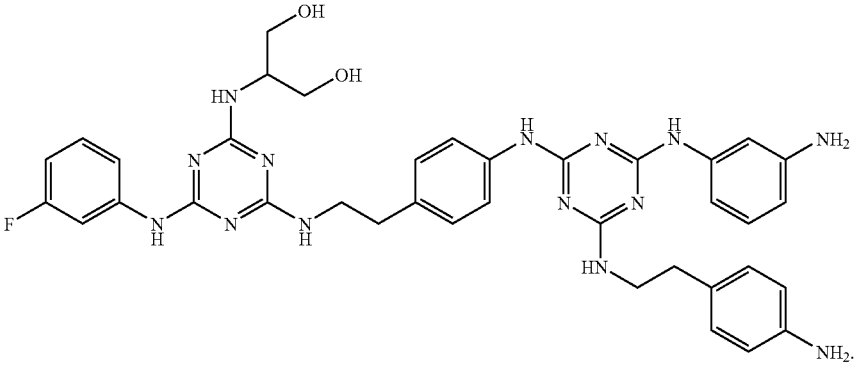 |
20
* * * * *